United States Patent
Abou El Kheir

(10) Patent No.: US 8,105,233 B2
(45) Date of Patent: Jan. 31, 2012

(54) ENDOSCOPIC SYSTEM AND METHOD FOR THERAPEUTIC APPLICATIONS AND OBTAINING 3-DIMENSIONAL HUMAN VISION SIMULATED IMAGING WITH REAL DYNAMIC CONVERGENCE

(76) Inventor: Tarek Ahmed Nabil Abou El Kheir, Sarasota, FL (US)

( * ) Notice: Subject to any disclaimer, the term of this patent is extended or adjusted under 35 U.S.C. 154(b) by 1133 days.

(21) Appl. No.: 11/877,693

(22) Filed: Oct. 24, 2007

(65) Prior Publication Data

US 2008/0027279 A1 Jan. 31, 2008

(51) Int. Cl.
*A61B 1/04* (2006.01)
*A61B 1/06* (2006.01)
*H04N 13/02* (2006.01)

(52) U.S. Cl. .......... 600/166; 600/111; 600/173; 348/47
(58) Field of Classification Search .............. 600/111, 600/166, 129, 173; 348/47
See application file for complete search history.

(56) References Cited

U.S. PATENT DOCUMENTS

| | | | |
|---|---|---|---|
| 3,994,557 A | 11/1976 | Hopkins | |
| 4,248,213 A | 2/1981 | Landre | |
| 4,369,767 A | 1/1983 | Shishido | |
| 4,517,963 A | 5/1985 | Michel | |
| 5,459,605 A | 10/1995 | Kempf | |
| 5,474,519 A | 12/1995 | Bloomer | |
| 5,647,838 A | 7/1997 | Bloomer | |
| 5,776,049 A * | 7/1998 | Takahashi | 600/111 |
| 5,797,835 A | 8/1998 | Green | |
| 5,827,172 A | 10/1998 | Takahashi | |
| 5,876,325 A | 3/1999 | Mizuno | |
| 5,949,477 A * | 9/1999 | Hoglin | 348/47 |
| 5,951,543 A | 9/1999 | Brauer | |
| 5,967,979 A | 10/1999 | Taylor | |
| 5,994,690 A | 11/1999 | Kulkarni | |

(Continued)

FOREIGN PATENT DOCUMENTS

DE 19926707 12/1999

(Continued)

OTHER PUBLICATIONS

Jatava, SK; Multislice CT: A quantum leap in whole body imaging—ijri.org-Google Scholar Search (endoscope + convergence + 3-d + 180-degree), 2007.

(Continued)

*Primary Examiner* — Philip Smith
*Assistant Examiner* — William Chou
(74) *Attorney, Agent, or Firm* — Dorothy S. Morse

(57) ABSTRACT

An endoscopic system and method that is adaptable for therapeutic applications as well as sensor operation and is capable of producing 3-dimensional human vision simulated imaging with real dynamic convergence, not virtual convergence. Applications may include use in any space, including but not limited to, intra-abdominal cavities, intra-thoracic cavities, and intra-cranial cavities. Further, two or more diagnostic/sensor probes may be used, with at least two being the same kind to create the 3-dimensional effect, such as but not limited to, camera, ultrasound, and magnetic-resonance imaging. Diagnostic/sensor probes are each mounted to the end of a different arm, with the other ends of the two arms both being attached to the same hinge that allows them to turn freely on the same axis from side-to-side within a 180 degree angle range of movement on the distal end of a main tubular shaft system. Medical, as well as other applications, are contemplated.

20 Claims, 33 Drawing Sheets

U.S. PATENT DOCUMENTS

| | | |
|---|---|---|
| 6,106,456 A | 8/2000 | Storz |
| 6,142,932 A | 11/2000 | Morizumi |
| 6,183,444 B1 | 2/2001 | Glines |
| 6,191,809 B1 | 2/2001 | Hori |
| 6,214,019 B1 | 4/2001 | Manwaring |
| 6,263,230 B1 | 7/2001 | Haynor |
| 6,312,734 B1 | 11/2001 | Kozhemyakin |
| 6,338,711 B1 * | 1/2002 | Sekiya et al. ............. 600/166 |
| 6,379,347 B1 | 4/2002 | Maki |
| 6,427,079 B1 | 7/2002 | Schneider |
| 6,459,481 B1 | 10/2002 | Schaack |
| 6,468,265 B1 | 10/2002 | Evans |
| 6,476,979 B1 | 11/2002 | Schaack |
| 6,488,697 B1 | 12/2002 | Ariura |
| 6,503,195 B1 | 1/2003 | Keller |
| 6,562,029 B2 | 5/2003 | Maki |
| 6,589,233 B1 | 7/2003 | Maki |
| 6,687,010 B1 | 2/2004 | Horii |
| 6,774,624 B2 | 8/2004 | Anderson |
| 6,798,570 B1 | 9/2004 | Greenberg |
| 6,806,899 B1 | 10/2004 | Schaack |
| 6,858,003 B2 | 2/2005 | Evans |
| 6,891,671 B1 | 5/2005 | Greenberg |
| 6,974,476 B2 | 12/2005 | McGuckin, Jr. |
| 6,980,921 B2 | 12/2005 | Anderson |
| 7,096,148 B2 | 8/2006 | Anderson |
| 7,130,119 B2 | 10/2006 | Takahashi |
| 7,133,138 B2 | 11/2006 | Horii |
| 7,155,316 B2 | 12/2006 | Sutherland |
| 7,161,741 B1 | 1/2007 | Schaack |
| 7,169,412 B2 | 1/2007 | Kozhemyakin |
| 7,170,677 B1 | 1/2007 | Bendall |
| 7,208,005 B2 | 4/2007 | Frecker |
| 7,553,277 B2 * | 6/2009 | Hoefig et al. ............. 600/173 |
| 2001/0025174 A1 | 9/2001 | Daniel |
| 2003/0055410 A1 | 3/2003 | Evans |
| 2003/0065358 A1 | 4/2003 | Frecker |
| 2003/0133191 A1 | 7/2003 | Morita |
| 2003/0137731 A1 | 7/2003 | Takahashi |
| 2003/0164952 A1 | 9/2003 | Deichmann |
| 2003/0175410 A1 | 9/2003 | Campbell |
| 2003/0184285 A1 | 10/2003 | Anderson |
| 2004/0107070 A1 | 6/2004 | Anderson |
| 2004/0111183 A1 | 6/2004 | Sutherland |
| 2004/0181375 A1 | 9/2004 | Szu |
| 2004/0225353 A1 | 11/2004 | McGuckin |
| 2004/0230095 A1 | 11/2004 | Stefanchik |
| 2004/0230096 A1 | 11/2004 | Stefanchik |
| 2004/0230097 A1 | 11/2004 | Stefanchik |
| 2004/0249246 A1 | 12/2004 | Campos |
| 2005/0020926 A1 | 1/2005 | Wiklof |
| 2005/0023356 A1 | 2/2005 | Wiklof |
| 2005/0030621 A1 | 2/2005 | Takahashi |
| 2005/0107808 A1 | 5/2005 | Evans |
| 2005/0165297 A1 | 7/2005 | Anderson |
| 2005/0168751 A1 | 8/2005 | Horii |
| 2005/0234296 A1 * | 10/2005 | Saadat et al. ............. 600/129 |
| 2005/0234302 A1 | 10/2005 | MacKinnon |
| 2005/0237606 A1 | 10/2005 | Greenberg |
| 2005/0261674 A1 | 11/2005 | Nobis |
| 2006/0004306 A1 | 1/2006 | Altshuler |
| 2006/0004347 A1 | 1/2006 | Altshuler |
| 2006/0007841 A1 | 1/2006 | Masui |
| 2006/0020309 A1 | 1/2006 | Altshuler |
| 2006/0058712 A1 | 3/2006 | Altshuler |
| 2006/0082657 A1 | 4/2006 | Meier |
| 2006/0219776 A1 | 10/2006 | Finn |
| 2006/0237652 A1 | 10/2006 | Kimchy |
| 2006/0241748 A1 * | 10/2006 | Lee et al. ............. 623/2.37 |
| 2007/0016112 A1 | 1/2007 | Schultheiss |
| 2007/0032701 A1 | 2/2007 | Fowler |
| 2007/0032906 A1 | 2/2007 | Sutherland |
| 2007/0035797 A1 | 2/2007 | Kanai |
| 2007/0047072 A1 | 3/2007 | Zimmer |
| 2007/0055125 A1 | 3/2007 | Andersen |
| 2007/0057211 A1 | 3/2007 | Bahlman |
| 2007/0142825 A1 | 6/2007 | Prisco |
| 2007/0145136 A1 | 6/2007 | Wiklof |
| 2007/0165306 A1 | 7/2007 | Bendall |
| 2007/0167784 A1 | 7/2007 | Shekhar |
| 2007/0179525 A1 | 8/2007 | Frecker |
| 2007/0182812 A1 | 8/2007 | Ritchey |
| 2007/0197899 A1 | 8/2007 | Ritter |
| 2007/0239082 A1 | 10/2007 | Schultheiss |

FOREIGN PATENT DOCUMENTS

| | | |
|---|---|---|
| DE | 19933526 | 1/2000 |
| JP | 61080221 | 4/1986 |
| JP | 3118509 | 8/1991 |
| JP | 4070710 | 3/1992 |
| JP | 4227226 | 8/1992 |
| JP | 4289811 | 10/1992 |
| JP | 5127080 | 5/1993 |
| JP | 5107471 | 9/1993 |
| JP | 5297272 | 11/1993 |
| JP | 6160731 | 6/1994 |
| JP | 6202006 | 7/1994 |
| JP | 7222712 | 8/1995 |
| JP | 7327926 | 12/1995 |
| JP | 8094965 | 4/1996 |
| JP | 8094966 | 4/1996 |
| JP | 8150114 | 6/1996 |
| JP | 4138357 | 5/1999 |
| JP | 11151243 | 6/1999 |
| JP | 11169340 | 6/1999 |
| JP | 11337845 | 12/1999 |
| JP | 2003322803 | 11/2003 |
| JP | 2005034659 | 2/2005 |
| JP | 2005334462 | 12/2005 |
| JP | 2005342033 | 12/2005 |
| WO | WO 80/01641 | 8/1980 |
| WO | WO94/10805 | 5/1994 |
| WO | WO 94/13189 | 6/1994 |
| WO | WO 94/20875 | 9/1994 |
| WO | WO 95/15661 | 6/1995 |
| WO | WO 97/17882 | 5/1997 |
| WO | WO 98/22782 | 6/1997 |
| WO | WO 97/43680 | 11/1997 |
| WO | WO 98/07001 | 2/1998 |
| WO | WO 98/38908 | 9/1998 |
| WO | WO 99/00062 | 1/1999 |
| WO | WO9413189 | 6/1999 |
| WO | WO 99/37098 | 7/1999 |
| WO | WO 00/027281 | 5/2000 |
| WO | WO 00/33723 | 6/2000 |
| WO | WO 01/13160 | 2/2001 |
| WO | WO 01/27684 | 4/2001 |
| WO | WO 2001/050947 | 7/2001 |
| WO | WO 01/87176 | 11/2001 |
| WO | WO 02/16867 | 2/2002 |
| WO | WO 02/41250 | 5/2002 |
| WO | WO 03/079985 | 10/2003 |
| WO | WO 03/088143 | 10/2003 |
| WO | WO 2004/014244 | 2/2004 |
| WO | WO 2004/042546 | 5/2004 |
| WO | WO 2005/000110 | 1/2005 |
| WO | WO 2005/048827 | 6/2005 |
| WO | WO 2005/078502 | 8/2005 |
| WO | WO 2006/054116 | 5/2006 |
| WO | WO 2006/129713 | 11/2006 |
| WO | WO 2007/008289 | 1/2007 |
| WO | WO 2007/015710 | 2/2007 |
| WO | WO 2007/036681 | 4/2007 |
| WO | WO 2007/057786 | 5/2007 |
| WO | WO 2007/078304 | 7/2007 |
| WO | WO 2007/097539 | 8/2007 |
| WO | WO2007/113713 | 10/2007 |

OTHER PUBLICATIONS

Narasimhan, S; Analytic rendering of multiple scattering in participating media—cs.columbia.edu—Google Scholar Search (endoscope + convergence + 3-d + 180-degree), 2004.

Deichmann, N: Method and apparatus for three-dimensional optical scanning of interior surfaces—freepatent(Google Scholar Search (endoscope + convergence + 3-d + 180-degree), 2001.

Kimchy, Y; Apparatus and methods for imaging and attenuation correction-freepatentsonline.com. Google Scholar Search (endoscope + convergence + 3-d + 180 degree), 2003.
Finn, D; RFID Reader With Multiple Interfaces—freepatentsonline.com—Google Scholar Search (endoscope + convergence + 3-d + 180-degree), 2006.
Ridley, Panoramic image-based wirtual reality/telepresence audio-visual system—freepatentsonline—Google Scholar Search (endoscope + convergence + 3-d + 180-degree), 2005.
Hirzinger, G; Mechatronics for a new robot generation—Mechatronics, IEEE/ASME Transactions on, 1996—Goodle Scholar Search (endoscope + convergence + 3-d + gearbox), 1996.
Zimmer, Greenough-Type Stereomicroscope—freepatentsonline.comGoogle Scholar Search (endoscope + convergence + 3-d + gear + box), 2006.
Lavallée, S; An Overview of Computer-Integrated Surgery & Therapy—Critical Reviews in Computed Tomography, Google Scholar Search (endoscope + convergence + 3-d + gear + box), 2000.
Liu, A; A Survery of Surgical Simulation: Applications, Technology, and Education—2002—simcen.org—; Google Scholar Search (endoscope + convergence + 3-d + gear + box), 2003.
Center, S; A Survey of Surgical Simulation: Applications, Technology, and Education—MIT Press—Google Scholar Search Search (endoscope + convergence + 3-d + gear + box), 2003.

Faulkner, G; Virtual Reality Laboratory for Medical Applications—doi.wiley.com-Google Scholar Search (endoscope + convergence +0 3-d + gear + box), 2001.
Merlet, JP; Parallel Robots—2000—books.google.com—Google Scholar Search (endoscope + convergence + 3-d + gear + box), 2000.
Dowling, KJ; Limbless Locomotion: Learning to Crawl with a Snake Robot—library.solarbotics.net—Google Scholar Search (endoscope + convergence + 3-d +gear + box), 1997.
Thompson, RL; Integration of Visual and Haptic Feedback for Teleoperation—2001—citeseer.comp.nus.ed.sg-Google Scholar Search (endoscope + convergence + 3-d ' gear + box).
Paulus, D; Mixed-reality as a challenge to image understanding and artificial intelligence—uni-koblenz.de-Google Scholar Search (endoscope + convergence + 3-d + gear + box), 2005.
Attendees, W; Appendix C. Site Reports—Europe—wtec.org-Google Scholar Search (endoscope + convergence + 3-d + gear + box), 2005.
Jain, S; Modeling and Simulation for Emergency Response: Workshop Report, Standards and Tools—2003—Google Scholar Search (endoscope + convergence + 3-d + gear + box), 2003.
Feil, P; Next generation Internet in Europe Commission. European, Director—1999-cordis.lu-Google Scholar Search (endoscope + convergence + 3-d + gear + box).

* cited by examiner

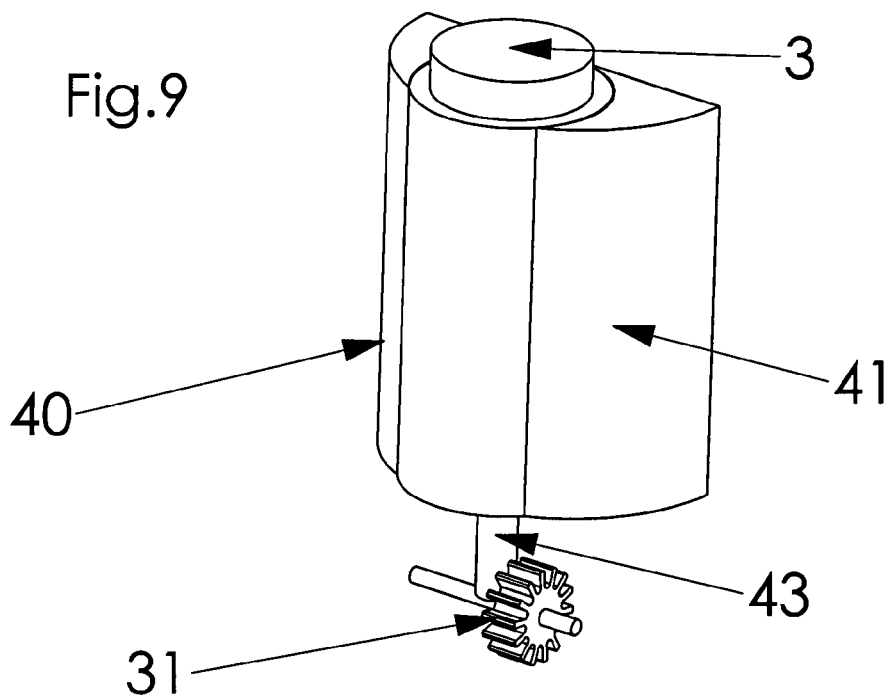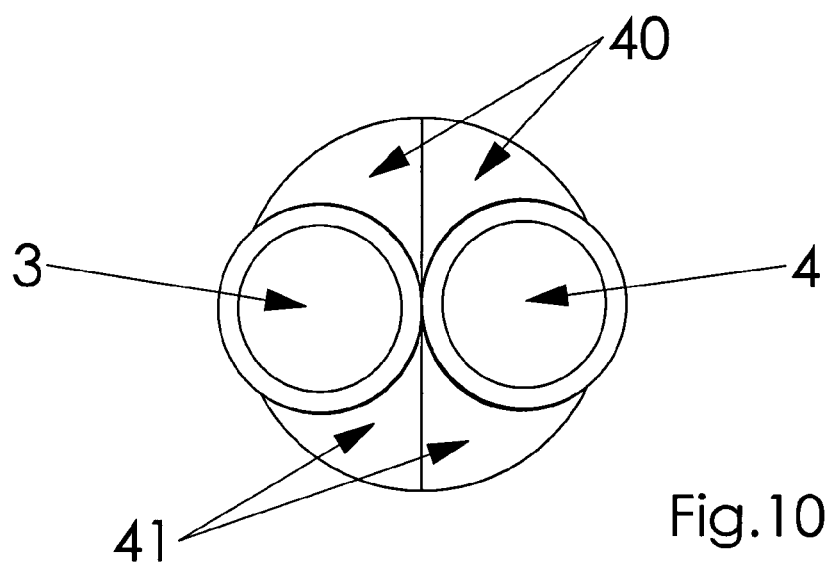

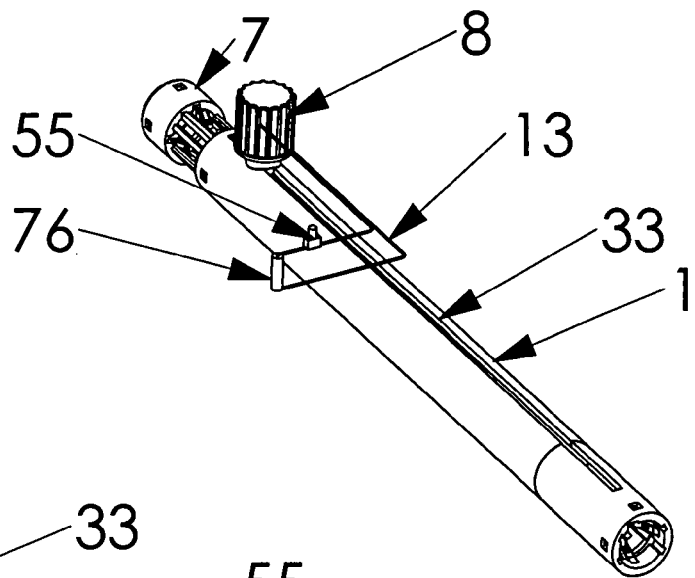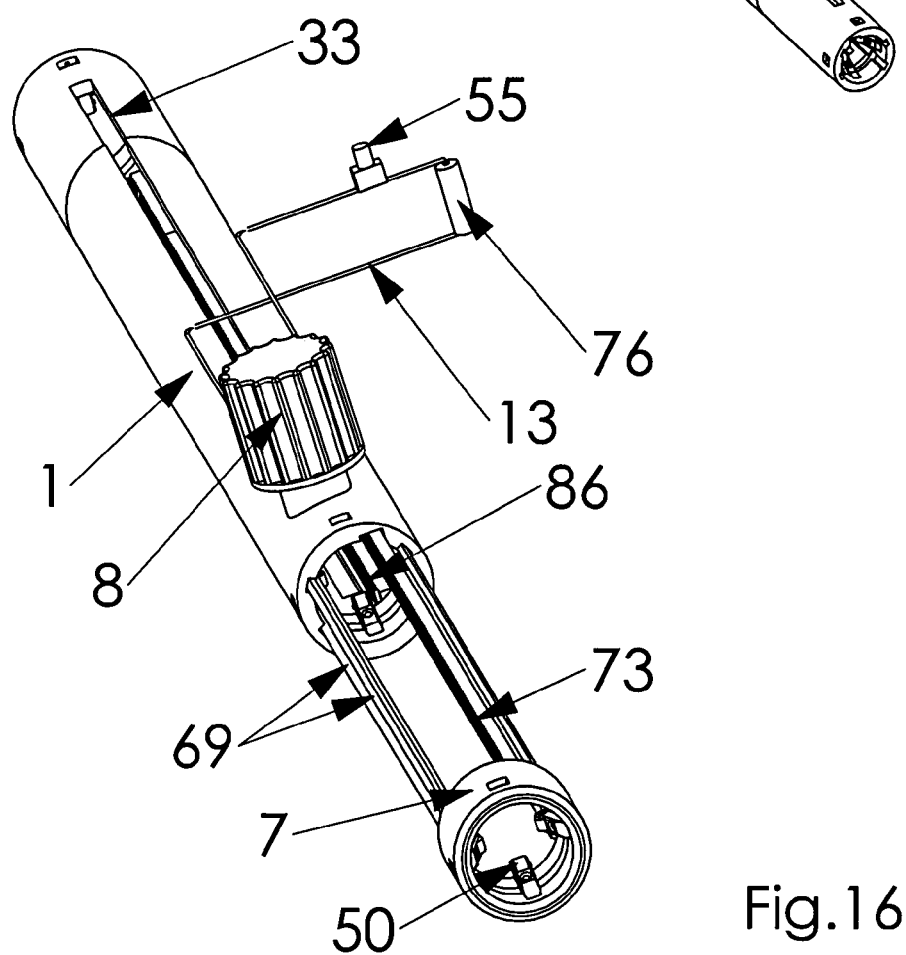

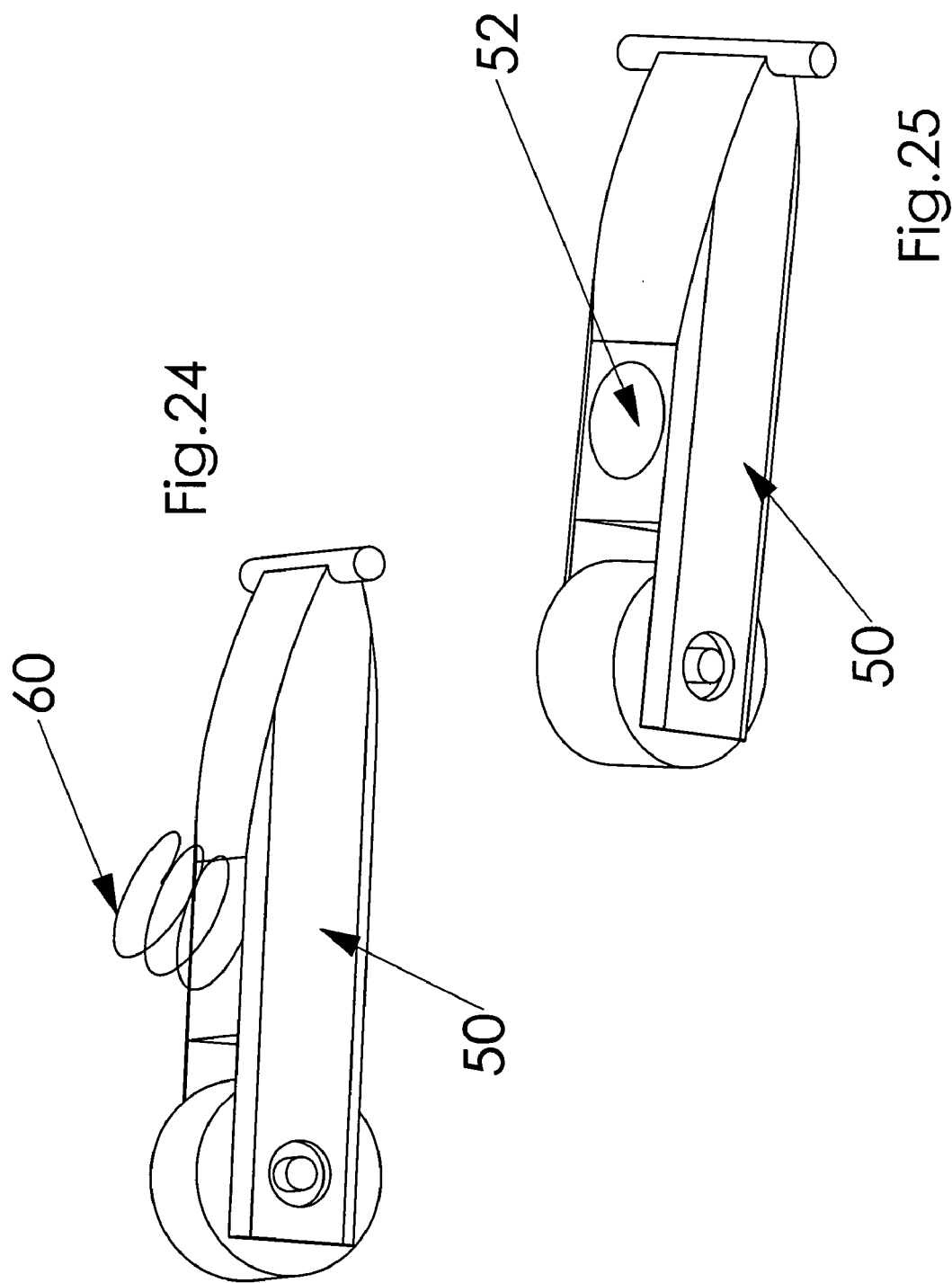

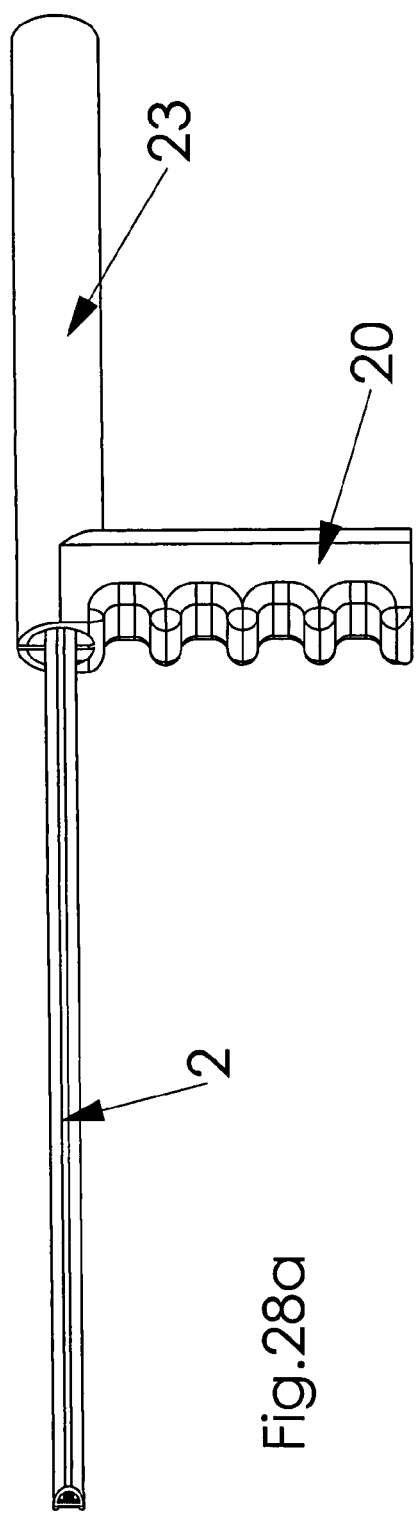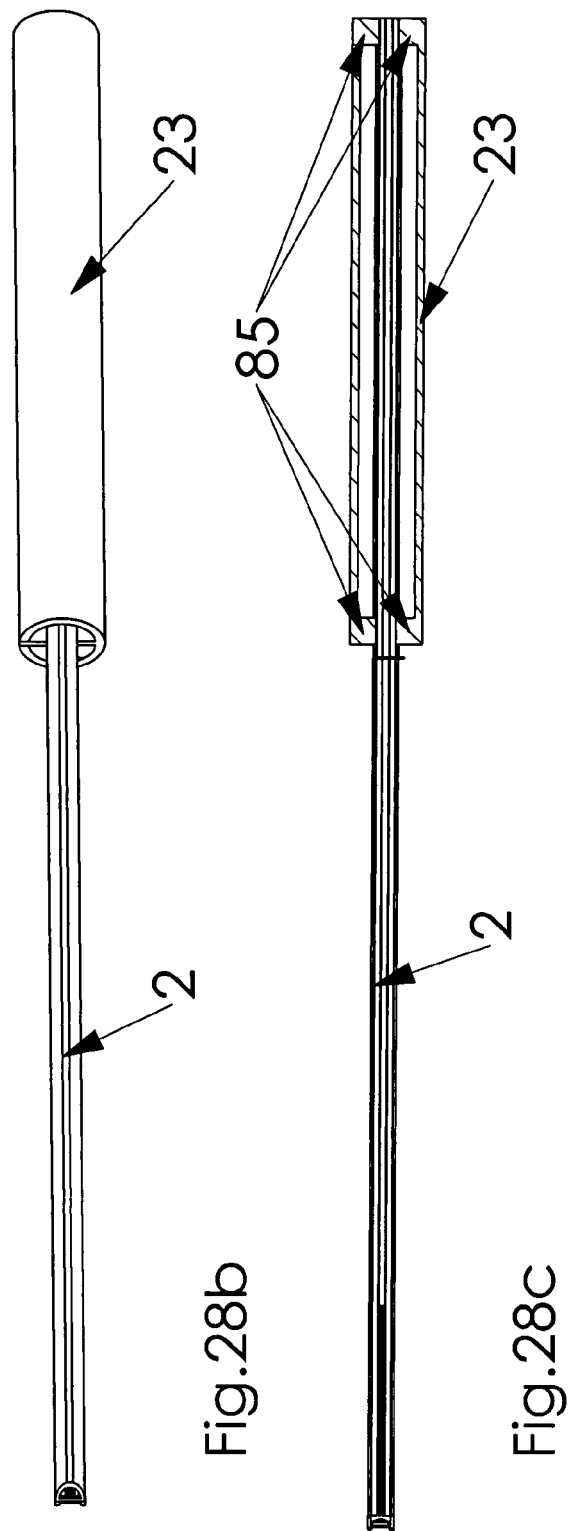
Fig.28a Fig.28b Fig.28c

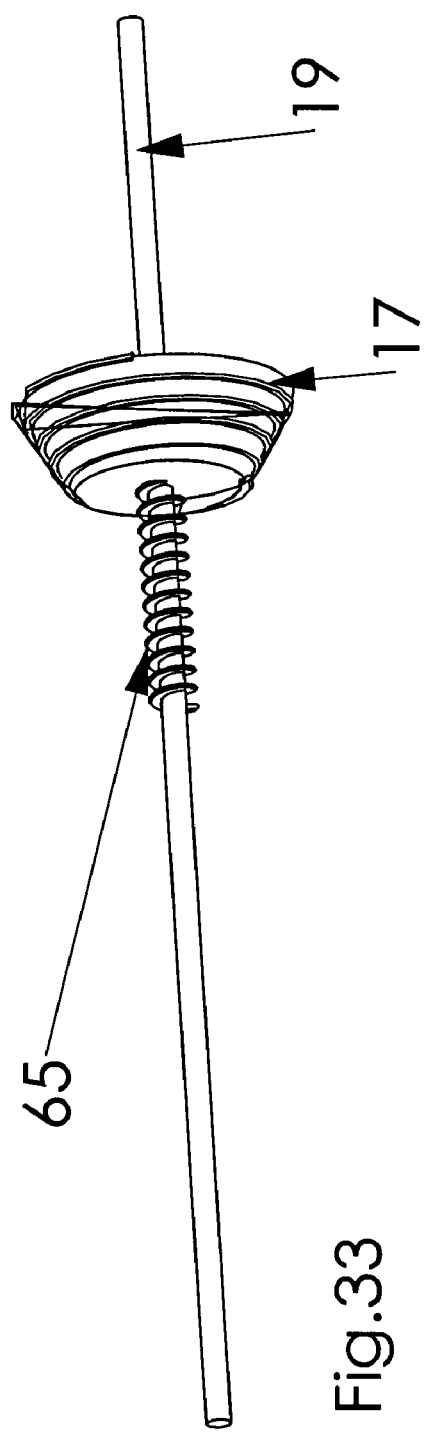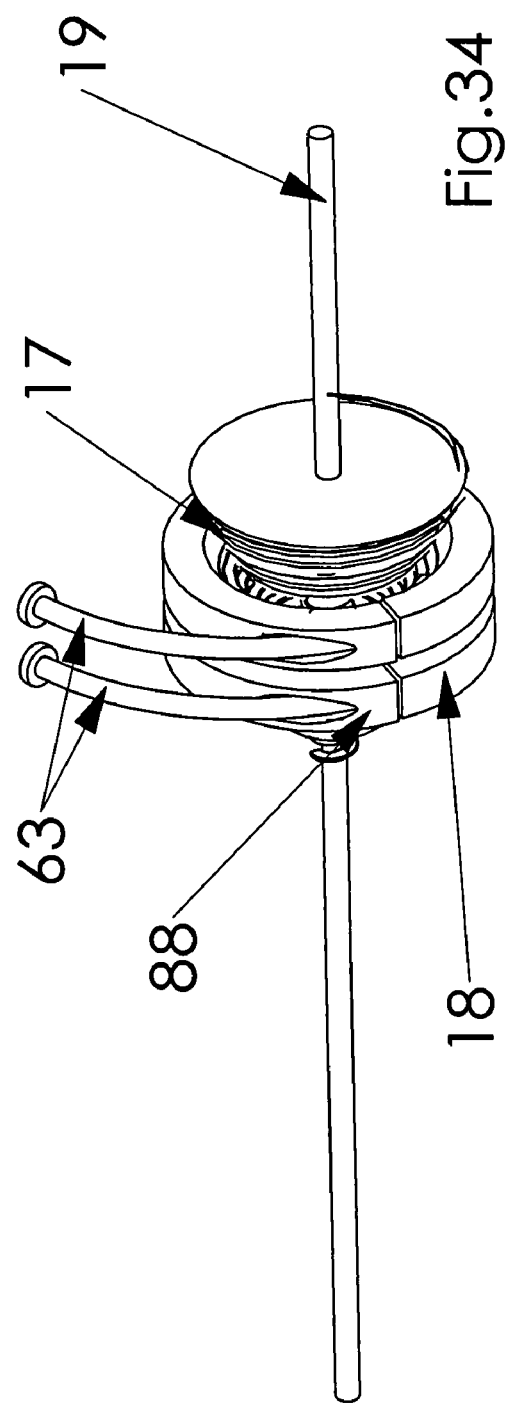

ENDOSCOPIC SYSTEM AND METHOD FOR THERAPEUTIC APPLICATIONS AND OBTAINING 3-DIMENSIONAL HUMAN VISION SIMULATED IMAGING WITH REAL DYNAMIC CONVERGENCE

CROSS-REFERENCES TO RELATED APPLICATIONS

None

BACKGROUND

1. Field of the Invention

This invention relates to the field of medical sensing and treatment devices, specifically to an endoscopic system and method that is adaptable for therapeutic applications as well as sensor/diagnostic operation and is capable of obtaining 3-dimensional human vision simulated imaging with real dynamic convergence, not virtual convergence. Applications may include use in any space with a limited-access opening, including but not limited to, intra-abdominal cavities, intra-thoracic cavities, and intra-cranial cavities. Non-medical applications are contemplated as well, including but not limited to search/rescue, scientific research, and investigative applications. The present invention endoscopic system comprises a main tubular shaft extending between two movable probe arms and a gearbox, and the hollow interior of the main tubular shaft provides the main pathway for the belts, electrical wiring, and cables needed to transfer power, sensor information, mechanical movement, and other information between the gearbox and the cameras, lights, positioning sensors, and diagnostic/sensor probes that are predominantly mounted on the distal ends of the two moveable probe arms. The probe arms can be moved toward and away from one another using a rotatable control on the gearbox that mechanically communicates with a two-rod control assembly positioned within the distal end of the main tubular shaft. Some of the movement-transmitting belts and gears in the present invention endoscopic system are also located within a moving cylindrical sheath that is positioned for movement back and forth on the main tubular shaft. The probe gear movement that increases or decreases convergence of the diagnostic/sensor probes at a majority of probe arm positions relates to movement of the moving cylindrical sheath, as further explained below. Movement of the main tubular shaft in any cavity toward or away from the target visual object causes linear movement of the moving cylindrical sheath (and the adjustment ring generally in fixed association with the moving cylindrical sheath) back and forth on the main tubular shaft to be transmitted into the gearbox where it is reduced in an appropriate ratio and then transmitted to the diagnostic/sensor probe gears (at the proximal ends of the cameras and other diagnostic/sensor probes), causing them to each turn on their axis and increase or decrease convergence of cameras/probes on their target object. Movement of the cameras (and other diagnostic/sensor probes requiring convergence for optimal use) independently from the moving probe arms, allows for convergence adjustment of diagnostic/sensor probe gears at a majority of probe arm positions, even when a target object close to the cameras is viewed. The proximal ends of the two probe arms are mounted for rotation on the same hinge at the distal tip of a main tubular shaft. Thus, probe arms are able to turn freely on the same axis from side-to-side within a 180 degree angle range of movement between a fully closed position (where they are located adjacent to one another) and a fully opened position (where they are approximately 180-degrees apart). Two or more diagnostic/sensor probes may be used at one time, and when this occurs at least two will be the same kind, with each same kind probe mounted onto a different probe arm. Diagnostic/sensor probes can include, but are not limited to, cameras, ultrasound devices, and other imaging probes. Further, convergence of diagnostic/sensor probes on a target object can be achieved via semi-automated means, or via a fully automated means using a plurality of belts and gears in addition to one size-adjustable gear. Semi-automated convergence is achieved using a pre-selected set of multiple gears having a predetermined ratio of convergence. In contrast, when high level of precision in convergence is needed in diagnostic, therapeutic, or other applications, a fully automated configuration is used where a computer continuously monitors positioning information from sensors, and then calculates any change needed in the ratio of convergence. If a change in the ratio of convergence for optimal viewing is needed, the computer will activate a motor and an electromagnet that work in concert to cause the size-adjustable gear to open or close accordingly so that an optimal ratio of convergence is continually provided. Provisions for automated convergence include the use of a computer, sensing means adapted to determine a target's distance from the distal end of the main tubular shaft, and additional sensing means adapted to provide information about probe arm positioning and the maximum arc of convergence for diagnostic/sensor probe gears relative to the target object so that the arc through which the diagnostic/sensor probes must move to achieve full range of convergence can be revealed. Although not limited thereto, an operator of the present invention may view the images produced by its cameras or other diagnostic/sensor probes via a 3-dimensional display device, for example a head mount, wherein each of the operator's eyes is sent the images from the camera and/or other diagnostic/sensor probe mounted on a different probe arm that corresponds to this eye (meaning left camera images are transmitted to the left eye and right camera images are transmitted to the right eye).

2. Description of the Related Art

Most prior art endoscopes employ a single camera or optic system that does not offer 3-dimensional imaging. Multiple lenses, prisms, fiber-optic fibers, and/or mirrors are typically used to achieve a variable focal state. The few endoscopes that do employ two or more optic systems typically have them positioned at short spaced-apart distances from one another, which offer their users limited depth perception at best. No endoscopes having multiple optic systems are currently known to provide dynamic convergence of their optic systems. Other 3-dimensional imaging devices that provide convergence do so in the form of virtual images created for operator viewing. Although virtual images are adequate in some applications, the greater clarity and precision of human vision simulated imaging is far superior to virtual image compilation, and desired. No other endoscopic system and method adaptable for therapeutic applications and/or sensor/diagnostic operation is known that functions in the same manner to provide real dynamic convergence, has the same flexibility in spaced-apart probe distance adjustment that facilitates probe use in a larger variety of applications and in different types of cavities or space while simultaneously giving its operator superior depth perception, or provides all of the other advantages of the present invention.

BRIEF SUMMARY OF THE INVENTION

The primary object of this invention is to provide an endoscopic system and method that is adaptable for diagnostic/sensor operation and capable of obtaining 3-dimensional human vision simulated imaging with real dynamic convergence, not virtual convergence. Another object of this invention is to provide an endoscopic system that is adaptable for therapeutic applications in addition to diagnostic/sensor operation. It is also an object of this invention to provide an endoscopic system and method that can be used in medical applications, as well as non-medical applications including but not limited to that involving viewing into areas inaccessible directly by the human eye such as when needed for search/rescue, scientific research, and investigative applications. It is a further object of this invention to provide an endoscopic system capable of having at least two similar or different diagnostic/sensor probes simultaneously on each probe arm. It is also an object of this invention to provide an endoscopic system that has provisions for automated convergence through use of a computer and a size-adjustable gear, in addition to semi-automated convergence that only uses a set of gears with a pre-selected ratio of convergence determined according to the application and no size-adjustable gear. Another object of this invention is to provide an endoscopic system that is durably constructed and made from materials able to withstand without premature deterioration the repeated sanitizing procedures required for body cavity insertions.

The present invention, when properly made and used, will provide an endoscopic system and method that is adaptable for therapeutic applications conducted at least in part with a probe or probes, as well as diagnostic/sensor operation using one or more probes, and is capable of obtaining 3-dimensional human vision simulated imaging with real dynamic convergence, not virtual convergence. Applications may include use in any space, including but not limited to, intra-abdominal cavities, intra-thoracic cavities, and intra-cranial cavities. Non-medical applications are contemplated, including but not limited to search/rescue, scientific research, and investigative applications that involve viewing into areas inaccessible directly by the human eye. Two or more diagnostic/sensor probes may be used, with at least two being the same kind, such as but not limited to, camera, ultrasound, and other imaging probes. The diagnostic/sensor probes needed for 3-dimensional vision are each mounted to the distal end of a different probe arm, with the proximal ends of the two probe arms both being attached to the same hinge on the distal tip of the main tubular shaft that allows the probe arms to turn freely on the same axis from side-to-side within a 180 degree angle range of movement on the distal end. The proximal end of the hollow main tubular shaft is secured to a gearbox, allowing it to carry cables, belts, and electrical wiring that transmit power and mechanical movement from the gearbox to the cameras, other diagnostic/sensor probes, lights, diagnostic/sensor probe gears, and probe arms, as well as sensory and diagnostic information from the diagnostic/sensor probes, positioning sensors, and device-to-target sensor back to the gearbox from which it can be forwarded as needed to a head mount, other display means, and/or a computer capable of calculating and implementing needed camera and other diagnostic/sensor probe movement to achieve an optimal ratio of convergence. A manual control connected to the gearbox is used to manually open and close the probe arms via mechanical communication with a two-rod control assembly that causes it to move forward or backward relative to the distal end of the main tubular shaft, whereby the two-rod control assembly (connected on its distal ends to the probe arms) moves into the main tubular shaft to open the probe arms and extends further beyond the distal tip of the main tubular shaft to close the probe arms. The main tubular shaft has an outer shell around its proximal end that can be used by an operator to hold the present invention device during its use. While the main tubular shaft is long and narrow, the outer shell is comparatively short and wide, typically being approximately one-third of the length of the main tubular shaft, although not limited thereto. The main tubular shaft and surrounding outer shell are fixed concentrically together by four radially-extending braces so that the outer shell cannot move independently from the main tubular shaft, with two braces used at the distal end of the outer shell and two braces used at the proximal end of the outer shell (located adjacent to the gearbox). In the alternative and as an option, a handle may be connected to the outer shell for improved operator handling of the present invention device. Between the distal end of the main tubular shaft and the outer shell secured to it, an adjustment ring and moving cylindrical sheath are temporarily fixed together for movement in unison, as well as joint movable association with the main tubular shaft. The adjustment ring is positioned to move between the main tubular shaft and the moving cylindrical sheath, with the proximal end of the moving cylindrical sheath guided during its movement into the outer shell by the radially-extending braces that secure the main tubular shaft to the outer shell. Movement of the diagnostic/sensor probes and the main tubular shaft into a cavity toward or away from a target object causes a corresponding movement (but in opposite direction) of the adjustment ring and the moving cylindrical sheath on the main tubular shaft (which is explained in detail later on), the movement of which is transmitted in multiple mechanical steps to the diagnostic/sensor probe gears to cause appropriate increase or decrease in convergence. The adjustment ring can be released from the moving cylindrical sheath for independent movement on its own when a control on the gearbox is manipulated and causes a pinion gear to disengage from a rack on the adjustment ring. Movement of the adjustment ring (without corresponding movement of the moving cylindrical sheath) allows the distal end of the main tubular shaft to move toward or away from a target object without initiating a diagnostic/sensor probe gear convergence action that would otherwise occur as a result of the linear movement of the moving cylindrical sheath. Strategically positioned controls, belts, gears, pulleys, cables, and springs can be used to mechanically transfer movement of the joined adjustment ring and moving cylindrical sheath to the gearbox, which is then reduced in semi-automated convergence applications through use of a set of multiple gears pre-selected to achieve a predetermined ratio of convergence, such as but not limited to 100:1.5 (where 100 mm of linear movement in the moving cylinder sheath corresponds to 1.5 mm of turning movement in the diagnostic/sensor probe gear convergence arc. Although the 100:1.5 ratio of convergence corresponds to calculation examples provided in the accompanying illustrations, different ratios of convergence can be used in other applications where endoscope components differ in size and shape. Thus, when a new application of the present invention is contemplated, the ratio of convergence needed for that application should be calculated in advance (as explained later in this invention disclosure) so that an appropriate set of multiple gears can be selected and installed during the invention's manufacture to accommodate the maximum target-to device distance one expects to encounter for that application. After the linear movement from the moving cylinder sheath is transmitted to the gearbox and reduced an appropriate amount by the selected set of multiple gears appropriate to the application, the reduced movement is then mechanically transmitted from the gearbox to the diagnostic/sensor probe gears in the probe arms and used for changing the convergence of the diagnostic/sensor probes or therapeutic devices in a manner that allows for better target object surveillance and scrutiny. However, when more precision is required, a computer can be connected to the gearbox of the present invention and also connected to additional sensors (on the probe arms and elsewhere) that send the computer continuous positioning information (relating at a minimum to shaft-to-target distance and the spatial relation of the same kind diagnostic/sensor and/or therapeutic device on one probe arm to the other) that the computer uses to frequently calculate and implement new ratios of convergence to maintain optimal convergence of the same kind diagnostic/sensors or therapeutic devices.

Thus, as the diagnostic/sensor or therapeutic devices at the distal end of the main tubular shaft are inserted along with it into a cavity (and precede it into the cavity), such as an abdominal cavity having a endoscopic port, the shaft and sensors slide easily through the endoscopic port but the adjustment ring is stopped from entering the cavity by the endoscopic port's external structure. Continued forward movement of the main tubular shaft into the cavity toward a target object after the adjustment ring has been stopped by the cavity opening, (when the moving cylindrical sheath and the adjustment ring are joined together for movement as one unit), causes movement of the adjustment ring on the main tubular shaft in a backward direction farther away from the diagnostic/sensor or therapeutic devices, and also causes backward movement of the moving cylindrical sheath. The backward movement of the moving cylindrical sheath is mechanically transmitted to a pinion gear secured to the main tubular shaft. The pinion gear, through a gear mounted on the same axle with it, causes a belt to move that transmits the amount of backward movement into the gearbox, where it is reduced by a selected set of multiple gears and thereafter is mechanically transmitted in multiple steps to the diagnostic/sensor probe gears that respectively turn each diagnostic/sensor probe or therapeutic device on its axis so as to increase the convergence of the attached diagnostic/sensor probes or therapeutic devices an amount appropriate to the closer diagnostic/sensor probe-to-target distance. In contrast, pulling the main tubular shaft away from the visual target being viewed causes the adjustment ring and the moving cylindrical sheath connected to it to spring and slide forward on the main tubular shaft (in a forward direction toward the diagnostic/sensor probes or therapeutic devices) via a spring attached between the proximal end of the moving cylindrical sheath and the main tubular shaft. The forward movement of the moving cylindrical sheath affects the previously mentioned gear on the main tubular shaft, with the movement ultimately being transmitted to the same set of multiple gears in gearbox that then reduces the linear movement of the moving cylindrical sheath according to a predetermined ratio of convergence appropriate to the application in the selected set of multiple gears in the gearbox. The reduced movement is then mechanically transmitted from the gearbox back to the gears of the diagnostic/sensor probes or therapeutic devices in the same manner used to transmit the backward movement of the moving cylindrical sheath discussed immediately hereinabove, which causes the gears for the diagnostic/sensor probes or therapeutic devices to each turn on its axis and decrease the amount of convergence on the particular structure or object being viewed. One or more channels can be built into and along the length of this invention to allow the concurrent introduction and use of one or more independent instruments inside the cavity where the device is inserted. Independent instruments can include, but are not limited to, endoscopic scissors, graspers and biopsy forceps.

The description herein provides preferred embodiments of the present invention but should not be construed as limiting its scope. For example, variations in the length and diameter dimensions of the outer shell, the length and width dimensions of the gearbox, the configuration of the sets of multiple gears used in the gearbox to achieve a ratio of convergence appropriate to an application for real dynamic convergence, the length of the probe arms, the types of sensors or treatment devices secured to the probe arms, and the type of materials from which the main tubular shaft, moving cylindrical sheath, or any other component of the device are made as long as they are able to fulfill their intended functions, other than those shown and described herein, may be incorporated into the present invention. Thus the scope of the present invention should be determined by the appended claims and their legal equivalents, rather than being limited to the examples given.

BRIEF DESCRIPTION OF THE SEVERAL VIEWS OF THE DRAWINGS

FIG. 9 is an enlarged view of a diagnostic/sensor probe in the most preferred embodiment of the present invention and the probe gear used for its movement relative to the probe arm upon which it is mounted.

FIG. 10 is a top view of the two diagnostic/sensor probes in the most preferred embodiment of the present invention in their fully closed position.

FIG. 15 is a perspective view of the moving cylindrical sheath and adjustment ring in the most preferred embodiment of the present invention, with a rotatable manual control positioned against the moving cylindrical sheath and a schematic representation of the rotatable manual control connected via electrical wiring to a switch 55 (which is shown larger in FIG. 3 and located on the side of the gearbox) and also to a power source (which may be housed in the gearbox, or not). The rotatable manual control is used for direct operator control of adjustment ring movement via a cone-shaped pinion gear engaging the adjustment ring's linear gear. However, the rotatable manual control also houses an electromagnet (or linear solenoid) in its core (as can be seen in FIGS. 17 and 18), with the electrical wiring that appears in the schematic representation to be connected to the rotatable manual control actually being connected to the electromagnet, which is used to physically disengage the pinion gear from the adjustment ring's linear gear and thereby reset the diagnostic/sensor probes by placing them back into the zero position where no convergence of the diagnostic/sensor probes can occur.

FIG. 16 is a perspective view of the most preferred embodiment of the present invention having the adjustment ring in a position where its end rollers are visible, the projection rods of the adjustment ring extend outwardly from the moving cylindrical sheath for enhanced visibility, and the same schematic representation of the rotatable manual control appearing to be connected via electrical wiring to a switch and a power source that are also shown in FIG. 15 (whereas it actually the linear solenoid within the core of the rotatable manual control to which the electrical wiring is connected, as previously explained in the discussion of FIG. 15 immediately hereinabove).

FIG. 19a is a perspective view of the adjustment ring in the most preferred embodiment of the present invention showing a first end.

FIG. 19b is a perspective view of the adjustment ring in the most preferred embodiment of the present invention showing the end opposed to that shown in FIG. 19a.

FIG. 20 also displays some of the internal structure that permits it to glide smoothly on the main tubular shaft while in close engagement with the adjustment ring.

FIG. 24 is an enlarged view of one of the rollers and its associated spring in the most preferred embodiment of the present invention.

FIG. 25 is an enlarged view of one of the rollers without a spring in the most preferred embodiment of the present invention.

FIG. 28a is a side view of the outer shell in the most preferred embodiment of the present invention secured to the main tubular shaft, and a handle secured to the outer shell.

FIG. 28b is a side view of the outer shell in the most preferred embodiment of the present invention connected to the main tubular shaft without a handle being present.

FIG. 28c is a sectional view of the outer shell in the most preferred embodiment of the present invention connected to the main tubular shaft via radially-extending braces positioned at both ends of the outer shell.

FIG. 33 is a side view of the rod having both uniform threading and uniformly increasing threading that engages the size-adjustable gear to open and close it.

FIG. 34 is a perspective view of the rod having both uniform threading and uniformly increasing threading in the most preferred embodiment of the present invention in a position adjacent to the size-adjustable gear shown in FIGS. 31, 32a, and 32b, prior to its engagement with the size-adjustable gear to force it into an opened position, with the size-adjustable gear also shown having no springs and in a fully closed position.

Figure 1:
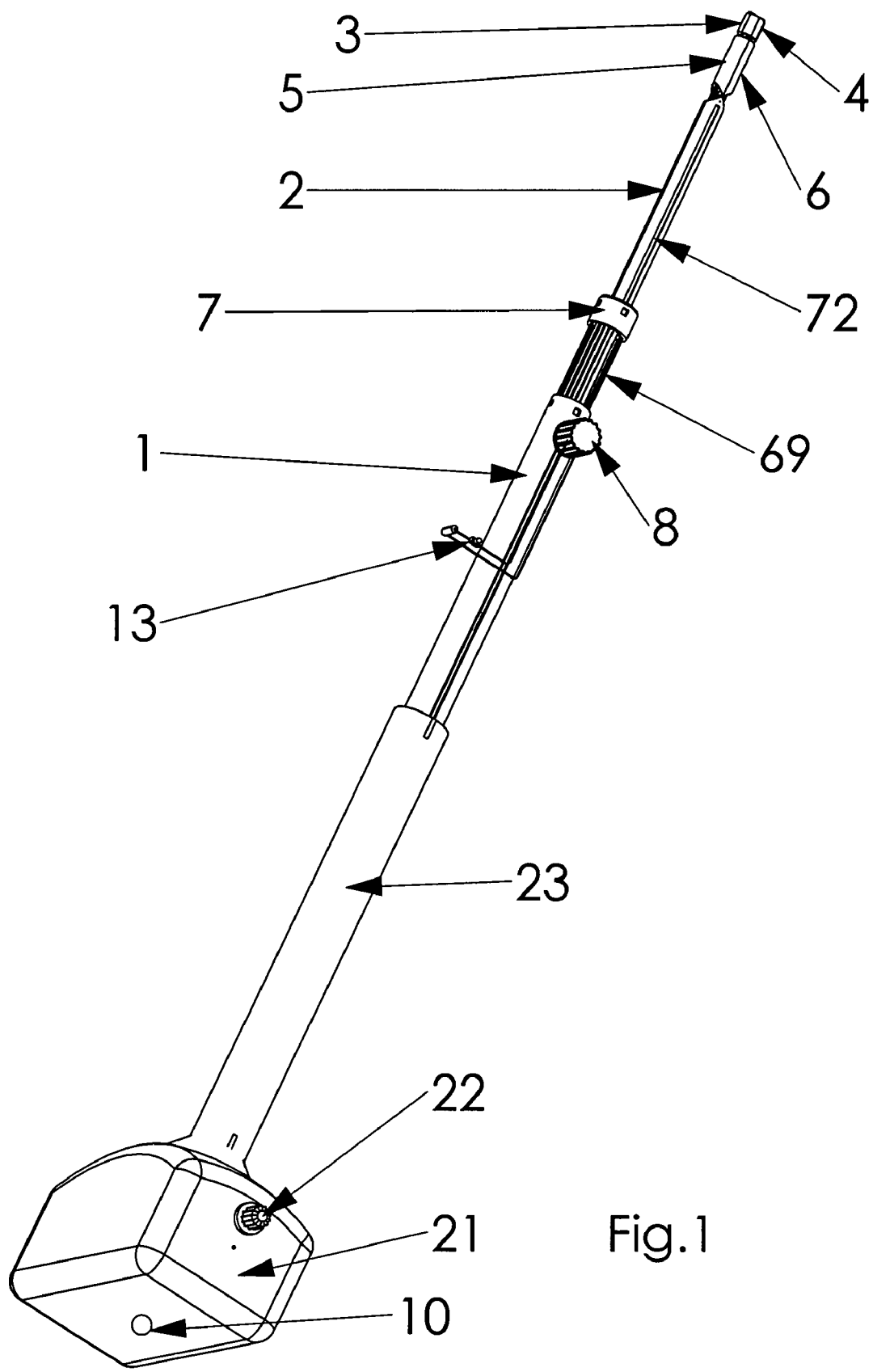
FIG. 1 is a perspective view of the most preferred embodiment of the present invention having two diagnostic/sensor probes mounted on the distal end of a main tubular shaft system capable of providing 3-dimensional human vision simulated imaging with real dynamic convergence.
Figure 2A:
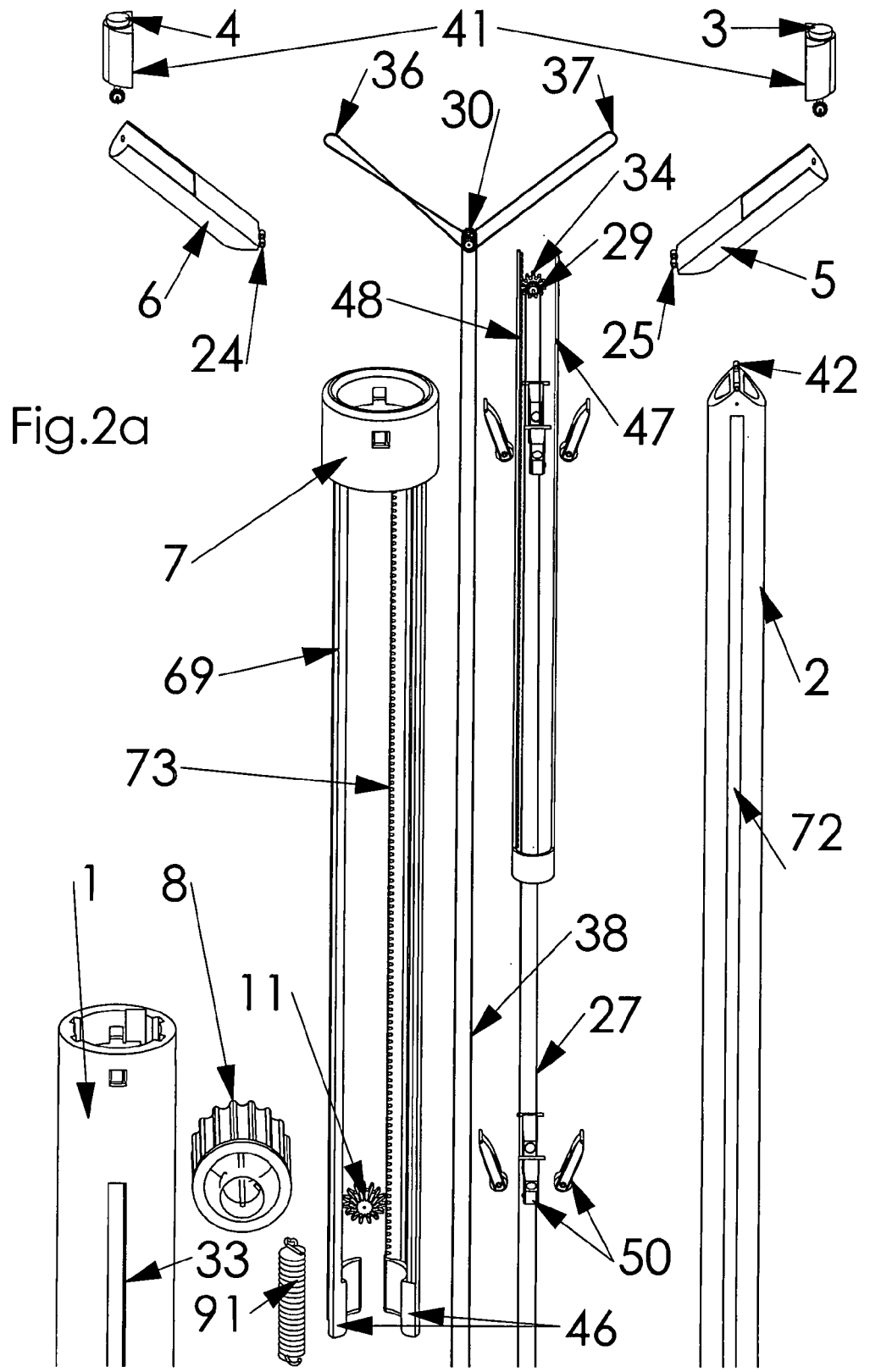
FIG. 2a is the first part of an exploded view of the most preferred embodiment of the present invention with diagnostic/sensor probes removed from their respective probe arms, the adjustment ring separated from the moving cylindrical sheath, the manual control for the adjustment ring separated from the moving cylindrical sheath, the belts and gears used for diagnostic/sensor probe movement and convergence exposed, and the main tubular shaft set apart from the probe arms.
Figure 2B:
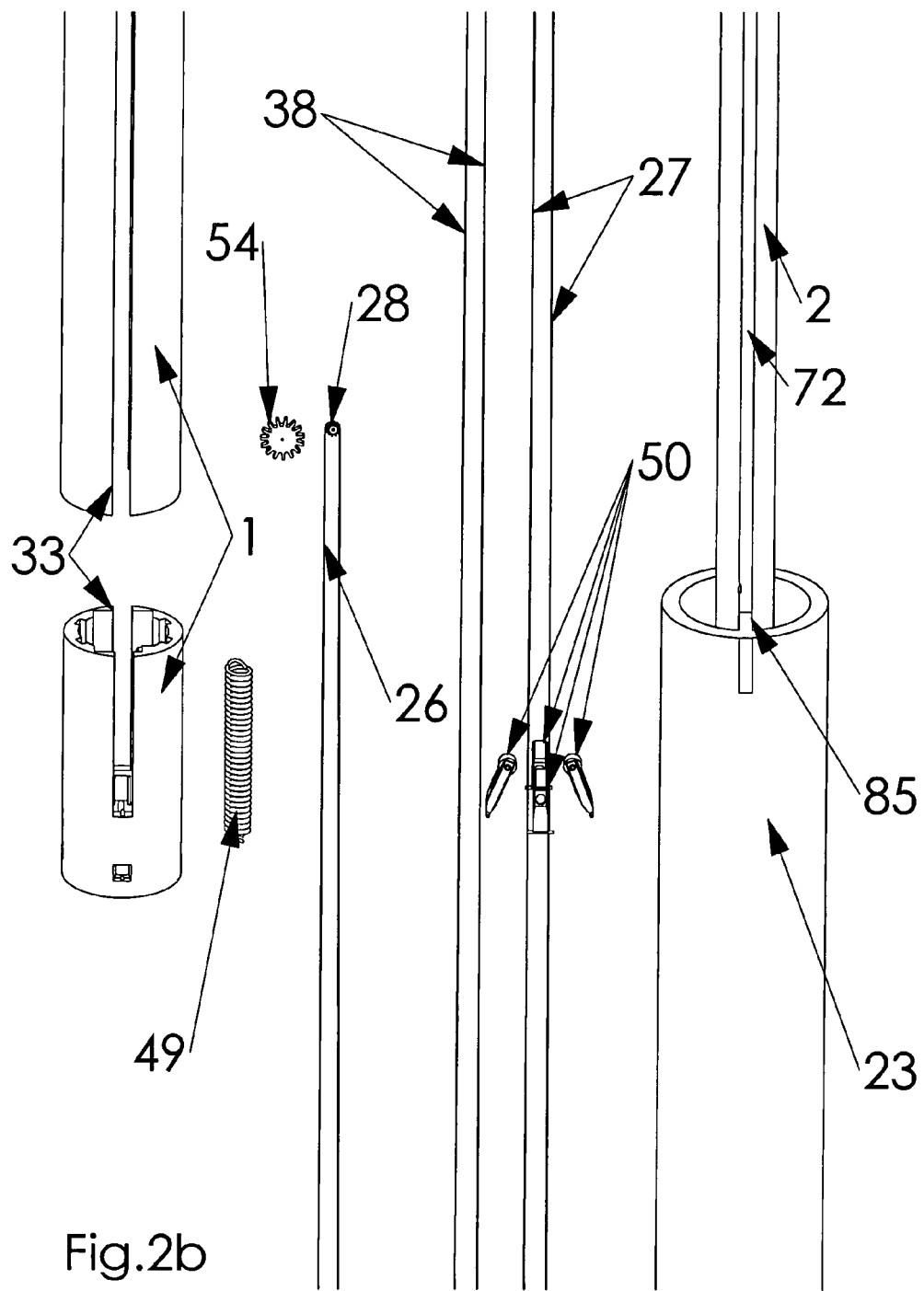
FIG. 2b is a continuation of the exploded view in FIG. 2a showing the middle portion of the most preferred embodiment of the present invention used for achieving real dynamic convergence, with the main tubular shaft shown on the right with its attached outer shell, two belts centrally located which transmit the movement of the moving cylindrical sheath to the gearbox shown in FIGS. 2c and 3, and from the gearbox to the diagnostic/sensor probe gears for increased or decreased convergence of same kind diagnostic/sensor or therapeutic devices on a target object, another belt that controls probe arm movement, and the lower end of the moving cylindrical sheath is shown on the left in two pieces with the bottommost piece revealing grooves that align the adjustment ring's projection rods and linear rack with the moving cylindrical sheath as they move on the main tubular shaft.
Figure 2C:
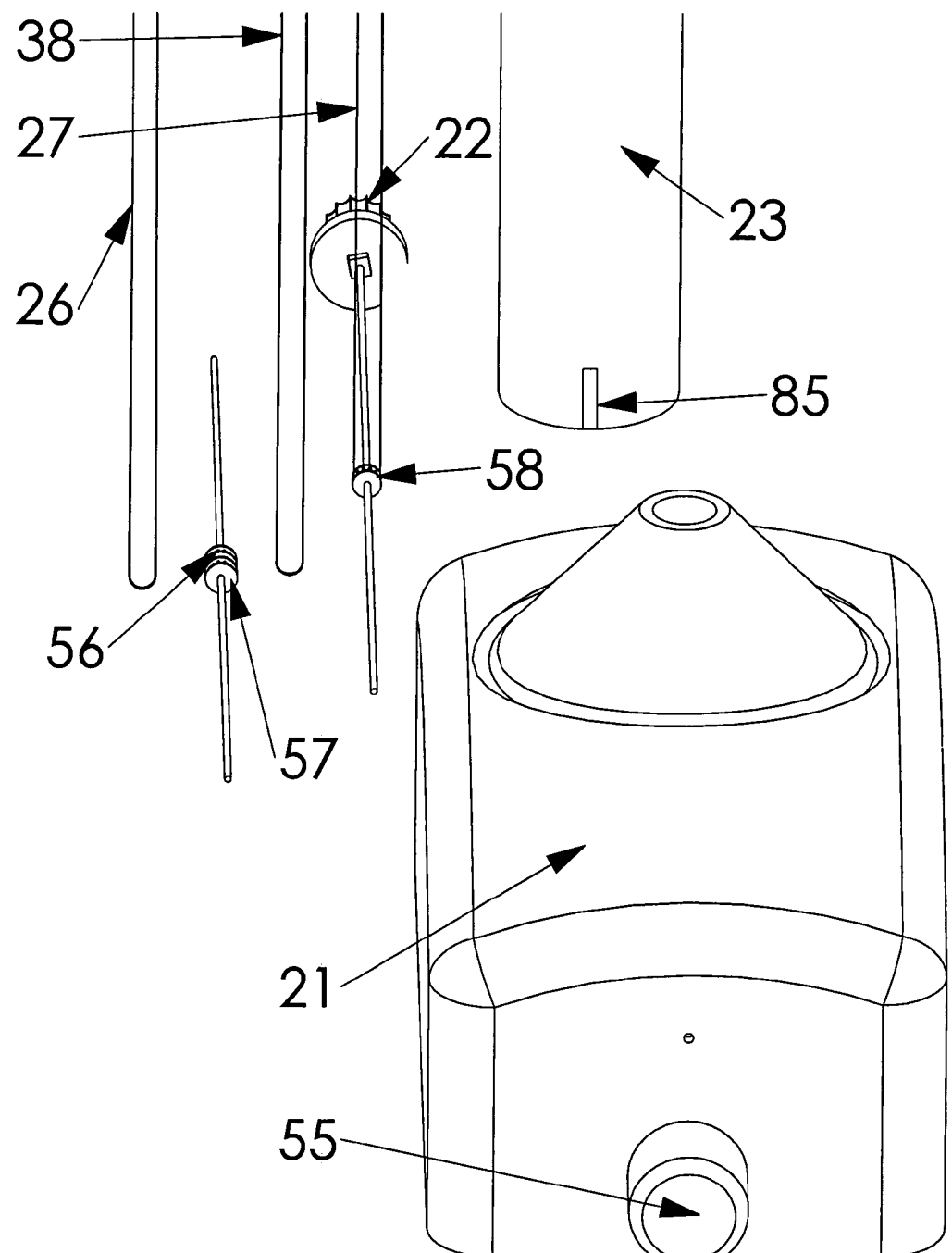
FIG. 2c is a continuation of the exploded view in FIGS. 2a and 2b showing the third part of the most preferred embodiment of the present invention with a gearbox illustrated on the right, which houses the set of multiple gears used in both semi-automated and fully automated configurations (pre-selected during manufacture according to the potential amount of convergence anticipated in an application and for clarity of illustration herein is represented only by a single gear) and also houses one or more size-adjustable gears (used only in the fully automated configuration and not shown in this view) that each work in the gearbox toward reduction of the incoming linear movement from the moving cylindrical sheath as it travels back and forth on the main tubular shaft (with the amount of the reduction in the semi-automated configuration directly proportional to the ratio of convergence pre-established for the set of multiple gears and the reduction ratio in the fully automated configuration changing continually according to updated information continuously received by a computer from positioning sensors to produce high precision convergence), with the reduced movement then being transmitted from the gearbox to the diagnostic/sensor probe gears that turn each diagnostic/sensor or therapeutic device on its axis so as to increase or decrease the convergence of the attached diagnostic/sensor or therapeutic devices the needed amount for optimal surveillance and scrutiny of a target object Also in FIG. 2c, the lower end of the outer shell to which the gearbox is connected is shown located above the gearbox (with the brace securing the outer shell to the main tubular shaft also being visible), two un-numbered axles and a rotatable control are shown to the left of the gearbox, and the lower ends of three belts and three gears are also shown to the left of the outer shell that help to transmit linear movement from the moving cylindrical sheath to the gearbox and after it undergoes the needed gearbox reduction mechanically transmit the reduced movement from the gearbox to the diagnostic/sensor probes for increasing or decreasing their convergence and also transmit the movement that controls opening and closing of the probes arms.
Figure 3:
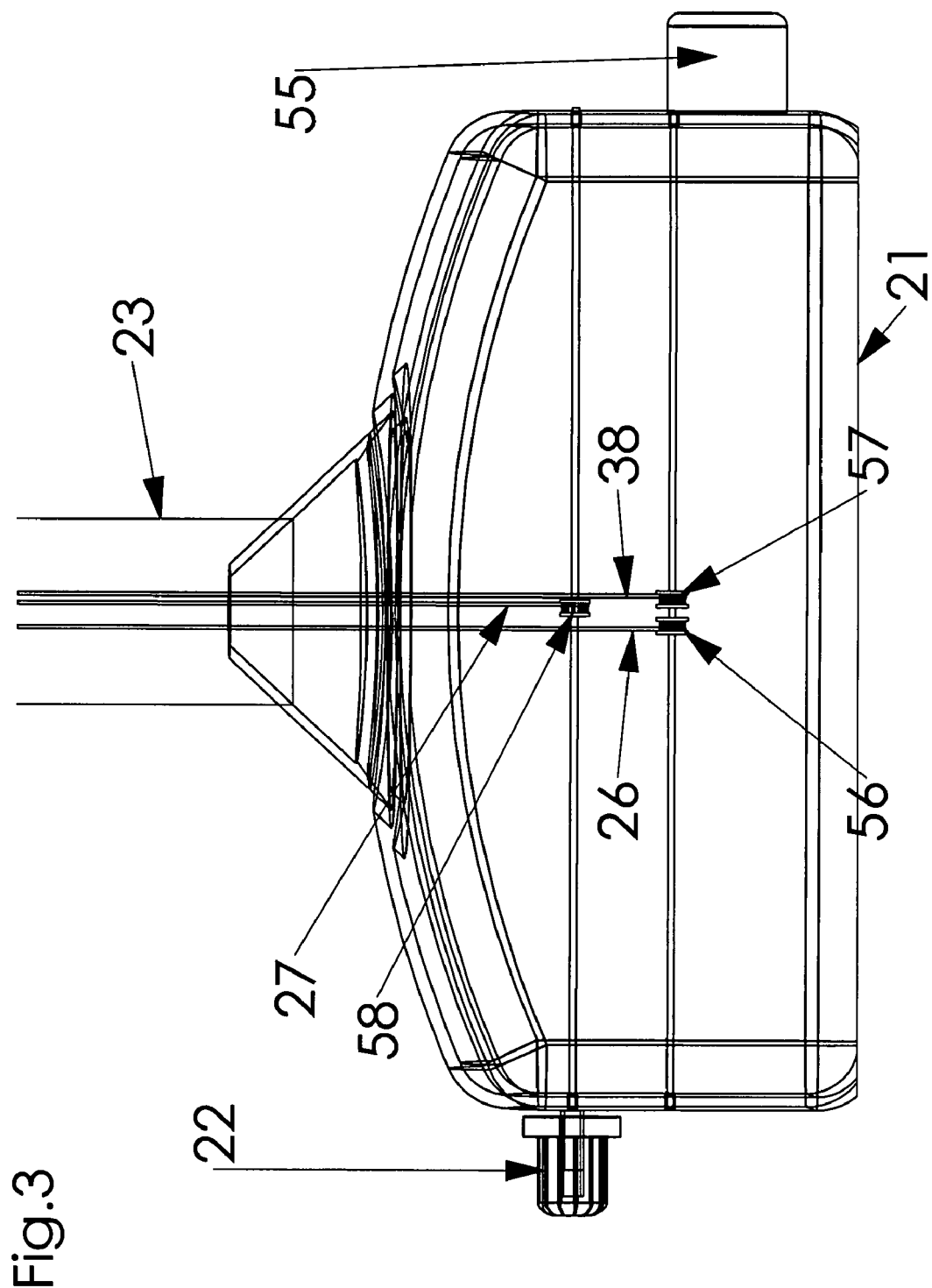
FIG. 3 is an enlarged view of the gearbox in the most preferred embodiment of the present invention having representative gears and belts configured for implementing diagnostic/sensor and therapeutic device movement, as well as probe arm movement, to achieve human vision simulated imaging with real dynamic convergence, and also having a manual control for opening and closing the probe arms and a reset switch that controls a linear solenoid that causes the gear system between the adjustment ring and the moving cylindrical sheath to become disengaged, wherein movement of the adjustment ring on the moving cylindrical sheath can occur without causing convergence of the diagnostic/sensor probes in certain situations that require that function.
Figure 17:
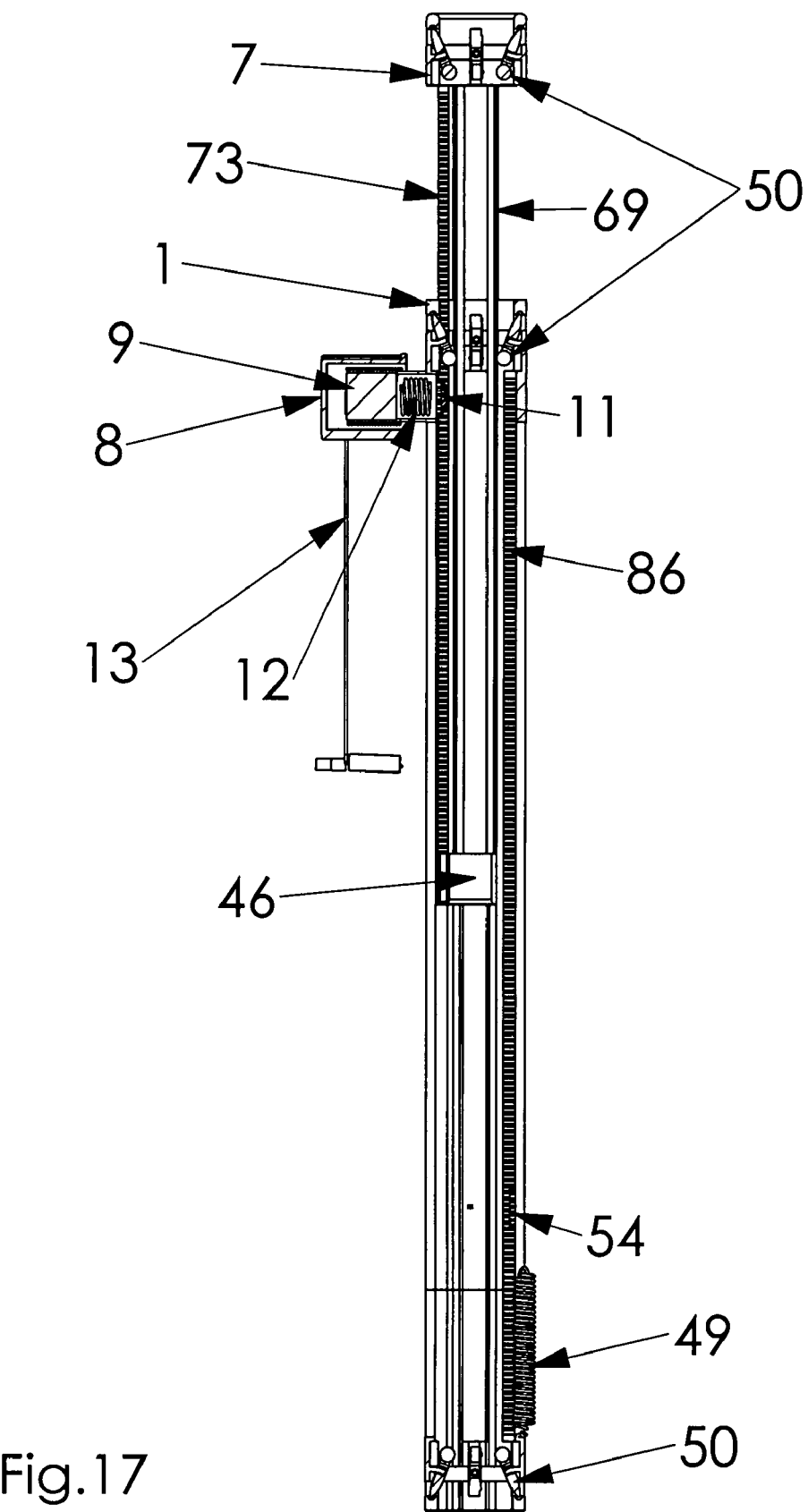
FIG. 17 is a sectional view of the most preferred embodiment of the present invention showing the adjustment ring extending outwardly from the moving cylindrical sheath, a linear solenoid housed within the rotatable manual control, and the linear solenoid connected to the electrical wiring, switch, and power source previously seen in FIGS. 15 and 16.
Figure 18:
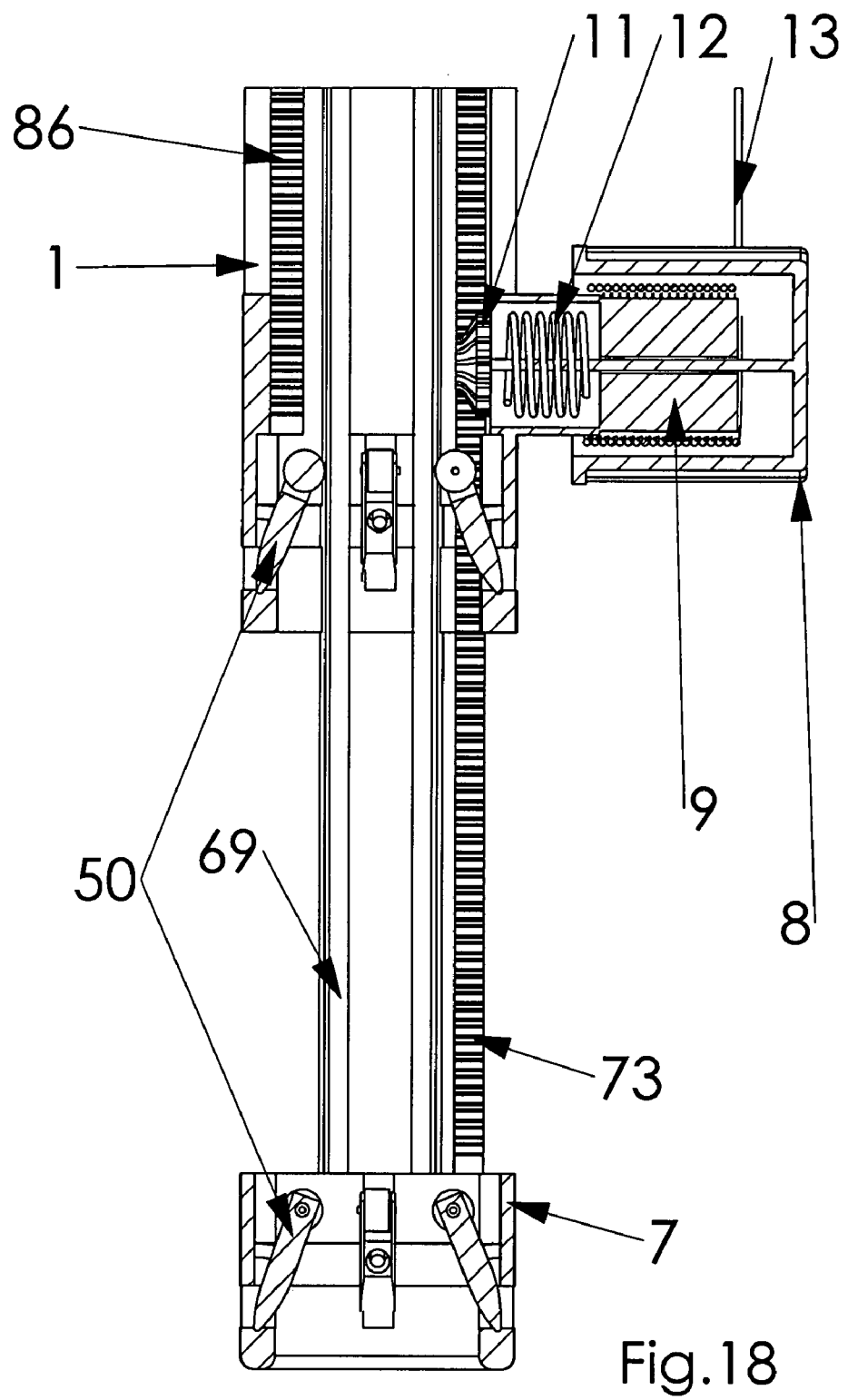
FIG. 18 is an enlarged sectional view of the most preferred embodiment of the present invention having a first set of four rollers associated with the distal end of the adjustment ring that provides smooth sliding movement between the adjustment ring and the main tubular shaft and a second set of four rollers associated with the distal end of the moving cylindrical sheath that provides smooth sliding movement between the moving cylindrical sheath and the main tubular shaft, with FIG. 18 also showing a rotatable manual control that is used for manual movement of a conical pinion gear along the linear gear of the adjustment ring for sliding movement of the adjustment ring back or forth on the moving cylindrical sheath as needed to manually control the increase or decrease of convergence occurring between the diagnostic/sensor probes on a visual target, with FIG. 18 further showing an electromagnet (also identified as a linear solenoid) housed within the rotatable manual control that when activated by the electrical switch and power source (visible in FIGS. 15-17) which are connected to the linear solenoid via electrical wiring disengage the conical pinion gear from the linear gear of the adjustment ring, thus allowing the adjustment ring to slide freely on the moving cylindrical sheath without causing any convergence of diagnostic/sensor or therapeutic probes.
Figure 29:
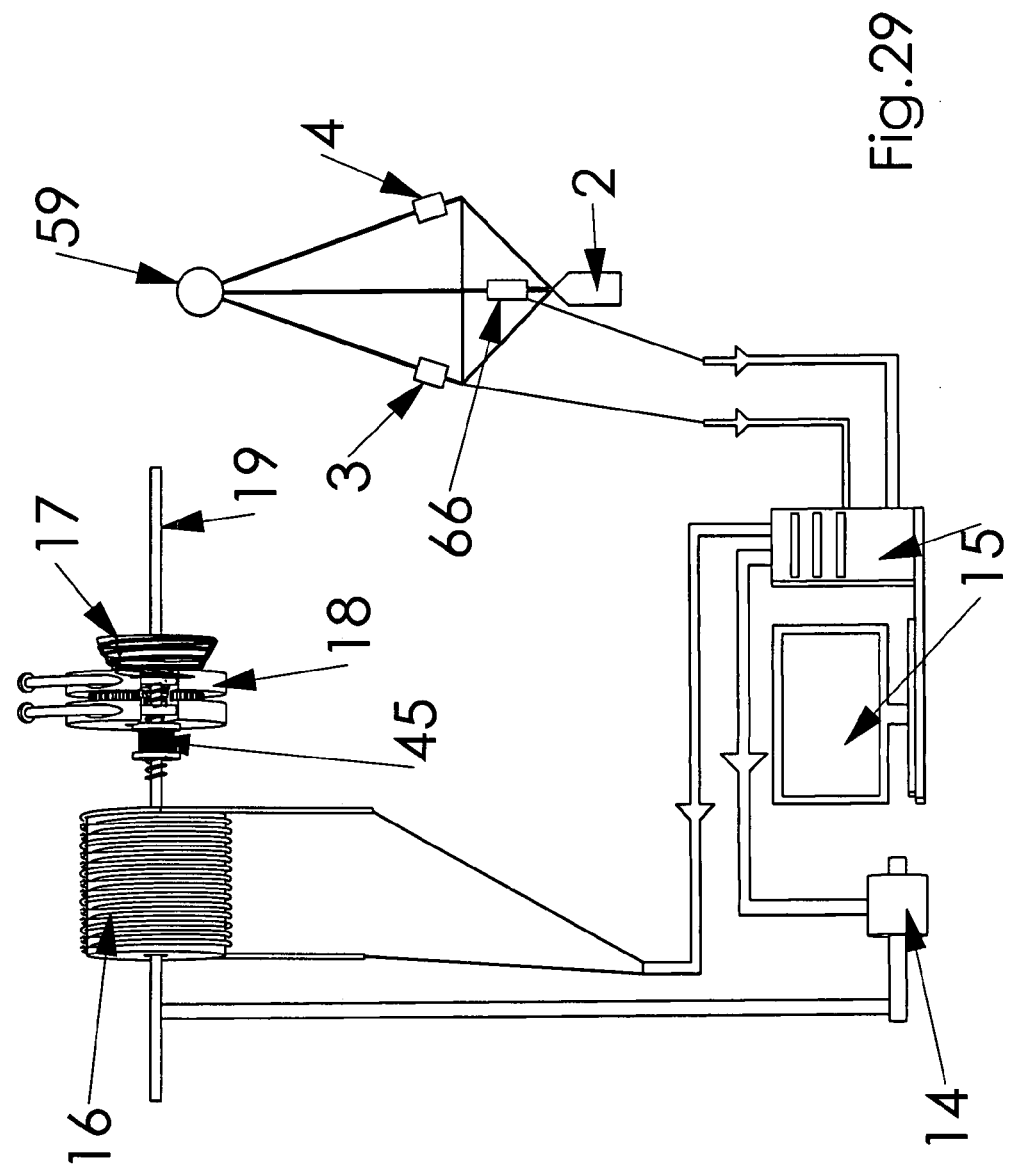
FIG. 29 is a schematic view of the fully automated configuration of real convergence achievable in the most preferred embodiment of the present invention when a very high level of accuracy for convergence is needed in certain applications, where two diagnostic/sensor probes of the same kind, positioning sensors on the probes arms, and a target distance sensor provide informational input to a computer, which causes a motor to open or close the size-adjustable gear in the gearbox that in combination with the multiple set of gears (also in the gearbox) changes the ratio of convergence exerted on the transmitted linear movement coming into the gearbox from the moving cylindrical sheath so that it can be reduced an appropriate amount, and the reduced movement is then mechanically transmitted from the gearbox to the diagnostic/ sensor probe gears to achieve increased or decreased convergence of the diagnostic/sensor probes on a target object. The change in the ratio of convergence in this fully automated configuration is a dynamic process that continues to change during use of the device, in response to changes in positioning received by the computer from the said sensors, and even though the change needed in the ratio of convergence is determined to be minimal to negligible, and not necessary in the majority of the regular routine applications (where the semi-automated configuration with its predetermined average ratio of convergence can be easily substituted without adverse impact), this very slight change could still be important in certain applications where a very high level of accuracy in convergence is required.

LIST OF COMPONENTS 1. moving cylindrical sheath [see FIGS. 1, 2a, 2b, 16, 17, 18, 20, 21, 26]
2. main tubular shaft [see FIGS. 1, 2a, 2b, 4, 5, 6, 7, 11, 12, 13, 14, 23, 26, 28a, 28b, 28c, 29, 30]
3. first diagnostic/sensor probe, in the alternative this also can be a therapeutic probe (including but not limited to therapeutic radiation probes, non-medical radiation devices, laser probes, radio-frequency probes) wherein the diagnostic/sensor imaging capability is accomplished via component # 40 [see FIGS. 1, 2a, 5, 6, 7, 9, 10, 11, 12, 13, 14, 29, 30]
4. second diagnostic/sensor probe, in the alternative this also can be a therapeutic probe (including but not limited to therapeutic radiation probes, laser probes, radio-frequency probes) wherein the diagnostic/sensor imaging capability is accomplished via component # 40 [see FIGS. 1, 2a, 5, 6, 7, 10, 11, 12, 13, 14, 29, 30]
5. first probe arm [see FIGS. 1, 2a, 5, 6, 7, 11, 12, 30]
6. second probe arm [see FIGS. 1, 2a, 5, 6, 7, 11, 12, 13, 14, 30]
7. adjustment ring [see FIGS. 1, 2a, 11, 12, 13, 14, 15, 16, 17, 18, 19a, 23, 30]
8. rotatable manual control for adjustment ring positioning back and forth on the moving cylindrical sheath (#1) [see FIGS. 1, 2a, 15, 16, 17, 18, 20]
9. first electromagnet (also referred to as linear solenoid) [see FIGS. 17, 18, 20, 21]
10. aperture leading to optional channel used for the insertion of an independent instrument needed to manipulate the target object during use of the present invention
11. cone-shaped pinion gear that engages rack (#73) for the adjustment ring [see FIGS. 2a, 17, 18, 22]
12. spring to return pinion gear (#11) back to its original working position [see FIGS. 17, 18]
13. representation of electrical wiring to connect the electromagnet (#9) to an on-off switch (#55) and a power source (#76) [see FIGS. 1, 15, 16, 17, 18, 20, 22]
14. electric motor for fully automated convergence adjustment [see FIG. 29]
15. computer system for fully automated convergence adjustment [see FIG. 29]
16. second electromagnet (linear solenoid) for fully automated convergence adjustment [see FIG. 29]
17. uniformly increasing diameter threading [see FIGS. 29, 33, 34]
18. lower part of size-adjustable gear [see FIGS. 29, 31, 32a, 32b, 34]
19. rod having both uniform threading (#65) and uniformly increasing diameter threading (#17) [see FIGS. 29, 33, 34]
20. handle [see FIG. 28a]
21. gearbox [see FIGS. 1, 2c, 3]
22. control on gearbox (#21) for opening and closing of probe arms (#'s 5 and 6) [see FIGS. 1, 2c, 3]

Figure 4:
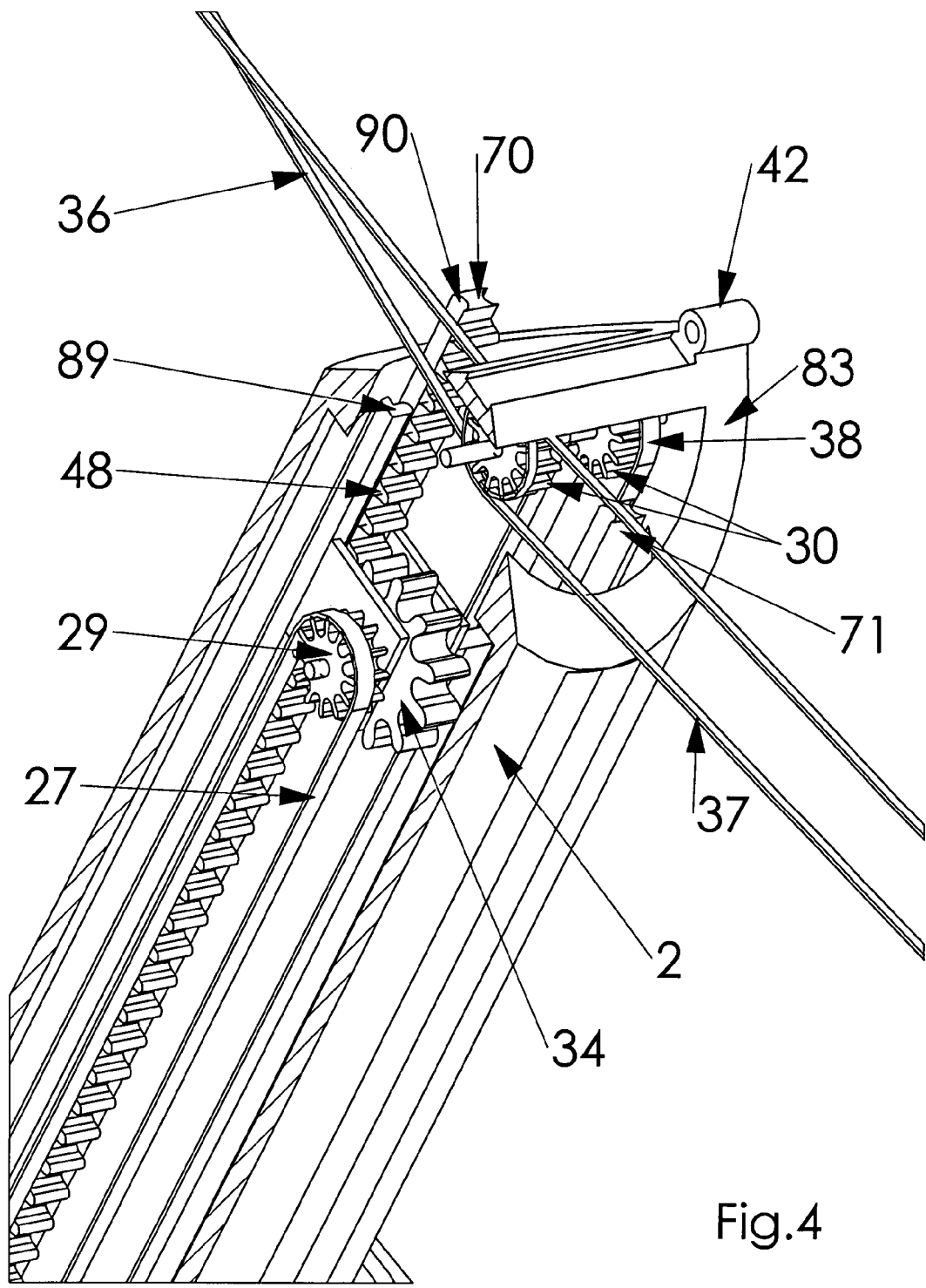
FIG. 4 is a sectional view of the top end of the main tubular shaft in the most preferred embodiment of the present invention having a hinge on the main tubular shaft for mounting probe arms, and a selection of gears, gear mounts, and associated belts, in addition to a rail guide.
Figure 5:
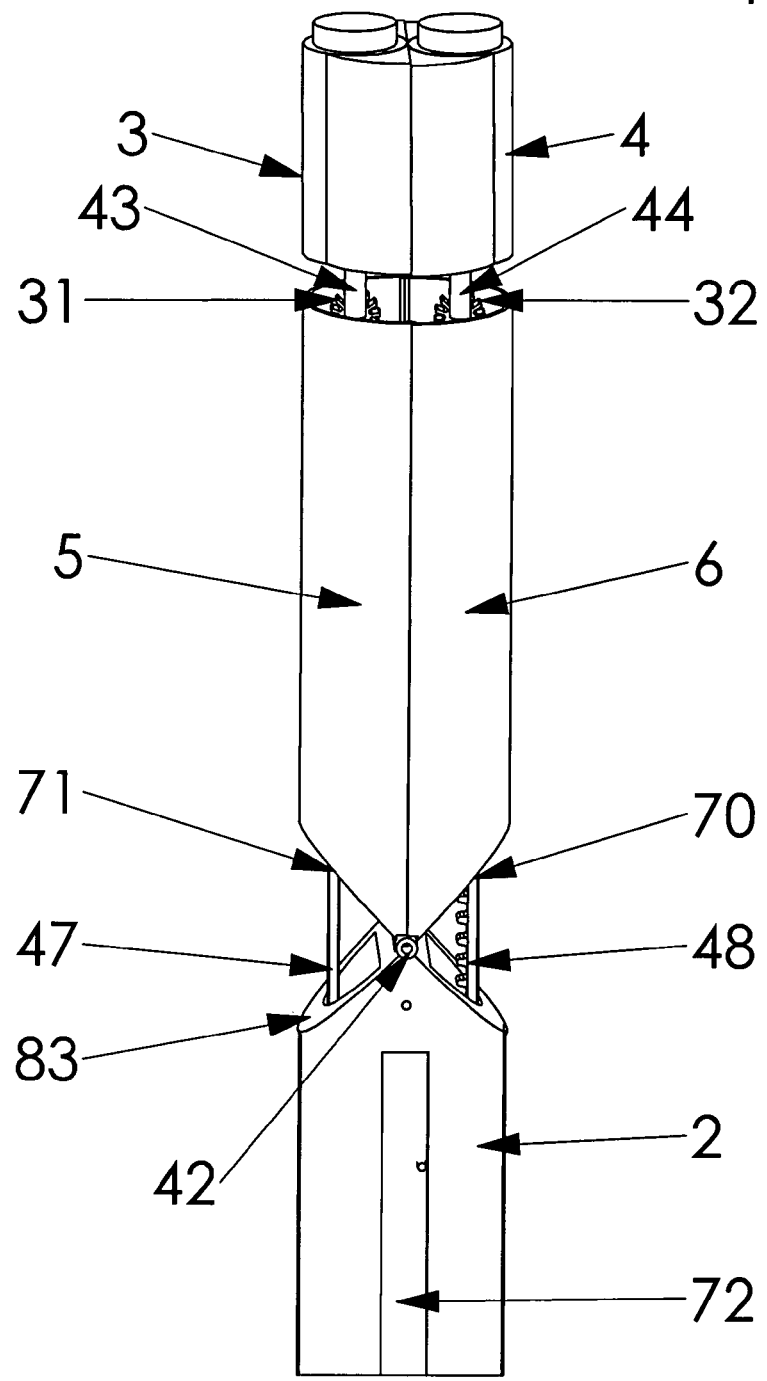
FIG. 5 is a side view of the most preferred embodiment of the present invention having two probe arms connected at their proximal ends to a hinge on the tip of the main tubular shaft, the probes in a closed position against one another and each having at least one diagnostic/sensor probe attached to its distal end.
Figure 11:
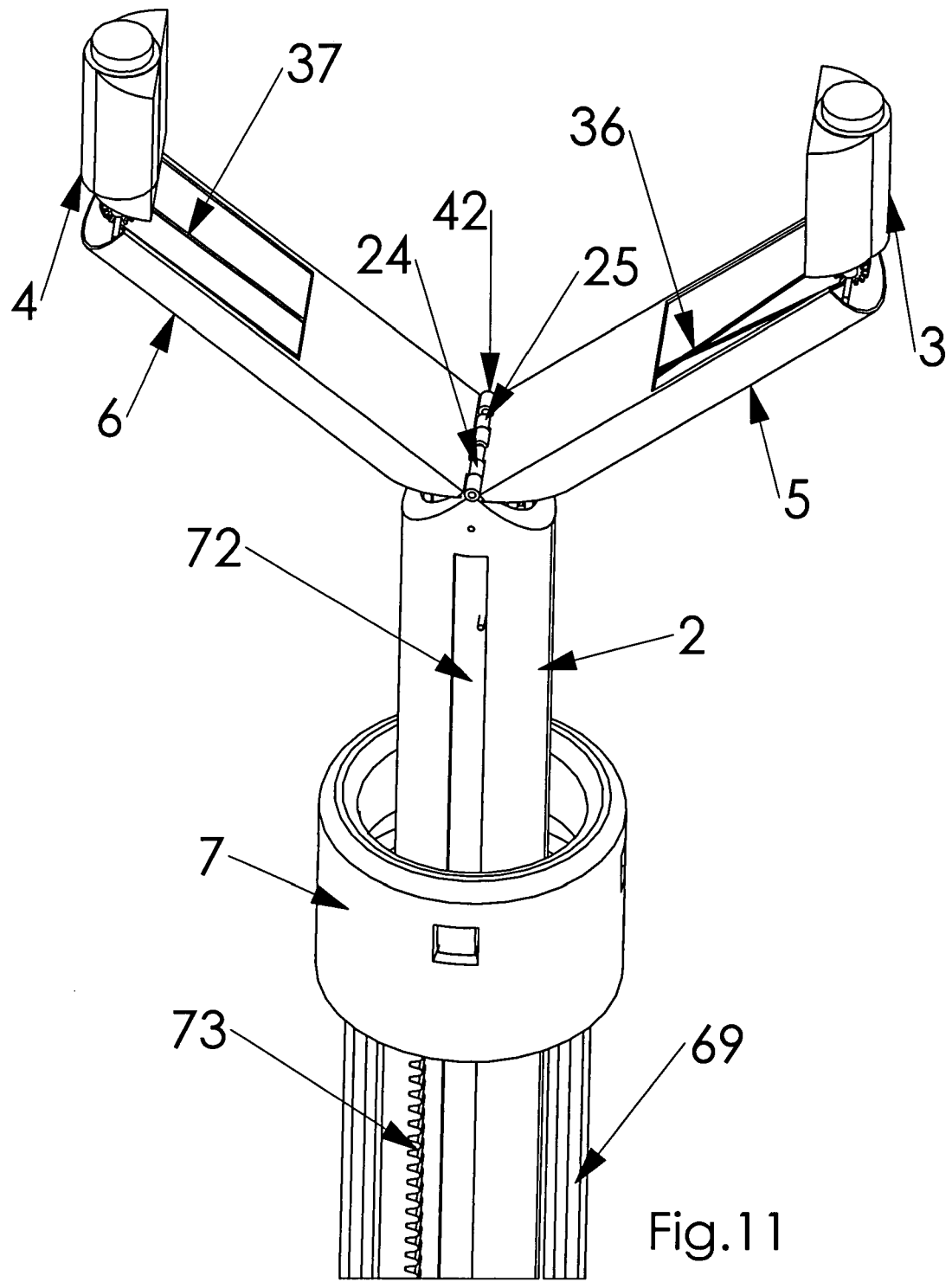
FIG. 11 is a perspective view of the diagnostic/sensor probes in the most preferred embodiment of the present invention displaying little or no convergence on a target object, the probe arms in a partially opened position, and with a portion of each probe arm removed to show the preferred internal positioning of the belts, the right one of which is crossed over on itself and the left belt forming a simple loop. (The ends of the probe arms remain open as shown so as to not limit diagnostic/sensor probe convergence movement, with a flexible covering protecting gear and belts from damage. In medical applications the covering must be able to withstand needed sterilization procedures.)
Figure 12:
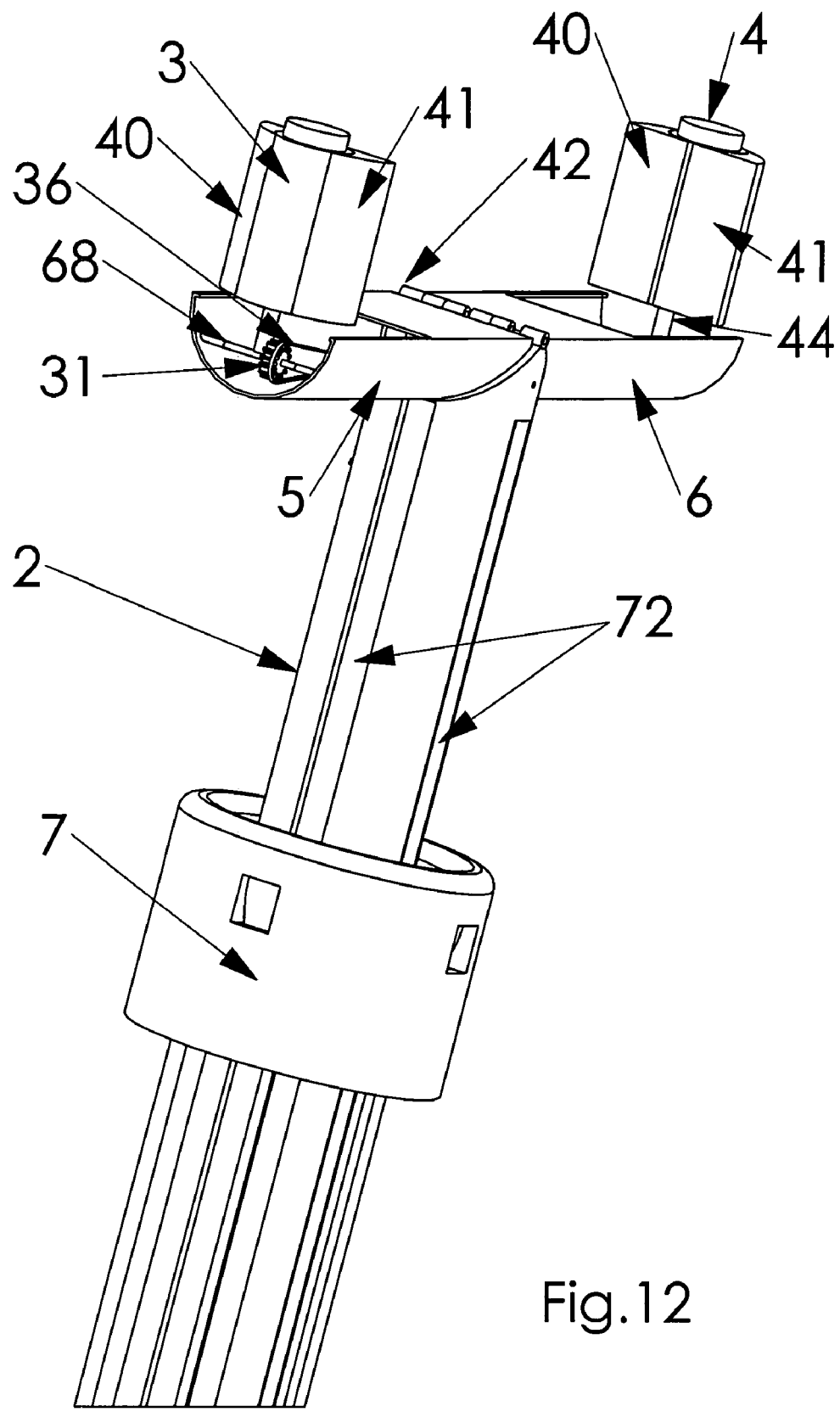
FIG. 12 is a perspective view of the diagnostic/sensor probes in the most preferred embodiment of the present invention displaying little or no convergence on a target object and with the probe arms in a fully opened position.
Figure 13:
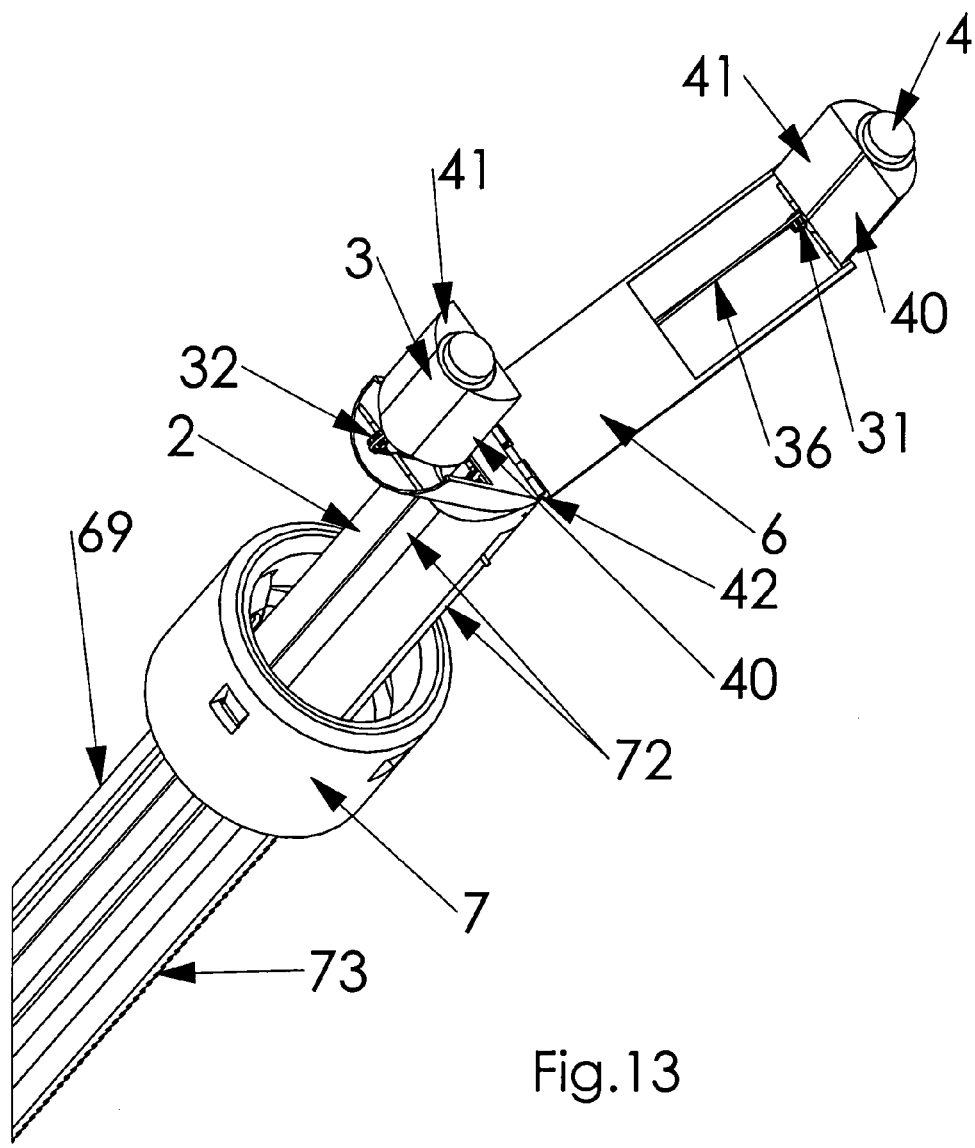
FIG. 13 is a perspective view similar to that in FIG. 11, but in a different viewing angle for better comparison to FIG. 14.
Figure 14:
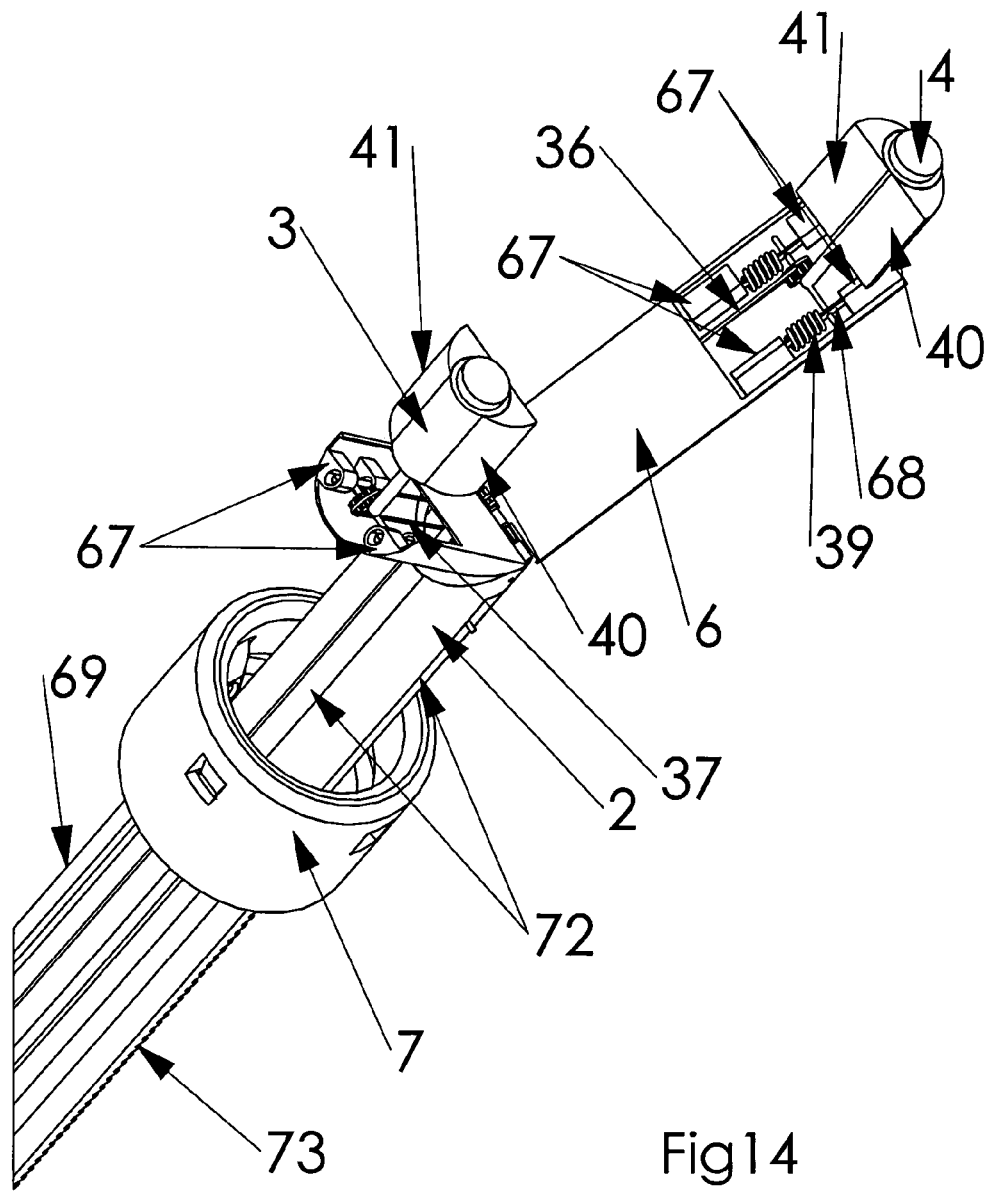
FIG. 14 is a perspective view of the diagnostic/sensor probes in the most preferred embodiment of the present invention that is similar to that shown in FIG. 13 with the probe arms in a partially opened position, but displaying an alternative means for mounting the diagnostic/sensor probes to the probe arms that connects each end of the probe gear's axle to a spring extending between two opposed mounts. This alternative mounting means would be used for both diagnostic/sensor probes even though only one in FIG. 14 includes it. Also, this configuration is used if the belts extending within the probe arms are made of non-stretchable materials, to compensate for the difference in the length of the belts required at different probe arm positions, and to also compensate for the probe arm structure that has probes arms turning on a different axis than the belts (the hinge on the tip of the main tubular shaft as opposed to the slightly lowered axis of the pair of gears positioned below the main tubular shaft hinge.
Figure 19:
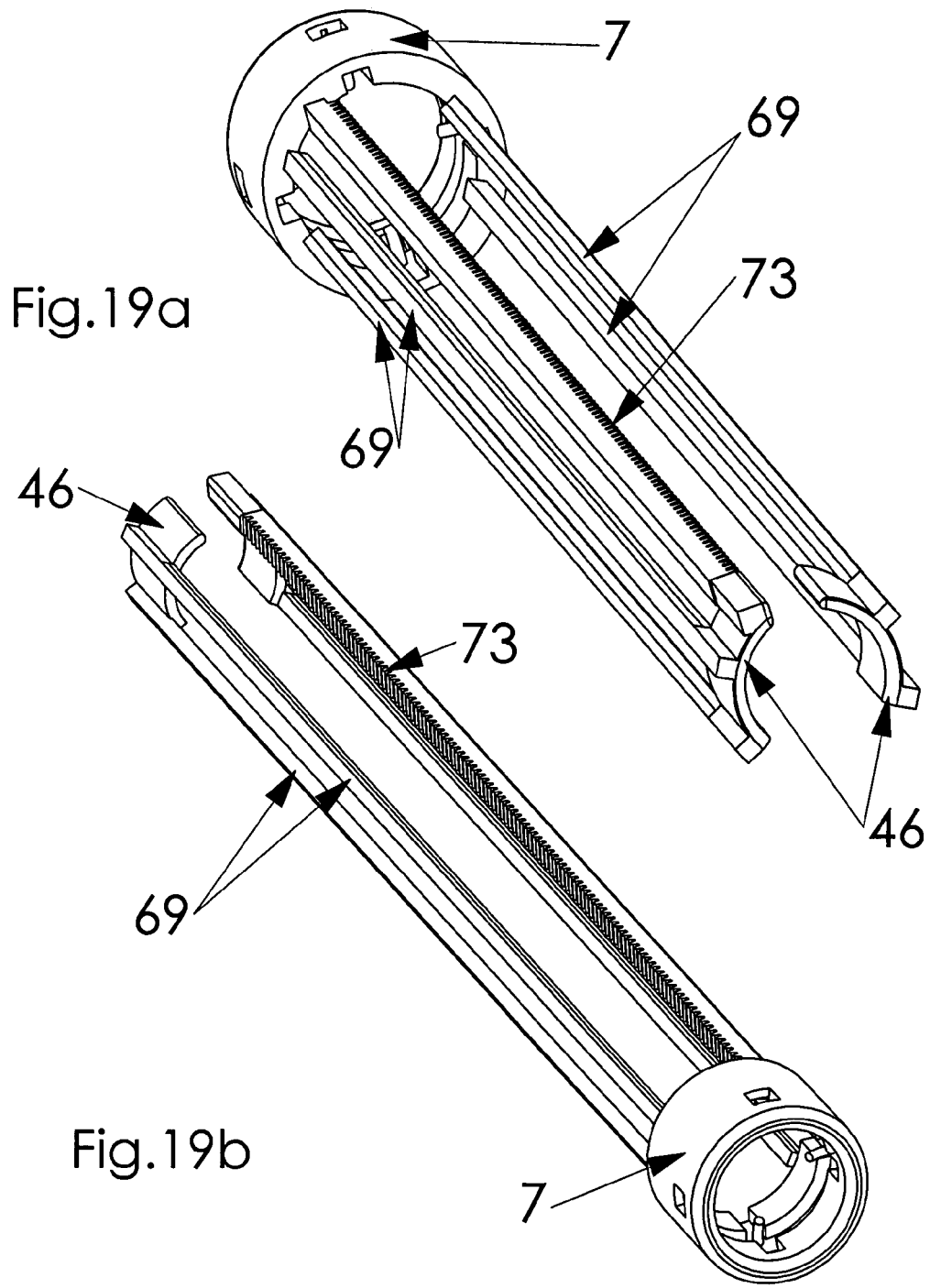
Figure 20:
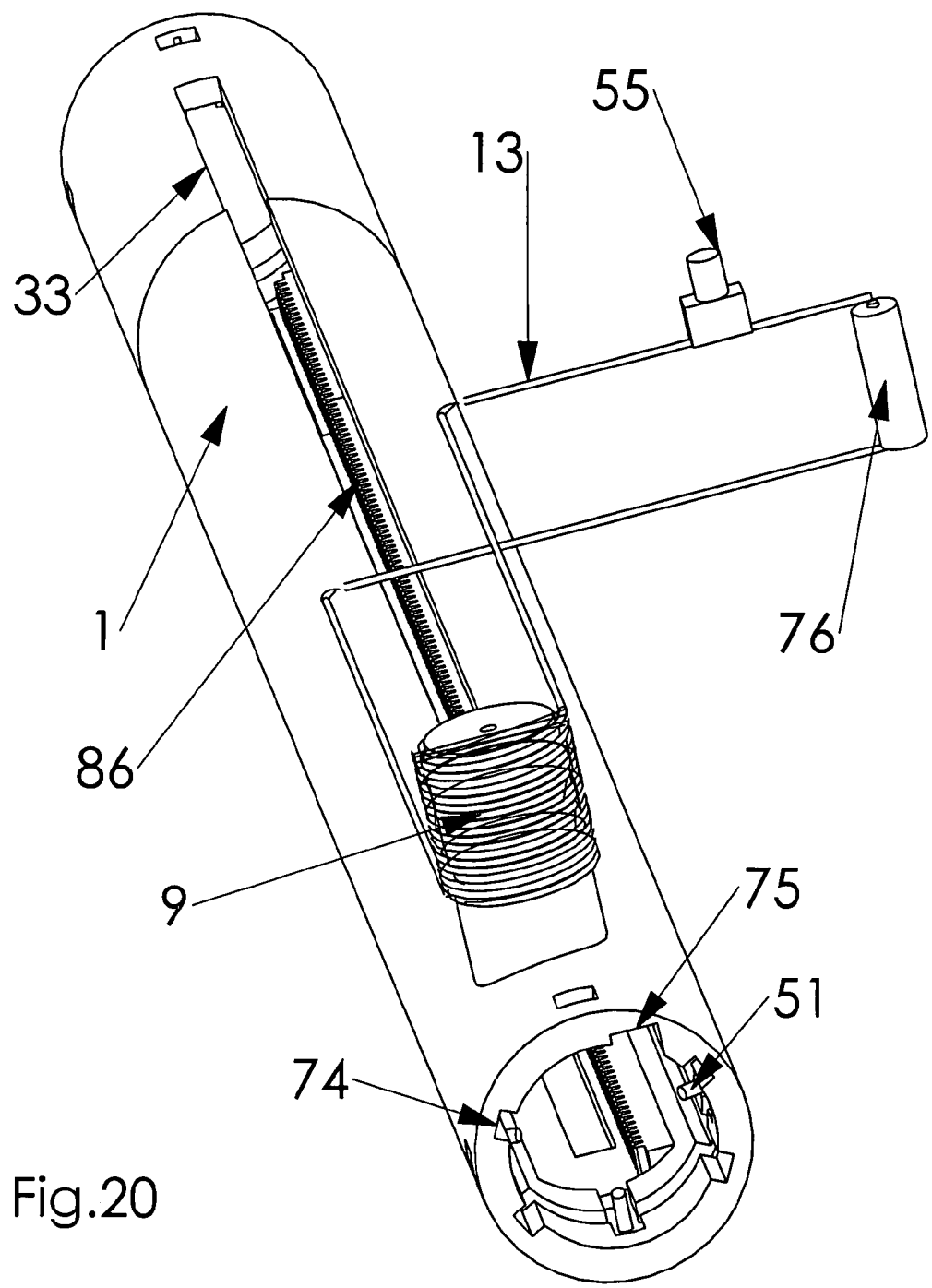
FIG. 20 is a perspective view of the moving cylindrical sheath in the most preferred embodiment of the present invention with the coils of an electromagnet housed within the rotatable manual control (used to manually increase or decrease the degree of convergence of the diagnostic/sensor probes on a visual target by manually moving the associated conical pinion gear engaged with the linear gear of the adjustment ring, but removed in FIG. 20 to expose the electromagnet) positioned against the outside surface of the moving cylindrical sheath and a schematic representation of the electrical wiring, switch, and power supply that are connected to the electromagnet for disengagement of the cone-shaped pinion gear from the linear gear of the adjustment ring as needed to allow the adjustment ring to slide freely back and forth on the moving cylindrical sheath without causing convergence (with FIG. 18 showing the spring that causes the cone-shaped pinion gear to again become engaged with the linear gear of the adjustment ring after electrical power to the electromagnet is turned off).
Figure 21:
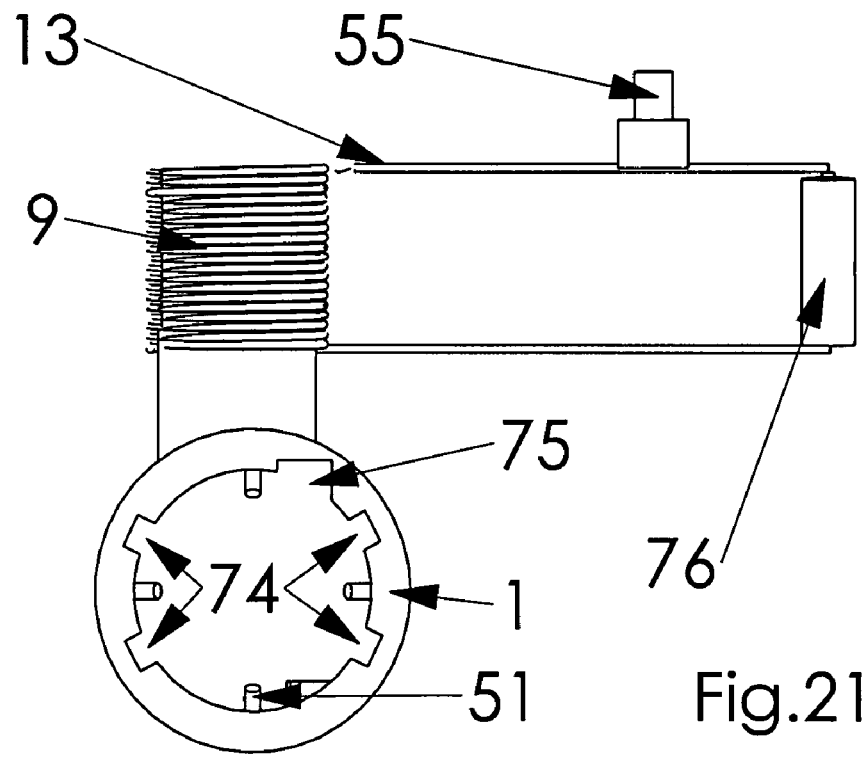
FIG. 21 is an end view of the moving cylindrical sheath in the most preferred embodiment of the present invention showing the groove for the adjustment ring's linear gear, multiple guides for the adjustment ring's four projection rods, and the moving cylindrical sheath's four arcuate rods each used for engagement with a roller and spring shown in FIG. 24, and further having a schematic representation of the coils of the electromagnet (linear solenoid) typically housed within the core of the rotatable manual control, as well as the switch, electrical wiring, and power source used for the activation of the electromagnet to cause the cone-shaped pinion gear to become disengaged from the adjustment ring's gear.
Figure 23:
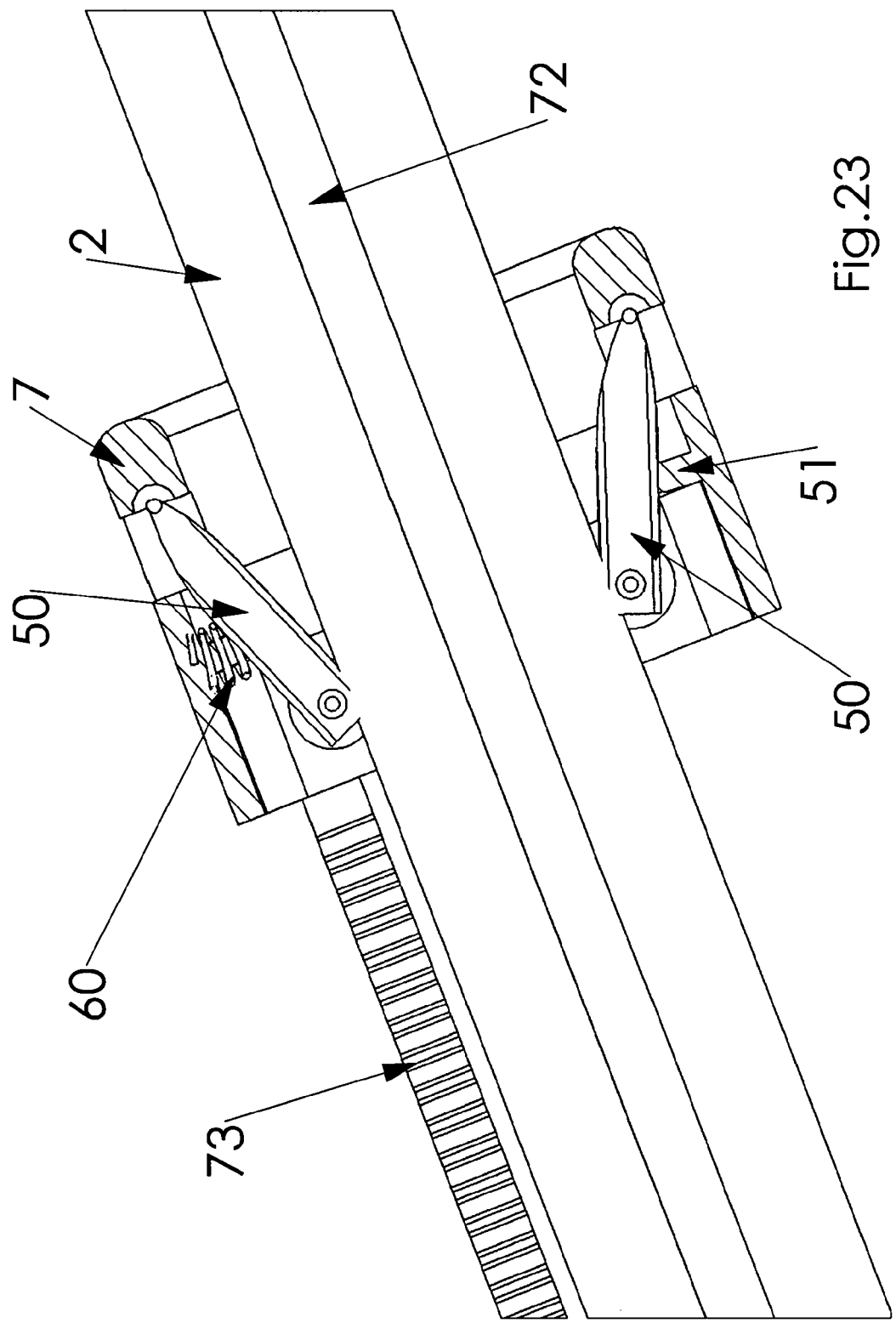
FIG. 23 is an enlarged view of two of the rollers in the most preferred embodiment of the present invention that are each connected on one of its ends to the adjustment ring, with its opposed wheel-carrying end engaged with, and guided in its movement by, one of the four longitudinal channels in the exterior surface of the main tubular shaft.
Figure 26:
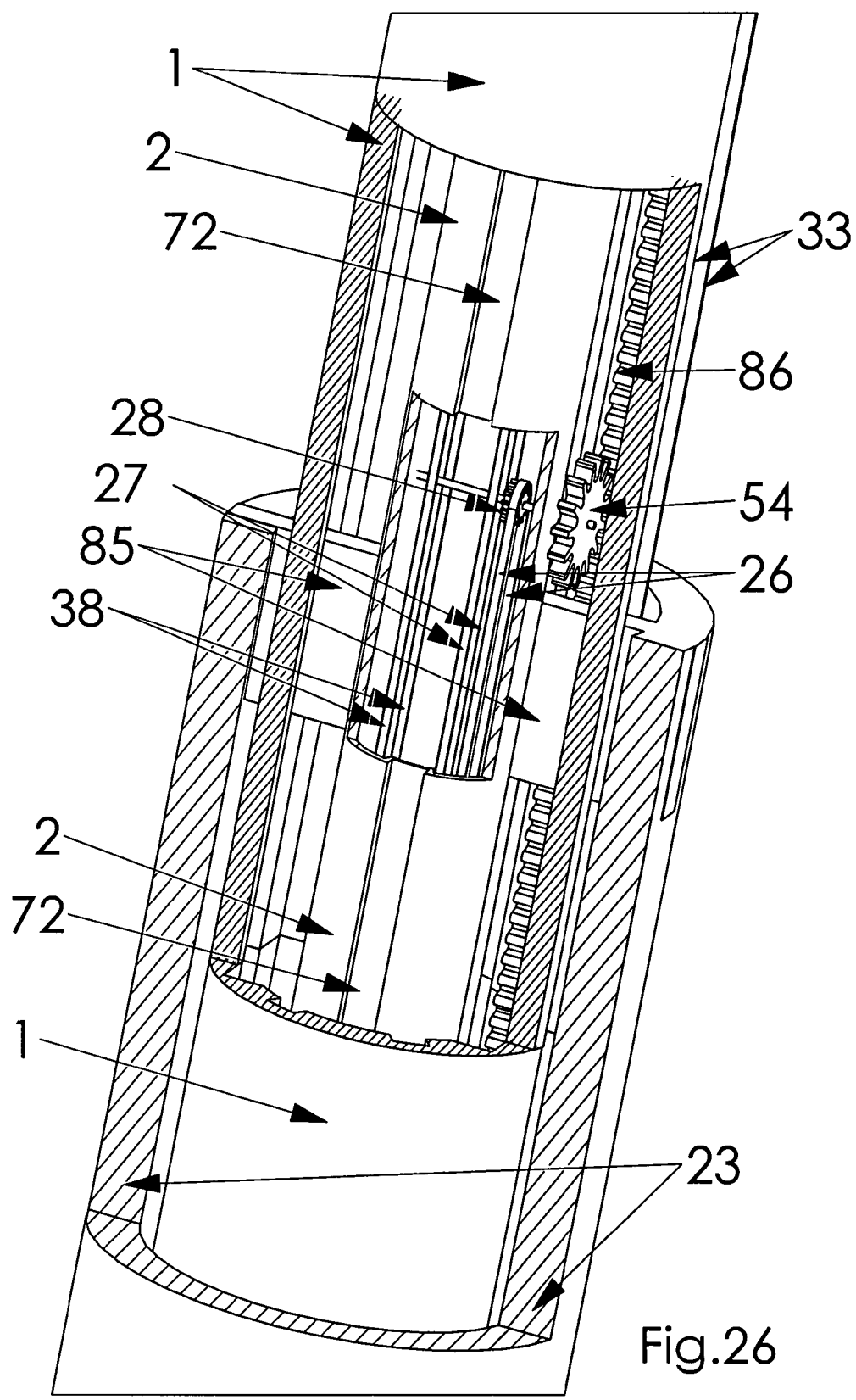
FIG. 26 is an enlarged sectional view of the distal part of the outer shell in the most preferred embodiment of the present invention surrounding a lower portion of the moving cylindrical sheath, and the main tubular shaft housed within the moving cylindrical sheath (although not clear from this view, the main tubular shaft does extend through the outer shell past the lower end of the moving cylindrical sheath). This important connection of outer shell, main tubular shaft, and moving cylindrical sheath is important as it is where the movement of the moving cylindrical sheath on the main tubular shaft back or forth (that corresponds to the movement of the device toward or away from a target visual object) is transmitted through the moving cylindrical sheath's linear rack via engagement of the rack to a pinion gear mounted on an axle secured to the main tubular shaft, and through which another gear transmits the movement via a belt to a set of multiple gears within the gearbox (shown in FIG. 3) secured to the proximal ends of the main tubular shaft and the outer shell, wherein after the set of multiple gears reduces the linear movement coming into the gearbox (such as via a convergence ratio of approximately 100:1.5, the number used in semi-automated convergence calculation examples provided in FIGS. 35 and 36, with the resulting reduced movement then being transmitted mechanically via gears and belts positioned between the gearbox and the diagnostic/sensor probes to actuate the diagnostic/sensor probe gears for proper increase or decrease in convergence of the diagnostic/sensor probes on a target object, as needed.
Figure 31:
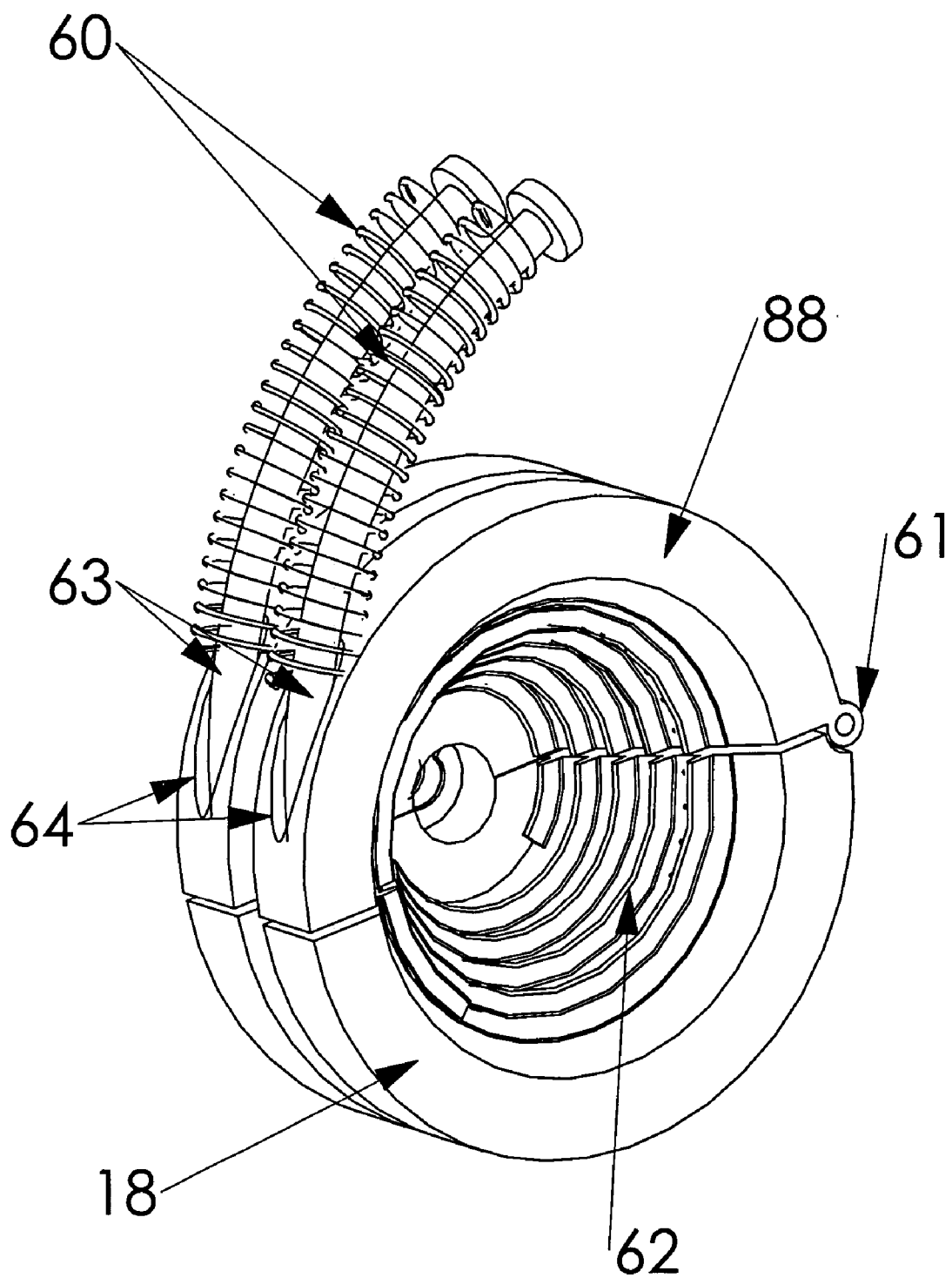
FIG. 31 is an enlarged view of the size-adjustable gear in the most preferred embodiment of the present invention with its springs and shown in a fully closed position.
Figure 32A:
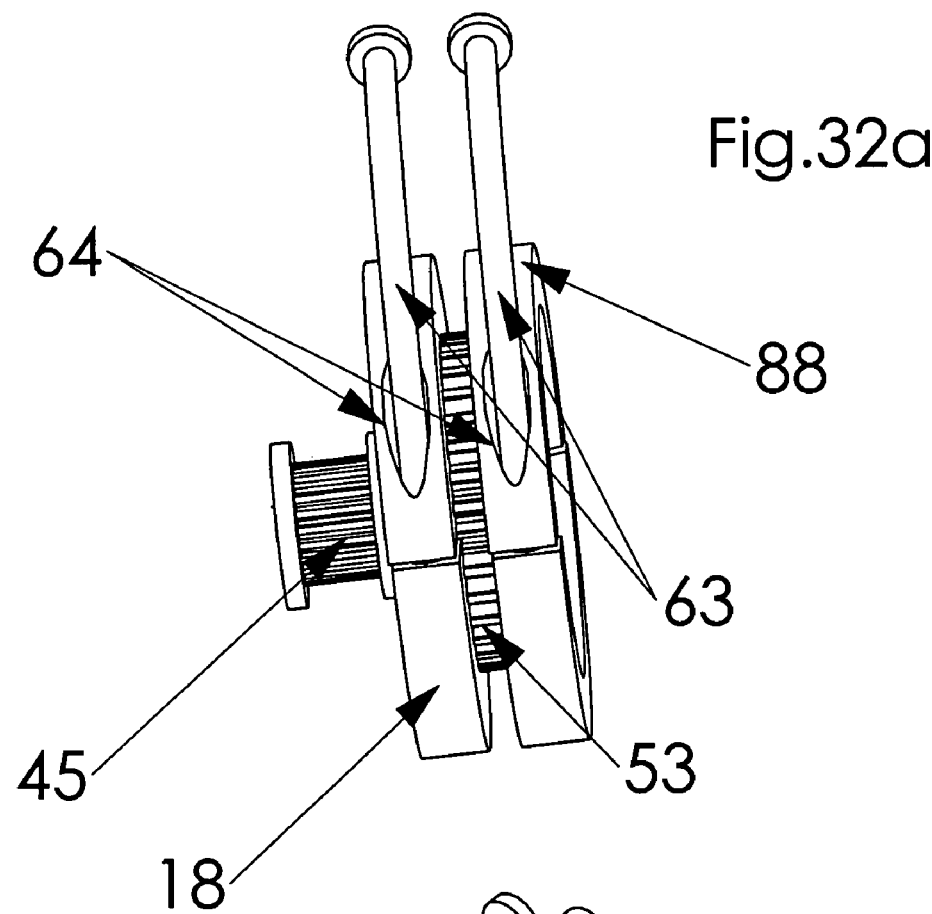
FIG. 32a is a side view of the size-adjustable gear in the most preferred embodiment of the present invention without its springs and still shown in a fully closed position.
Figure 32B:
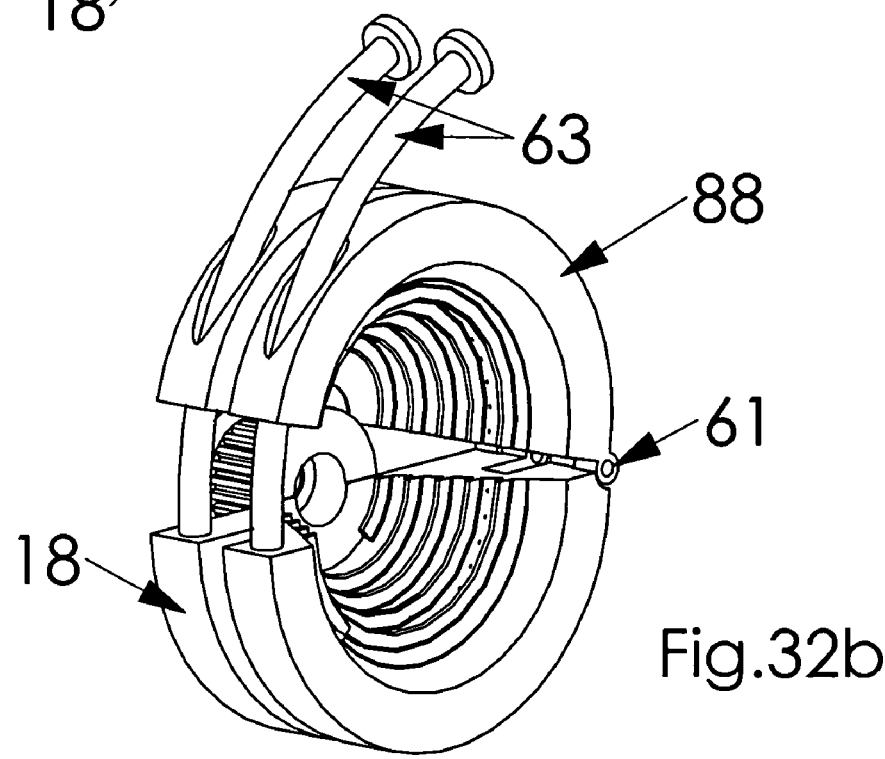
FIG. 32b is a perspective view of the size-adjustable gear in the most preferred embodiment of the present invention without its springs and shown in a partially opened position.
Figure 35:
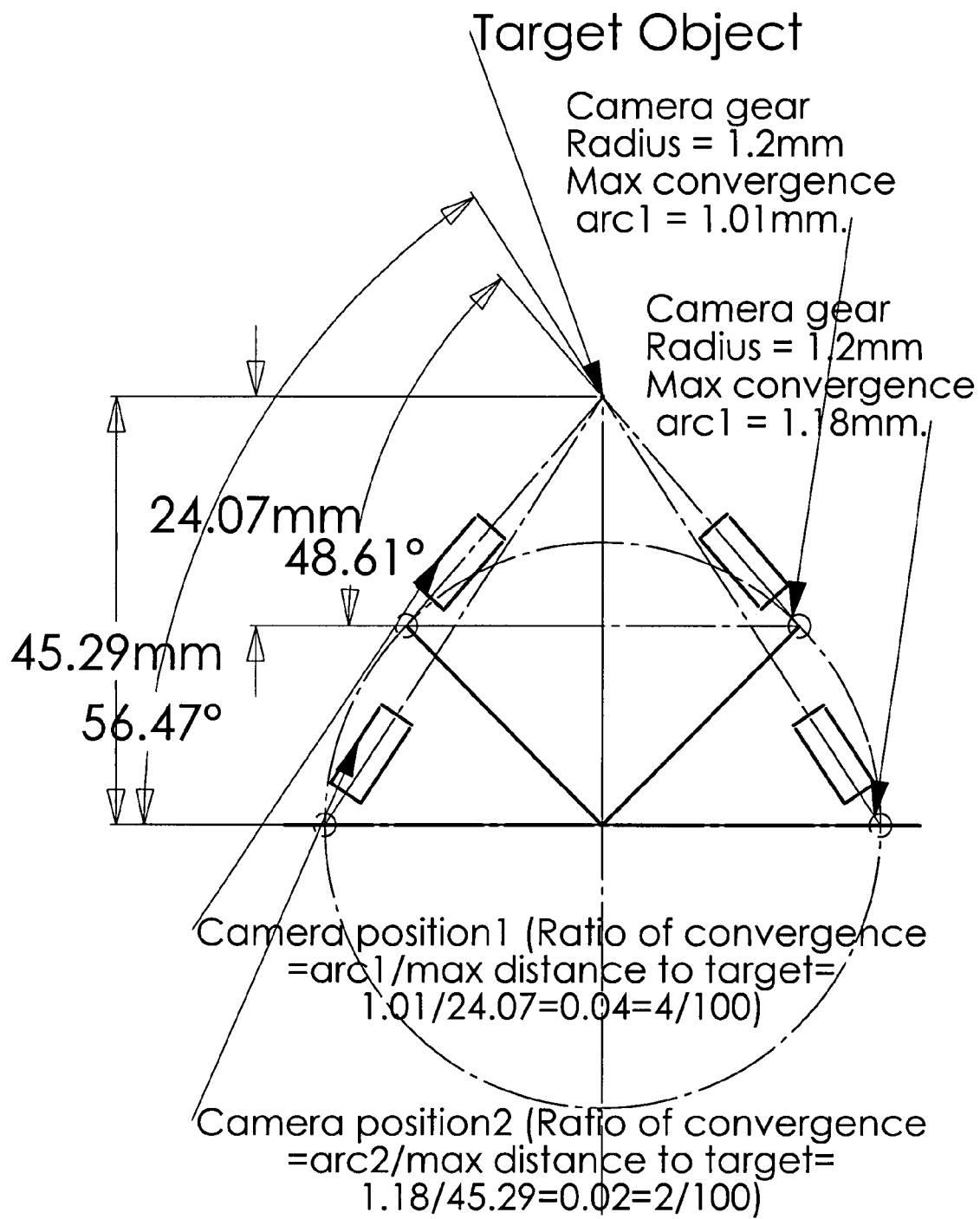
FIG. 35 is a schematic view of the most preferred embodiment of the present invention identifying diagnostic/sensor probe convergence information for two different camera positions usable with a closer target object, one requiring a 100:4 ratio of convergence and the other requiring a 100:2 ratio of convergence, with these calculations only being used for exemplary purposes and the understanding that these ratios can change completely depending on the sizes, diameters, lengths, and shapes of the main tubular shaft, the moving cylindrical sheath, the adjustment ring, the application of the device, and the sets of multiple gears used to meet the demands of the application.
Figure 36:
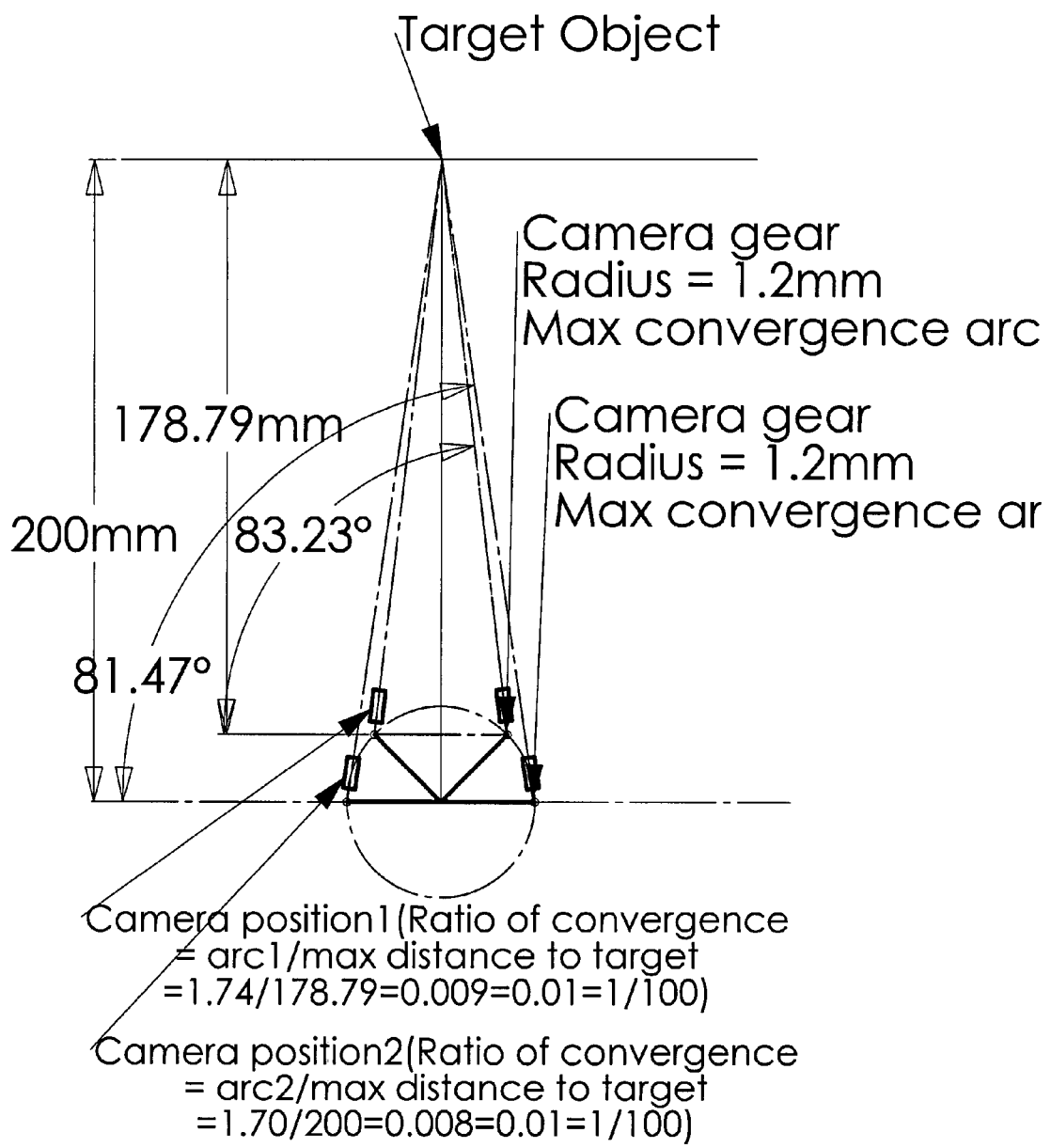
FIG. 36 is a schematic view of the most preferred embodiment of the present invention identifying diagnostic/sensor probe convergence information for two different camera positions usable with a target object that is more distant than that shown in FIG. 35, both revealing a 100:1 ratio of convergence, with these calculations only being used for exemplary purposes and the understanding that these ratios can change completely depending on the sizes, diameters, lengths, and shapes of the main tubular shaft, the moving cylindrical sheath, the adjustment ring, the application of the device, and the sets of multiple gears used to meet the demands of the application.

23. outer shell connected to the main tubular shaft (also referred to as outer shell) [see FIGS. 1, 2*b*, 2*c*, 3, 26, 28*a*, 28*b*, 28*c*]
24. hinge on probe arm 6 [see FIGS. 2*a*, 11]
25. hinge on probe arm 5 [see FIGS. 2*a*, 11]
26. belt engaging gear (#28) that is on the same axle with pinion gear (#54) that engages rack 86 of the moving cylindrical sheath (#1) [see FIGS. 2*b*, 2*c*, 3, 26]
27. belt engaging gear (#29) that is on the same axle with pinion gear (#34) that transmits movement to rack (#48) of the rod (#27) [see FIGS. 2*a*, 2*b*, 2*c*, 3, 4, 6, 7, 26]
28. gear engaging belt (#26) [see FIGS. 2*b*, 26]
29. gear engaging belt (#27) [see FIGS. 2*a*, 4, 6, 7]
30. pair of gears engaging belts (# 36, 37, and 38) to transmit movement from the gearbox (#21) to the diagnostic/sensor probe gears (#31 and 32) for convergence of diagnostic/sensor probes (#3 and 4) [see FIGS. 2*a*, 4, 6, 7]
31. first diagnostic/sensor probe gear (also referred to as imaging probe gear) [see FIGS. 5, 6, 7, 9, 12, 13]
32. second diagnostic/sensor probe gear (also referred to as imaging probe gear) [see FIGS. 5, 6, 7, 13]
33. pair of opposing slots in the moving cylindrical sheath extending in a longitudinal direction [see FIGS. 2*a*, 2*b*, 15, 1, 20, 26]
34. pinion gear that transmits movement to rack (#48) [see FIGS. 2*a*, 4, 6, 7]
35. -unused number-
36. first diagnostic/sensor probe belt connected between gears (#30 and 31) and having a figure-eight shape to assist in making one diagnostic/sensor probe (#3 and 4) move in the opposite direction to the other for convergence [see FIGS. 2*a*, 4, 6, 7, 11, 12, 13, 14]
37. second diagnostic/sensor probe belt connected between gears (#30 and 32) and having a simple looped configuration [see FIGS. 2*a*, 4, 6, 7, 11, 14]
38. belt transmitting movement between gear (#30) and the gearbox (#21) for convergence [see FIGS. 2*a*, 2*b*, 2*c*, 3, 4, 6, 7, 26]
39. spring for alternate configuration for the mounting of diagnostic/sensor probes (#3 and 4) on probe arms (#5 and 6) [see FIG. 14]
40. additional imaging or therapeutic feature (including but not limited to therapeutic radiation probes, laser probes, radio-frequency probes) [see FIGS. 9, 10, 12, 13, 14]
41. light source which can be transmitted via fiber-optics or produced by light-emitting diodes (LED'S) [see FIGS. 2*a*, 9, 10, 12, 13, 14]
42. hinge at the distal end of the main tubular shaft (#2) that engages the probe arms (#5 and 6) and can also mount a target-to-device distance sensor or laser pointer (#66) [see FIGS. 2*a*, 4, 5, 11, 12, 13,]
43. mounting assembly for first diagnostic/sensor probe [see FIGS. 5, 9]
44. mounting assembly for second diagnostic/sensor probe [see FIGS. 5, 12]
45. fixed diameter gear portion of the size-adjustable gear (#18+88), but only attached to its lower part (#18) [see FIGS. 29, 32*a*]
46. proximal end of adjustment ring (#7) [see FIGS. 2*a*, 17, 19*a*, 19*b*]
47. two-rod control assembly [see FIGS. 2, 5, 6, 7, 8]
48. rack in assembly (#47) [see FIGS. 2*a*, 4, 5, 6, 7, 8]
49. spring positioned between the proximal end of moving cylindrical sheath (#1) and the radially-extending brace (#85) connected to the main tubular shaft (#2) and outer shell (#23) [see FIGS. 2, 17]
50. roller assembly for support of adjustment ring (#7) and moving cylindrical sheath (#1) on the main tubular shaft (#2) to allow them to move smoothly back and forth guided by channel (#72), one set of four rollers (#50) is associated with the distal end of adjustment ring and two sets of four roller (#50) are associated with the opposed ends of the moving cylindrical sheath (#1) [see FIGS. 2*a*, 2*b*, 16, 17, 18, 23, 24, 25]
51. arcuate shaped projection that slides into the opening (#52) of a roller (#50) to secure it in its position of use and is found associated with the distal end of adjustment ring (#7) and the distal and proximal ends of the moving cylindrical sheath (#1), the projection also being used to hold spring (#60) in place and guide the movement of wheeled end of a roller (#50) within one of the four longitudinal channels in the external surface of the main tubular shaft (#2) [see FIGS. 21, 23]
52. opening in the roller for arcuate projection (#51) [see FIG. 25]
53. adjustable diameter gear portion of the size-adjustable gear (#18+88) that engages belt (#38) for movement of probe belts (#36 and #37) and convergence of probes (#3 and #4), with one half built into upper part (#88) and the other half built into lower part (#18) [see FIG. 32*a*]
54. pinion gear that engages the rack (#86) in the moving cylindrical sheath (#1) [see FIGS. 2*b*,17, 26]
55. on-off switch for electromagnet (#9), disengages cone-shaped gear (#11) from rack (#73) of adjustment ring (#7) so that adjustment ring (#7) can move freely in and out of the moving cylindrical sheath (#1) without causing convergence [see FIGS. 2*c*,3, 15, 16, 20, 21]
56. representation of a set of multiple gears configured to produce a predetermined convergence ratio from movement it receives from the moving cylindrical sheath (#1), such as but not limited to the approximately 100:1.5 ratio used in the example calculations of FIGS. 35 and 36. For many applications of the present invention the ratio typically ranges between 100:0.5 and 100:5. In applications where less precise convergence is required, semi-automated convergence is often achieved by using a set of multiple gears having an approximately 100:1.5 ratio. Where more precise convergence is required, fully automated convergence can be achieved through use of a set of multiple gears with a predetermined convergence ratio appropriate to the application in combination with a size-adjustable gear (#18+#88) [see FIGS. 2*c*,3]
57. representation of a set of multiple set of gears that transmit movement through belt (#38) to the diagnostic/sensor probe gears (#31 and 32) to actuate convergence [see FIGS. 2*c*,3]
58. gear in gearbox (#21) that transmits movement from control (#22) to belt (#27) to cause the opening and closing of probe arms (#5 and #6) via gears (#29 and #34) and two-rod control assembly (#47) with its rack (#48) [see FIGS. 2*c*,3]
59. target object in FIG. 29 [see FIG. 29]
60. biasing spring for size-adjustable gear (#18+#88) to cause the upper part (#88) to spring back to its original closed position against the lower part (#18) of the size-adjustable gear [see FIGS. 23, 24]
61. hinge for the size-adjustable gear (#18+88) [see FIGS. 31, 32*b*]
62. conical-shaped threaded core of size-adjustable gear (#18+88) [see FIG. 31]
63. a pair of arcuate shaped projections from the lower part (#18) of the size-adjustable gear that guide the movement of the upper part (#88) of the size-adjustable gear as it opens and closes, and each hold a spring (#60) in place [see FIGS. 31, 32a, 32b, 34]
64. openings in the upper part (#88) of the size-adjustable gear through which the pair of arcuate shaped projections (#63) move [see FIGS. 31, 32a]
65. uniform threading on rod (#19) [see FIG. 33]
66. unit that in semi-automated configurations can be used as a laser pointer and in fully automated configurations is used as a target-to-device distance sensor (which optionally can incorporate a laser pointer as well) [see FIGS. 29, 30]
67. set of four alternative mounts for alternative diagnostic/sensor probe configuration [see FIG. 14]
68. diagnostic/sensor probe axle [see FIG. 14]
69. set of four projection rods from adjustment ring (#7) and attached in pairs to proximal end (#46) and fitting loosely within the grooves (#74) in moving cylindrical sheath (#1) [see FIGS. 2a, 11, 13, 14, 16, 17, 18, 19a, 19b]
70. distal end of rack (#48) attached to probe arm (#6) [see FIGS. 4, 8]
71. distal end of two-rod control assembly (#47) attached to probe arm (#5) [see FIGS. 4, 8]
72. set of four longitudinal channels in the external face of the main tubular shaft (#2) [see FIGS. 1, 2a, 2b, 5, 11, 12, 13, 14, 23, 26, 30]
73. rack of adjustment ring (#7) that engages pinion gear (#11) to control the movement of adjustment ring (#7) back and forth on the moving cylindrical sheath (#1) [see FIGS. 2a, 11, 13, 14, 16, 17, 18, 19a, 19b, 23, 30]
74. four longitudinal grooves in the moving cylindrical sheath (#1) that loosely fit the four projection rods (#69) from adjustment ring (#7) and guide them in their movement [see FIGS. 20, 21]
75. longitudinal groove in the moving cylindrical sheath (#1) that loosely fits and guides the rack (#73) of the adjustment ring (#7) [see FIGS. 20, 21]
76. representation of electrical power source for the first electromagnet (#9) [see FIGS. 15, 16, 20, 21]
77. first flexible but non-stretchable cable [see FIG. 27]
78. second flexible but non-stretchable cable [see FIG. 27]
79. first double pulley with a pair of independent winding grooves [see FIG. 27]
80. second double pulley with a pair of independent winding grooves [see FIG. 27]
81. cable end attachment point on pulley, with a set of two on each pulley [see FIG. 27]
82. -unused number-
83. angled top surface of the main tubular shaft (#2) [see FIG. 4]
84. -unused number-
85. radially-extending brace connected between main tubular shaft (#2) and its associated outer shell 23 [see FIGS. 2cb, 2c 26, 28c]
86. rack for the moving cylindrical sheath (#1) that engages the pinion gear (#54) [see FIGS. 16, 17, 18, 20, 26]
87. -unused number-
88. upper part of the size-adjustable gear [see FIGS. 31, 32a, 32b, 34]
89. guide rail for the control rod (#47) that originates from inside main tubular shaft (#2), with sets of two on each side [see FIG. 4]
90. groove guide that receives guide rail (#89) [see FIGS. 4, 8]
91. spring between the adjustment ring (#7) and the moving cylindrical sheath (#1) that extends between the proximal end 46 of adjustment ring (#7) and the distal end of moving cylindrical sheath (#1) [see FIG. 2a]
92. proximal end of two-rod control assembly 47 [see FIG. 8]

DETAILED DESCRIPTION OF THE INVENTION

The present invention provides an endoscopic system and method that is adaptable for therapeutic applications, as well as diagnostic/sensor operation, and is capable of producing 3-dimensional human vision simulated imaging with real dynamic convergence, not virtual convergence. Applications may include use in any space, including but not limited to, intra-abdominal cavities, intra-thoracic cavities, and intra-cranial cavities. Non-medical applications are contemplated that involve viewing into areas inaccessible directly by the human eye, including but not limited to search/rescue, scientific research, and investigative applications. A main tubular shaft 2 with an elongated configuration provides the backbone of the present invention structure. Its proximal end has a shorter and wider outer shell 23 around it that is often three times the diameter of main tubular shaft 2, although not limited thereto. Outer shell 23 is used for improved operator handling of the present invention endoscopic system, and both ends of the outer shell 23 are securely fixed to the proximal portion of the main tubular shaft 2 via braces 85 (preferably using two braces 85 at each end of outer shell 23) and the proximal ends of both main tubular shaft 2 and outer shell 23 are securely attached to a gearbox 21. In contrast, the distal end of the main tubular shaft 2 is connected to two or more imaging probes or diagnostic sensors 3 or 4 via two movable probe arms 5 and 6 (hereinafter imaging probes or diagnostic sensors 3 or 4 will routinely be referred to by the terms 'diagnostic sensors' or 'diagnostic/sensor probes' for consistency of identification and without any limitation intended as a result of using these terms). Diagnostic/sensor probes 3 and 4, as well as movable probe arms 5 and 6, are typically positioned adjacent to one another in a closed arrangement prior to insertion of the distal end of main tubular shaft 2 into a cavity opening, such as but not limited to a endoscopic port (not shown). For creating a 3-dimensional effect, at least two diagnostic/sensor probes 3 and 4 must be the same kind, and one of the same kind diagnostic/sensor probes 3 or 4 must be mounted onto probe arm 5 with the other same kind diagnostic/sensor probe 3 or 4 mounted on probe arm 6. It is contemplated for diagnostic/sensor probes 3 and 4 in the present invention to include, but not be limited to, cameras, ultrasound devices, and other imaging sensors. Diagnostic/sensor probes 3 and 4 are mounted to the distal end of a probe arm 5 or 6, with the proximal ends of the two probe arms 5 and 6 each having a partial-hinge configuration (shown by the numbers 24 and 25 in FIG. 11) that mate with the complementary structure of hinge 42 on the distal tip of main tubular shaft 2 (see FIG. 2a) so as to provide simultaneous movement of both probe arms 5 and 6 on hinge 42 in opposed directions toward and away from one another within a 180 degree angle range of movement (a 90 degree angle range of movement for each probe arm 5 and 6). Probe arms 5 and 6 are also each attached to a different rod of a two-rod control assembly 47 (with probe 6 connected to the rod having a rack 48), which moves back and forth within the main tubular shaft 2. It is the movement of two-rod control assembly 47 toward probe arms 5 and 6 (via rotatable control 22) that causes them to move toward one another and further close, and movement of two-rod control assembly 47 away from probe arms 5 and 6 that causes them to move away from one another and further open. It is the resulting side-to-side movement of the probe arms 5 and 6 within a 180-degree angle range of movement (to and from the fully closed position where the diagnostic/sensor probes 3 and 4 are positioned adjacent to one another) that creates a change in the distance between diagnostic/sensor probes 3 and 4 that can be adjusted to the average intra-pupillary distance of approximately 5-7 cms found between human eyes, thereby allowing the diagnostic/sensor probes 3 and 4 to have depth perception equivalent to that of human eyes (for similar sized objects positioned at similar distances from the human eyes). The ability to adjust the distance between the probe arms 5 and 6 at any time also gives the operator variability for navigating in small, narrow, and irregularly-shaped spaces inaccessible by the unaided human eye, while at the same time providing the operator an option to move the diagnostic/sensor probes 3 and 4 further apart at most of the probe arm 5 and 6 positions to enhance depth perception for a closer and more detailed look at any feature or object encountered (not shown, other than as the target object 59 identified in the schematic representation of FIG. 29). Another feature of the present invention is convergence which is dynamic and can be achieved through dynamic positioning adjustments of diagnostic/sensor probes 3 and 4 on probe arms 5 and 6 which is done by semi-automated or fully automated means that are explained in details later on. The image from one diagnostic/sensor probe (either 3 or 4) is transmitted to a separate display system mountable in front of one of the operator's two eyes, with the image from the remaining diagnostic/sensor probe 3 or 4 being transmitted to a separate display system mountable in front of the second operator eye, wherein the independent display systems in front of each operator eye can be incorporated using a computer system into the images transmitted to the same head-mounted video system (not shown), but not limited thereto. Further, imaging (such as ultrasound images) from multiple additional imaging features 40 secured to the distal end of the same probe arm 5 or 6 can be superimposed on correspondent images (such as a camera image) from diagnostic/sensor probes 3 and 4, according to operator preference or need. The creation of a target image requires light, which can also be provided by the present invention via fiber-optics or LED's (used only as examples and not limited thereto), or any other light source that has the compact configuration needed for being mounted adjacent to the diagnostic/sensor probes 3 and 4 on the distal ends of the probe arms 5 and 6 (and entry into the small openings typically encountered when entering a target object viewing area) while also having the capability of producing the needed amount of light for diagnostic/sensor probe 3 and 4 use with minimal heat generation.

Convergence of diagnostic/sensors 3 and 4 is achieved as a result of the linear movement of a moving cylindrical sheath 1 that slides easily back and forth on the main tubular shaft 2, with this linear movement being mechanically transmitted to gearbox 21 via multiple belts and gears, after which it is reduced by an appropriate amount to correct for convergence and then is transmitted from gearbox 21 to the diagnostic/sensor probe gears 31 and 32 connected to diagnostic/sensors 3 and 4 to turn each of them on its axis. An adjustment ring 7 in the present invention is positioned between the moving cylindrical sheath 1 and the main tubular shaft 2, and is typically in fixed engagement with the moving cylindrical sheath 1 to move in the same direction with it (toward or away from the distal end of the main tubular shaft 2). An exception to this fixed engagement (where adjustment ring 7 instead travels freely in or out of the moving cylindrical sheath 1 without any resulting convergence of diagnostic/sensor probes 3 and 4) occurs when cone-shaped pinion gear 11 is disengaged from the rack 73 on adjustment ring 7 via manipulation of an on-off switch 55 and also when rotatable manual control 8 is manipulated to control adjustment ring 7 positioning back and forth on the moving cylindrical sheath 1. Adjustment ring 7 has four projecting rods 69 (and a rack 73 associated with one projecting rod 69) that slide back and forth with a loose fit within four corresponding grooves 74 in the moving cylindrical sheath 1.

For additional clarity in understanding the present invention before a detailed explanation of each illustration is provided, several examples of the interrelation and interaction of present invention components are presented below. When the diagnostic/sensor probes 3 and 4 and the distal end of the main tubular shaft 2 are inserted into a cavity (such as but not limited to an abdominal cavity with a endoscopic port, not shown), the main tubular shaft 2 and diagnostic/sensor probes 3 and 4 slide easily through the endoscopic port into the abdominal cavity but the adjustment ring 7 is stopped from traveling with main tubular shaft 2 into the abdominal cavity by the external structure of the endoscopic port. The forward movement of main tubular shaft 2 into the abdominal (or any other cavity) creates backward movement of the joined adjustment ring 7 and the moving cylindrical sheath 1 on the main tubular shaft 2 in a direction away from imaging probes 3 and 4. This backward movement of moving cylindrical sheath 1 is transmitted via the rack 86 on the moving cylindrical sheath 1 to the gear 54 secured to the main tubular shaft 2. The rotation of gear 54 provides movement for the gear 28 mounted on the same axle with gear 54. The moving gear 28 then transmits movement to the belt 26 engaging it, which is then transmitted to an appropriate set of multiple gears 56 in gearbox 21 (connected to the proximal end of the main tubular shaft 2) that mechanically communicate with the opposed end of belt 26. In semi-automated applications, the set of multiple gears 56 is selected to provide a predetermined ratio of convergence (calculated prior to invention manufacture to fit the application in which it will predominantly be used). In the example provided in FIGS. 35 and 36, calculations support the use of an average ratio of convergence of approximately 100:1.5 to reduce or transform the linear movement coming into gearbox 21 from the moving cylindrical sheath 1, which is then mechanically transmitted to diagnostic/sensor probes 3 and 4 to increase the amount of their convergence via gear 57, belt 38, and a pair of gears 30 positioned between gearbox 21 and probe belts 36 and 37, which causes belts 36 and 37 to respectively turn each probe gear 31 and 32 on its axis and cause further convergence on the particular structure or object being viewed. In contrast, a backward (pulling) movement of the main tubular shaft 2 away from the visual target being viewed allows the adjustment ring 7 (and the moving cylindrical sheath 1 connected to it) to spring and slide forward on the main tubular shaft 2 until it contacts the external structure of the endoscopic port. This spring/slide forward movement is actuated by the spring 49 positioned between the moving cylindrical sheath 1 and a radially-extending brace 85 secured to the distal end of outer shell 23. The spring/slide forward movement of moving cylindrical sheath 1 affects gear 54 on the main tubular shaft 2 and repeats the same steps of mechanical movement transmission mentioned above, but in the opposed direction so the resulting movement of belts 36 and 37 respectively turns each probe gear 31 and 32 on its axis to decrease in the amount of convergence on the particular structure or object being viewed.

In addition to the movement of adjustment ring 7 described above during the insertion of the distal end of main tubular shaft 2 into a cavity opening, at any time, an operator can use rotatable manual control 8 (which is mounted through the moving cylindrical sheath 1 and connected to a pinion gear 11 that engages the rack 73 of adjustment ring 7) to move adjustment ring 7 in and out of the distal end of moving cylindrical sheath 1. Thus, when the distal end of main tubular shaft 2 has been inserted through the endoscopic port to a cavity (example an abdominal cavity) and forward movement of adjustment ring 7 is blocked by the external structure of the endoscopic port, and thereafter, if an operator attempts to move adjustment ring 7 forward on the moving cylindrical sheath 1 using the rotatable manual control 8 (as forward movement of adjustment ring 7 is blocked and cannot occur), backward movement of the moving cylindrical sheath 1 will occur on the main tubular shaft 2, as well as increased convergence of diagnostic/sensor probes 3 and 4 on that particular structure or object by an appropriate amount via the same mechanical transmission of movement in and out of gearbox 21 described in the previous example. In contrast, opposed operator movement of rotatable manual control 8 to cause backward movement of adjustment ring 7 (away from the distal end of main tubular shaft 2) into the inside of the moving cylindrical sheath 1 results in springing/sliding forward movement of the moving cylindrical sheath 1 (via the spring 49 attached between the proximal end of moving cylindrical sheath 1 and the radially-extending brace 85 securing the main tubular shaft 2 to its shell 23) and a reduction in convergence on the particular structure or object being viewed.

Movement of adjustment ring 7 is further affected by the activation of on-off switch 55, which results in a quick reset of diagnostic/sensor probes 3 and 4 to the neutral or zero position with zero convergence (with the longitudinal axes of both diagnostic/sensor probes 3 and 4 become parallel to each other, the zero position is defined elsewhere herein as the position where probe arms 5 and 6 remain in their fully closed position after clearing a cavity wall and before any convergence takes place) which occurs by disengaging pinion gear 11 from rack 73 and allowing the free movement of adjustment ring 7 in and out of the distal end of moving cylindrical sheath 1, which in turn allows the moving cylindrical sheath 1 to spring and slide forward on the main tubular shaft 2 to its primary position (the closest position that the distal end of the moving cylindrical sheath 1 can move toward the distal end of the main tubular shaft 2) actuated by the spring 49, whether the movement of the adjustment ring 7 is blocked by the external structure of the endoscopic port or not. This reset action is important prior to the first introduction of the distal end of the main tubular shaft 2 into a cavity and during operator movement of the device further in or out of the cavity and toward or away from a visual target while the probe arms 5 and 6 are in fully closed position (with diagnostic/sensor probes 3 and 4 in close relation and touching each other) when no convergence is needed. Thus, the reset action allows easy insertion of diagnostic/sensor probes 3 and 4, probe arms 5 and 6, and the distal end of main tubular shaft 2 through a cavity opening or port and prevents damage that could otherwise occur to vulnerable parts of the present invention should unexpected resistance be encountered during cavity entry. When the electromagnet 9 housed within rotatable manual control 8 is activated by on-off switch 55, power supplied to it from power supply 76 via electrical wiring 13 causes electromagnet 9 to draw the cone-shaped pinion gear 11 toward it, temporarily disengaging gear 11 from rack 73 and compressing a spring 12 positioned between gear 11 and electromagnet 9. When an operator thereafter uses on-off control 55 (which can be positioned on gearbox 21) to deactivate electromagnet 9, the stored energy in compressed spring 12 causes cone-shaped pinion gear 11 to re-engage rack 73, re-establishing a direct mechanical movement transmission path allowing for convergence of diagnostic/sensor probes 3 and 4 via rotatable manual control 8. The preferred cone-shaped gear 11 has its tapered end pointing toward the main tubular shaft 2 so that it may readily move back to its original position engaging rack 73 when electrical power to electromagnet 9 ceases.

Thus, adjustment ring 7 has multiple functions, including compensation for the distance traveled by the distal end of main tubular shaft 2 after its introduction into a cavity (such as but not limited to an intra-abdominal cavity) and until the distal end of main tubular shaft 2 reaches the zero position (also referred to as the primary and original position) where probe arms 5 and 6 have cleared the cavity wall and before any convergence takes place. This function is particularly important to medical applications of the present invention, where the thickness of the anterior abdominal wall can vary significantly from one person to another. Other functions of adjustment ring 7 are to allow manual control of the convergence of the diagnostic/sensor probes 3 and 4 on the particular structure or object being viewed to account for any drift in convergence, and when selecting the first visual target at the initial installation of the laparoscope into the cavity (and also any different targets at different distances from diagnostic/sensor probes 3 and 4), and the reset action needed prior to the first introduction of the device to a cavity and when removing the device out of the cavity. If the reset action is not accomplished prior to entry of the present invention into a endoscopic port, diagnostic/sensor probes 3 and 4 may not be optimally positioned for successful entry into the endoscopic port. In addition, without the free movement of adjustment ring 7, it could be placed at risk of breaking when laparoscopic entry is attempted. The reset action is also used when diagnostic/sensor probes 3 and 4 come together in automated convergence applications to prevent computer 15 from attempting further convergence adjustment.

Prior to manufacture of a present invention device, the applications for which it is to be used must be evaluated and a determination made as to the maximum distance anticipated from the distal tip of the main tubular shaft 2 to most targets. Using this information (and other information such as that relating to diagnostic/sensor probe gear size) calculations may be made to determine the ratio of convergence needed for any visual target at any specified distance from the present invention device. An average ratio of convergence can then be calculated upon which to base selection of an appropriate set of gears 56 for reducing the linear movement of the moving cylindrical sheath 1 the proper amount for turning the diagnostic/sensor probe gears 31 and 32 sufficiently to obtain convergence. Examples of ratio of convergence calculations are shown in FIGS. 35 and 36, with FIG. 35 showing calculations for a closer visual target and FIG. 36 showing calculations for a more distance visual target. As can be seen in FIGS. 35 and 36, ratio of convergence calculations first require measurement of the maximum distance to target, which is the distance between the visual target and the mid-point of the horizontal line extending between the center (axis) of each diagnostic/sensor probe gear 31 and 32 when the present invention device is in the primary/original position (also referred to as the zero position and defined as positioning immediately after the initial insertion of the distal end of the main tubular shaft 2 into a cavity, where probe arms 5 and 6 have cleared the cavity wall and before any convergence takes place). This distance between the mid-point of the horizontal line and the visual target is the maximum length through which the present invention device can travel toward the visual target (and when the distal end of the main tubular shaft 2 travels from the zero position further into a cavity, the adjustment ring is blocked from forward movement and simultaneous backward movement of the adjustment ring 7 and the moving cylindrical sheath 1 occurs on the main tubular shaft 2). Ratio of convergence calculations also require measurement of the maximum convergence arc that diagnostic/sensor probe gears 31 and 32 should turn on their axis toward the visual target to achieve the full range of convergence on this target (which is the full range of convergence that can occur between the starting point of the present invention device at the previously mentioned mid-point of the horizontal line between diagnostic/sensor probe gears 31 and 32 and end point when the present invention reaches the visual target). The needed maximum convergence arc is the part of the circumference of diagnostic/sensor probe gears 31 and 32 that corresponds to the angle between the line extending between center (axis) of both diagnostic/sensor probe gears 31 and 32, and a second line extending from center (axis) of either diagnostic/sensor probe gear 31 or 32 and the visual target. Thus, the maximum arc of convergence is equivalent to the angle of convergence multiplied by diagnostic/sensor probe gear circumference (either that of 31 or 32, as both should be the same), with the resulting number divided by the number 360 (which represents the number of degrees in a full circle). The ratio of convergence can then be calculated by dividing the maximum convergence arc by the maximum distance from the zero position to the visual target. The example of this calculation in FIG. 35 for a first camera position shows a calculated 4/100 ratio of convergence resulting from the number 1.01 being divided by the number 24.07 (representing the maximum distance to target in mm). A 4/100 ratio of convergence in camera position 1 means that every 4 mm of turning movement in the diagnostic/sensor probe gear 31 or 32 to converge on a visual target requires 100 mm movement of the moving cylindrical sheath 1 (as well as joined adjustment ring 7) backward on the main tubular shaft 2, the backward movement occurring concurrently with the forward movement of the device toward the visual target. The 4/100 ration of convergence can also be referred to as 100:4, which is defined as every 100 mm movement of the device toward the visual target causes a 100 mm movement of the moving cylindrical sheath 1 (and the adjustment ring 7 joined to it) backward on the main tubular shaft 2 that causes a 4 mm turning movement of the diagnostic/sensor probe gears 31 and 32 for additional convergence of diagnostic/sensor probes 3 and 4 on the visual target. Prior to using a semi-automated configuration of the present invention in a specific application and selecting a set of multiple gears 56 with a predetermined ratio of convergence appropriate to the amount of convergence anticipated for the application, one would need to estimate the distance from the present invention device at the primary/original position to the farthest possible target anticipated in the application (or within the cavity that the present invention device will be primarily used) and accordingly calculate the ratio of convergence for this target distance as previously described above. One would thereafter perform ratio of convergence calculation for several shorter target distances, and average these ratios for use in selecting the predetermined convergence ratio needed for the set of multiple gears represented in the present invention by the number 56. In fully-automated configuration, although a set of multiple gears with a pre-determined ratio of convergence is also used, the computer 15 will dynamically calculate the ratio of convergence each time the present invention device moves, and from the continually changing information it receives from multiple device sensors, computer 15 will activate an electromagnet 16 and a motor 14 to change the power (diameter) of one or more size-adjustable gears 18+88 to affect needed convergence ratio changes, which are mechanically transmitted to diagnostic/sensor probe gears 31 and 32 via the same belts and gears previously mentioned.

Fully automated dynamic convergence relies upon continuous receipt of sensor information by computer 15 that at a minimum includes the current positioning of diagnostic/sensor probes 3 and 4, probe arms 5 and 6, shaft-to-target distance, and the diameter of size-adjustable gear 18+88. Ratios of convergence are sometimes also referred to herein as transformation ratios. The transformation ratio ranges in present invention examples shown in FIGS. 35 and 36 are between 100:0.5 and 100:5. It must also be understood that the sizes and distances used in the calculations provided in FIGS. 35 and 36 are for simplification only, and the ratio of convergence can be completely different from that shown according to changes in the sizes, diameters, lengths, and shapes of the main tubular shaft 2, the moving cylindrical sheath 1, the adjustment ring 7, and the many gears, belts, pulleys, cables, and springs selected according to the intended application. For example, if the device was made to be used in the abdominal cavity, one can assume that the maximum distance between the diagnostic/sensor probes 3 and 4 (while the device is in its primary/original position after probe arms 5 and 6 clear the cavity wall and no convergence has yet occurred—the zero position) and the farthest visual target object 59 that can be seen in the abdomen is roughly 25 to 35 cms. Calculations can then be made to determine the average ratio of convergence needed, and accordingly provide the sizes and shapes of gears and/or pulleys for the present invention that are capable of appropriately reducing the amount of movement transmitted from moving cylindrical sheath 1 to gearbox 21 (which is then mechanically re-routed to the diagnostic/sensor probe gears 31 and 32 via belt 38, gears 30, and belts 36 and 37) for convergence of diagnostic/sensor probes 3 and 4.

The shaft-to target sensor 66 used in the fully-automated configuration of the present invention to measure the maximum distance between the main tubular shaft 2 and a target object 59 is placed between probe arms 5 and 6 and secured to the distal end of the main tubular shaft 2 by the same hinge 42 used for pivoting attachment of probe arms 5 and 6. Shaft-to target sensor 66 can be activated automatically when probe arms 5 and 6 are opened. In the alternative, in the semi-automated configuration of the present invention, instead of using unit 66 as a shaft-to target sensor, a laser pointer can be used to aid the operator in the alignment of the longitudinal axis of main tubular shaft 2 with the visual target 59, and in doing so aid in the convergence adjustment of diagnostic/sensor probes 3 and 4 on target object 59 when needed. In many routine applications where the differences in convergence ratios at different spaced-apart probe arm 5 and 6 positions are minimal, the ratio of transformation in convergence can be predetermined (as in the example of semi-automated application above where it is set to 100:1.5 by a pre-selected set of multiple gears 56). As needed in semi-automated applications, the operator can adjust the convergence on the visual target 59 manually by using rotatable manual control 8 to adjust adjustment ring 7 and compensate for any drift in convergence. In contrast, in fully automated applications where a very high level of accuracy in convergence is required, a computer 15 can be used to calculate the needed transformation ratio, along with position sensors (not identified by number as it would be an integral part of diagnostic/sensor probes 3 and 4), an electric motor 14, an electromagnet 16, and one or more size-adjustable gears (18+88). After receipt of positioning information transmitted to it by sensors, the computer 15 can calculate the change in the dimension of the size-adjustable gear (18+88) needed to optimize convergence of diagnostic/sensor probes 3 and 4 on a target object, and thereafter activate electromagnet 16 to produce resistance in the turning movement of the size-adjustable gear (18+88) to allow the uniformly increasing diameter threading 17 of rod 19 to move within the size-adjustable gear (18+88) to turn and change its diameter dimension a calculated amount. Another sensor (not shown) in the size-adjustable gear (18+88) will send feedback information to computer 15 when the required change in the size-adjustable gear (18+88) is obtained so that computer 15 knows when to turn off electromagnet 16 and electric motor 14. The size-adjustable gear (18+88) has an upper part 88 and a lower part 18 that are secured together by a hinge 61. Size-adjustable gear (18+88) also has a conical-shaped threaded core 62 and an adjoining threaded core of uniform diameter (not separately numbered). Hinge 61 allows the halves of the size-adjustable gear (18+88) to open and close relative to one another, and thereby change its size and power so that the rod 19 with its uniformly increasing diameter threading 17 can be moved through the conical-shaped threaded core 62 of the size-adjustable gear (18+88) for an increase or decrease in convergence of diagnostic/sensor probes 3 and 4. It must be kept in mind that the gears and belts shown throughout the accompanying illustrations are only representative, and the actual sizes and ratios may be different according to the technology available at the time of construction as long as the device is as small as needed for the intended application. Although not shown, the present invention device may also have an LED or pleasant alarm sound-producing assembly that is connected in an electrical circuit with minimal electricity source in a way that the sound of the alarm and/or turn on the LED light when the two diagnostic/sensor probes 3 and 4 mounted on the two probe arms 5 and 6 touch one another. The alarm alerts the operator that diagnostic/sensor probes 3 and 4 are very close together and no more convergence can occur.

FIG. 1 is a perspective view of the most preferred embodiment of the present invention having two diagnostic/sensor probes 3 and 4 each mounted on the distal end of a separate probe arm (respectively represented in the illustrations by the numbers 5 and 6). The proximal ends of probe arms 5 and 6 are connected to the distal end of the main tubular shaft via complementary and cooperating hinge components (shown in FIG. 2*a* by the numbers 24, 25, and 42), and moveable by the two-rod control assembly 47 shown in FIGS. 2*a* and 8. FIG. 1 also shows main tubular shaft 2 having an associated outer shell 23 that together are secured in fixed association to a gearbox 21, and a manual control 22 used for opening and closing probe arms 5 and 6 that is conveniently located on gearbox 21. FIG. 1 also shows a moving cylindrical sheath 1 that travels inside outer shell 23, and an adjustment ring 7 positioned between the distal end of the moving cylindrical sheath 1 and the main tubular shaft 2. In addition, FIG. 1 shows the adjustment ring 7 having projection rods 69 extending into the moving cylindrical sheath 1, the main tubular shaft 2 having a longitudinal channel 72, and a rotatable manual control 8 with attached representation of electrical wiring 13 that is intended to connect an electromagnet (shown in FIGS. 17 and 18 by the number 9) housed within rotatable manual control 8 to an on-off switch (shown in FIG. 16 by the number 55 and typically placed in gearbox 21 as shown in FIG. 3) and a power source (shown in FIG. 16 by the number 76) for remote disengagement of pinion gear 11 from rack 73 via switch 55 to allow adjustment ring 7 to move freely with respect to moving cylindrical sheath 1 (otherwise adjustment ring 7 and moving cylindrical sheath 1 move together). What is not shown in FIG. 1, but visible in FIG. 2*a*, is the two-rod control assembly 47 with rack 48 that moves within the main tubular shaft 2 with pinion gear 34 engaging rack 48 (also shown in FIG. 4). FIG. 1 also shows an aperture at the end of a channel built into and along the length of the invention to allow the concurrent introduction and use of one or more independent instruments inside the cavity where the device is inserted. Independent instruments can include, but are not limited to, endoscopic scissors, graspers, and biopsy forceps. One or more channels 10 can be used through gearbox 21 or elsewhere.

FIGS. 2*a*, 2*b*, and 2*c* show the most preferred embodiment of the present invention in greater detail, with external and internal components separated from one another for a more detailed view of each. FIG. 2*b* provides a continuation of the illustration in FIG. 2*a*, and FIG. 2*c* provides a continuation of the illustration in FIG. 2*b*. FIG. 2*a* is the first part of an exploded view and shows diagnostic/sensor probes 4 and 3 removed from their respective probe arms 6 and 5, and probe arms 6 and 5 respectively having probe hinges 24 and 25 used for pivotal connection of probes 6 and 5 to the complementary hinge structure 42 on the distal end of the main tubular shaft 2. A light source 41 is shown associated with each diagnostic/sensor probe 3 and 4. Further, centrally between probe arms 5 and 6, FIG. 2*a* shows a belt 36 for transmitting convergence instructions to diagnostic/sensor probe gear 32 (see FIG. 5), a belt 37 for transmitting convergence instructions to diagnostic/sensor probe gear 31 (see FIG. 5), a centrally located gear 30 to which belts 36 and 37 are connected, and a belt 38 extending from the multiple sets of gears (represented by the number 57) in gearbox 21 (see FIG. 3) that provides appropriate movement to gear 30 for the convergence of diagnostic/sensor probes 3 and 4 depending upon whether 100:1.5 or other convergence ratios are required. To the left of belt 38, FIG. 2*a* shows the adjustment ring 7 that is positioned between moving cylindrical sheath 1 and the main tubular shaft 2. Four similarly configured projection rods 69 (more clearly shown in FIGS. 19*a* and 19*b*) extend from adjustment ring 7 to its split proximal end 46. FIG. 2*a* also shows adjustment ring 7 having a rack 73 positioned parallel to the projecting rods 69 and also extending from adjustment ring 7 to its proximal end 46, as well as the gear 11 with a conical configuration that engages rack 73 to move the adjustment ring 7 back and forth on the moving cylindrical sheath 1 in response to operator movement of the rotatable manual control 8 positioned in FIG. 2*a* to the left of conical gear 11. Also to the left of adjustment ring 7, FIG. 2*a*, shows moving cylindrical sheath 1 with its elongated slot 33 and the spring 91 connected between the proximal end 46 of adjustment ring 7 and the distal end of moving cylindrical sheath 1. To the far right of belt 38, FIG. 2*a* shows one of the four longitudinally-extending channels 72 in the exterior surface of main tubular shaft 2 that helps to guide the movement of adjustment ring 7 and the moving cylindrical sheath 1 on main tubular shaft 2. FIG. 2*a* also shows the hinge 42 on the distal end of main tubular shaft 2 that is configured for pivotal connection of probe arms 6 and 5 via the hinges 24 and 25 respectively connected to (or formed into) their proximal ends, which allows for side-to-side rotation of probe arms 5 and 6 through 180 degrees. Immediately to the right of belt 38, FIG. 2*a* shows the two-rod control assembly 47 used for opening and closing probe arms 5 and 6, the rack 48 on two-rod control assembly 47, the pinion gear 34 engaging rack 48, and a smaller gear 29 that turns on the same axis with pinion gear 34 and engages belt 27. The four rollers marked by the number 50 are shown to the right of cone-shaped pinion gear 11, which are used to allow smooth movement back and forth of moving cylindrical sheath 1 on main tubular shaft 2. A similar unmarked set of four rollers (later marked by the number 50 in FIG. 23) is shown to the right of adjustment ring 7 and is used to provide smooth movement between adjustment ring 7 and main tubular shaft 2.

FIG. 2b is a continuation of the exploded view in FIG. 2a and shows main tubular shaft 2 on the right with an outer shell 23 covering the proximal end of main tubular shaft 2, one of its four longitudinally-extending channels 72 that help to guide the movement of adjustment ring 7 and the moving cylindrical sheath 1 on main tubular shaft 2, and the radially-extending brace 85 connecting the main tubular shaft 2 to its associated outer shell 23. To the left of main tubular shaft 2, FIG. 2b also shows the continuation of belts 38 and 27, and another set of four rollers 50, which are used to control movement between the proximal end of moving cylindrical sheath 1 and main tubular shaft 2. In addition, FIG. 2b shows one of the pair of elongated opposing slots 33 in moving cylindrical sheath 1 (which allows the moving cylindrical sheath 1 to fit appropriately around the radially-extending brace 85 and move easily on the main tubular shaft 2 not being blocked by the radially-extending brace 85). FIG. 2b also shows the pinion gear 54 that is secured via its axle to the main tubular shaft 2 but mounted outside main tubular shaft 2 for engagement with rack 86 inside moving cylindrical sheath 1 (also shown in FIGS. 17 and 26) and the spring 49 (also shown in FIG. 17) that is used between the proximal end of moving cylindrical sheath 1 and the radially-extending brace 85 connected between outer shell 23 and main tubular shaft 2. FIG. 2b further shows the gear 28 (also shown in FIG. 26) that also moves on the same axis with pinion gear 54 and engages the belt 26 that transmits the movement of moving cylindrical sheath 1 to the set of multiple gears (identified by the number 56 in FIG. 3) needed to establish 100:1.5 or other gear ratio (that is predetermined for the intended application of the invention) for diagnostic/sensor probe 3 and 4 convergence.

FIG. 2c is a continuation of the exploded views in FIGS. 2a and 2b showing the third part of the most preferred embodiment of the present invention with a gearbox 21 shown on the right side of the illustration, which can be adapted for connection to a computer (shown in FIG. 29 by the number 15) having the capability to provide precise automated dynamic change in convergence ratio by actuating change in the diameter of the size-adjustable gear 18+88 when a very high level of accuracy in convergence is needed. The on-off switch 55 on gearbox 21 is used to turn on the power source 76 to electromagnet 9 for remote disengagement of pinion gear 11 from rack 73 to allow adjustment ring 7 to move freely relative to moving cylindrical sheath 1 (otherwise the two move together) and reset its position to a primary/original position where the diagnostic/sensor probes 3 and 4 are parallel to one another with zero convergence. Disengagement of pinion gear 11 from rack 73 is also needed during initial insertion or removal of the distal end of main tubular shaft 2 from a working space or cavity. Once free movement of adjustment ring 7 is no longer needed, on-off switch 55 is used to turn off the electrical power to electromagnet 9, thereby allowing pinion gear 11 to return to its engaged position with rack 73. FIG. 2c also shows the radially-extending braces 85, two of which are secured inside each end of the outer shell 23 (proximal and distal) and connect it to the main tubular shaft 2. FIG. 2c further shows the lower ends of belts 26, 27, and 38, and the lower gears 56, 57, and 58 that are connected within gearbox 21 respectively to belts 26, 38, and 27 (as shown in FIG. 3). It must be noted that illustrations for gears 56, 57, and 58 are merely representative, and different sizes, configuration, and numbers of gears may actually be used to fulfill the functions disclosed herein for gears 56, 57, and 58. In addition, FIG. 2c shows the manual control 22 for opening and closing probe arms 5 and 6 connected to gear 58. What is not shown in FIG. 2c is that control 22 is preferably connected through the hidden side of gearbox 21, as can be more clearly seen in FIG. 3.

FIG. 3 is an enlarged view of the gearbox 21 in the most preferred embodiment of the present invention having representative gears 56, 57, and 58, which may have different configurations in differing applications but for clarity of illustration have each been shown by a representation of a single gear. The multiple sets of gear identified by the number 56 and 57 are complementary to one another to achieve the appropriate pre-determined convergence ratio. Although shown in FIG. 3 on the same axle for simplification, in reality they are not. In many semi-automated application of the present invention a 100:1.5 ratio of convergence is preferred, which is roughly the calculated average in the examples of ratio of convergence calculations shown in FIGS. 35 and 36, but the ratio of convergence can be different for differing applications. FIG. 3 shows the outer shell 23 associated with main tubular shaft 2, and both depending outwardly from gearbox 21 (which can be attached to main tubular shaft 2 and outer shell 23 by conventional means—not shown), the manual control 22 connected to gear 58 and used for opening and closing probe arms 5 and 6, as well as the on-off switch 55 on gearbox 21 that is used to turn on the power source 76 to electromagnet 9, for remote disengagement of pinion gear 11 from rack 73 to allow adjustment ring 7 to move freely relative to the moving cylindrical sheath 1, and reset the moving cylindrical sheath 1 position to a primary/original position when diagnostic/sensor probes 3 and 4 are adjacent to one another. Disengagement of pinion gear 11 from rack 73 is also needed with initial insertion or removal of the distal end of the main tubular shaft 2 from a working space or cavity. On-off switch 55 is also used to turn off the electrical power to electromagnet 9, allowing pinion gear 11 to return to its engaged position with rack 73.

Figure 30:
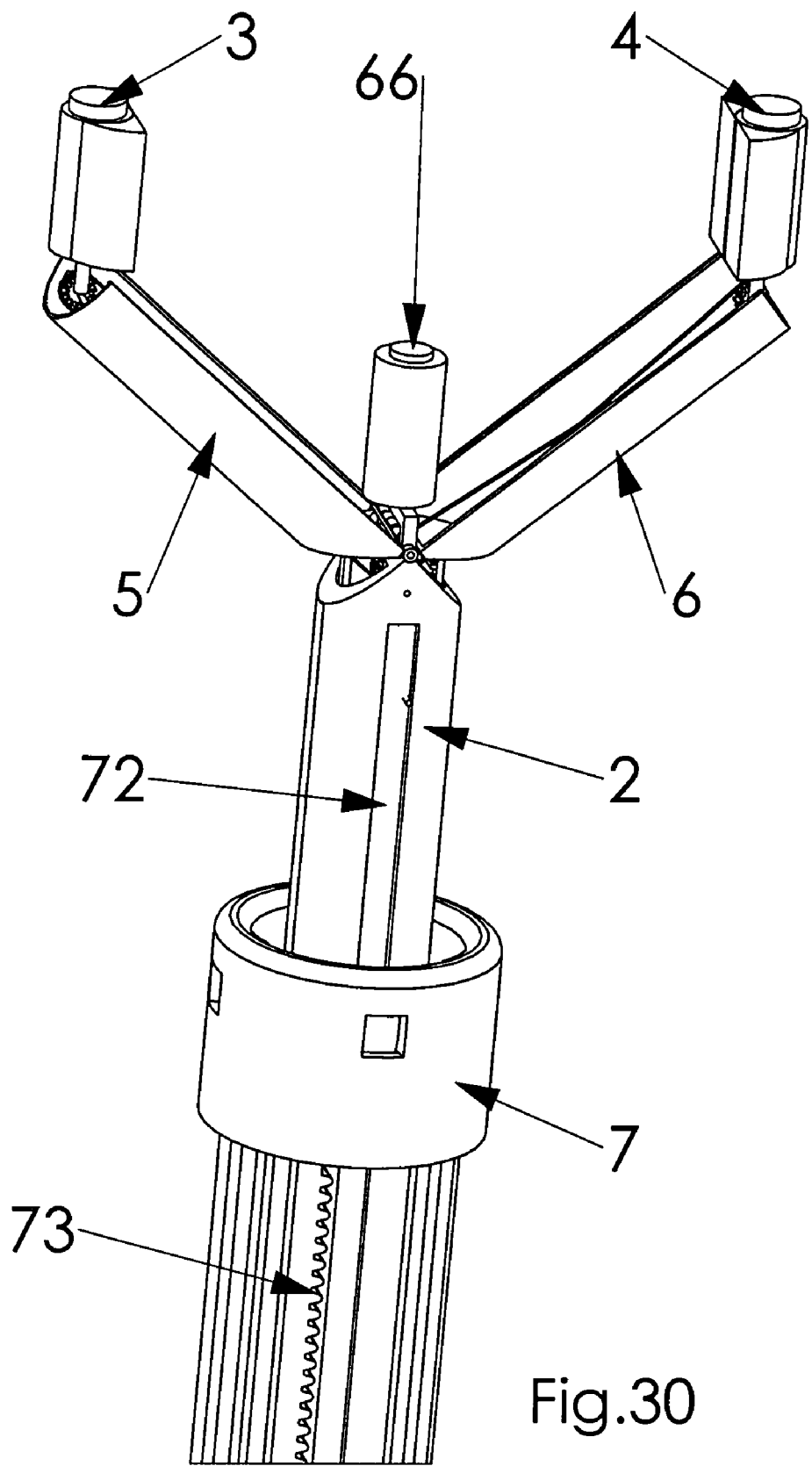
FIG. 30 is an enlarged view of the probe arms of the present invention in a partially opened position, with a centrally located unit mounted on the same hinge used for pivotally mounting the probe arms, with this unit being used for alignment purposes as a laser pointer in semi-automated configurations and as a target distance sensor in fully automated configurations.

FIG. 4 is a sectional view of the top end of the main tubular shaft 2 in the most preferred embodiment of the present invention showing the hinge 42 used to respectively mount the complementary hinge structures 25 and 24 on probe arms 5 and 6 (not shown in FIG. 4). As shown in FIG. 30, a shaft-to-target distance sensor or laser pointer 66 can also be connected to hinge 42. FIG. 4 further shows belt 27 engaging gear 29 within main tubular shaft 2, with gear 29 mounted on the same axis as the pinion gear 34 that engages and moves on the rack 48 of two-rod control assembly 47 to open and close probe arms 5 and 6. FIG. 4 also shows a first gear 30 engaging belt 38, which is on the same axis with a second gear 30 to which belts 36 and 37 are secured. It should be noted that belt 36 is crossed over itself into a figure-8 configuration, while belt 37 forms a simple loop. This structure assures movement of diagnostic/sensor probes 3 and 4 together in opposed directions. For example, instead of their gears 31 and 32 both turning in the same direction (clockwise), they turn in opposing directions (with one turning clockwise and the other one turning counterclockwise), thereby causing convergence of the diagnostic/sensor probes 3 and 4 on the same visual target. FIG. 4 also shows the attachment 70 on the distal end of the rack 48 on two-rod control assembly 47 that contacts probe arm 6 to move it out of the zero position, the attachment 71 on the distal end of one of the rods on two-rod control assembly 47 that contacts probe arm 5 to move it out of the zero position, the groove guide 90 that receives guide rail 89, guide rail 89 on main tubular shaft 2 (sets of two are on each side of main tubular shaft 2), and the angled top surface 83 of main tubular shaft 2 that in combination with angled bottom surfaces of probe arms 5 and 6 prevent the movement of probe arms 5 and 6 beyond a full opened configuration of 180 degrees.

Figure 6:
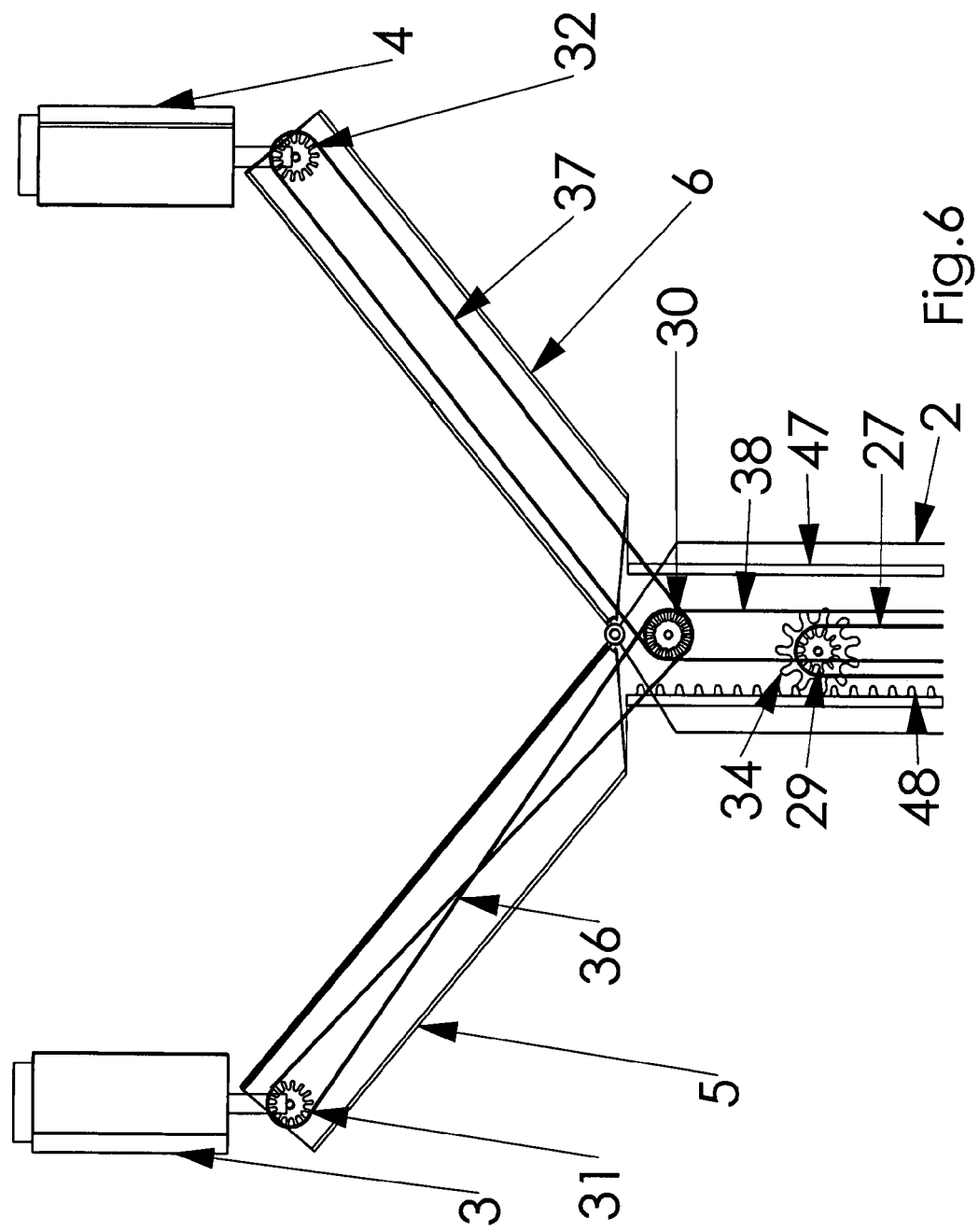
FIG. 6 is a sectional view of the most preferred embodiment of the present invention exposing the gears and belts that are used for diagnostic/sensor probe and two-rod control assembly movement to achieve 3-dimensional human vision simulated imaging with real dynamic convergence, with the probe arms shown in a partially opened position and the diagnostic/sensor probes displaying little or no convergence on a target object.
Figure 7:
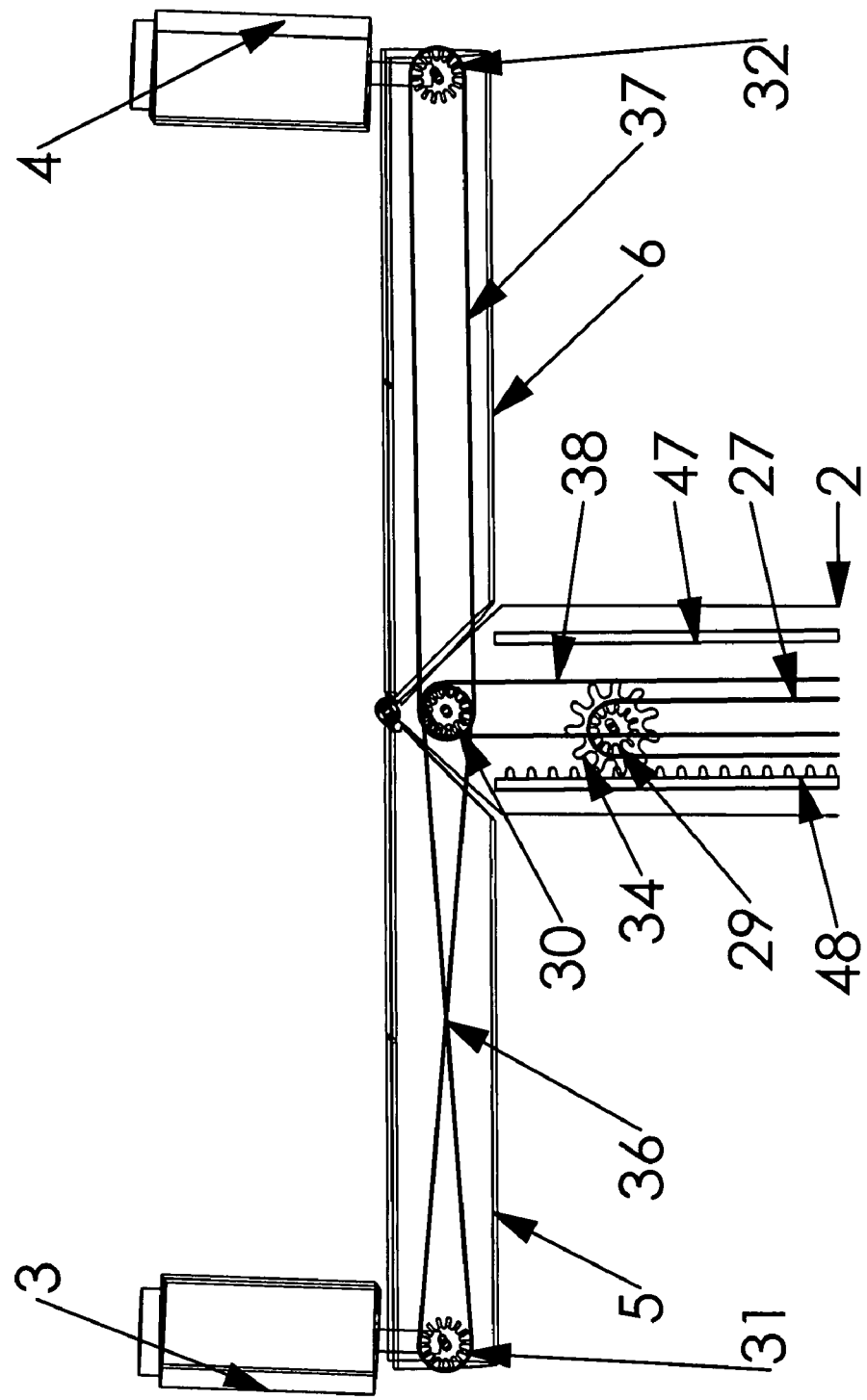
FIG. 7 is a sectional view of the most preferred embodiment of the present invention having probe arms fully opened in a 180 degree range of movement, with little or no convergence of the diagnostic/sensor probes on a target object, and some of the belts and gears visible that are used for probe arm and two-rod control assembly movement to achieve 3-dimensional human vision simulated imaging with real dynamic convergence.

FIGS. 5-7 show in more detail the structure needed for opening and closing probe arms 5 and 6 and for convergence of diagnostic/sensor probes 3 and 4. FIG. 5 is a side view of the most preferred embodiment of the present invention where two probe arms 5 and 6 are connected at their proximal ends (via the hinges marked in FIG. 2*a* respectively by the numbers 25 and 24) to a complementary hinge structure 42 on the top end of the main tubular shaft 2. One of the four channels 72 in main tubular shaft 2 is also shown, which helps to guide the movement of adjustment ring 7 and the moving cylindrical sheath 1 on main tubular shaft 2 using three sets of four rollers 50 each. Diagnostic/sensor probe 3 extends outwardly from the distal end of probe arm 5 and diagnostic/sensor probe 4 extends outwardly from the distal end of probe arm 6, and both diagnostic/sensor probes 3 and 4 are shown adjacent to one another in their primary/original position (also referred to herein as the zero position). FIG. 5 also shows probe mounting assembly 43 extending between diagnostic/sensor probe 3 and probe arm 5, with probe mounting assembly 44 extending between diagnostic/sensor probe 4 and probe arm 6. Further in FIG. 5, diagnostic/sensor probe gear 31 is shown associated with diagnostic/sensor probe 3 and diagnostic/sensor probe gear 32 is shown associated with diagnostic/sensor probe 4. Diagnostic/sensor probe gears 31 and 32 are shown in more detail in FIGS. 6 and 7. Between probe arm 5 and main tubular shaft 2, FIG. 5 shows a two-rod control assembly 47 (see enlarged view in FIG. 8) having a rack 48 (which is engaged by the pinion gear 34 shown in FIGS. 6 and 7) on one of its sides that is positioned between probe arm 6 and main tubular shaft 2. The two-rod control assembly 47 and rack 48 move into the interior of main tubular shaft 2 as probe arms 5 and 6 move toward their fully opened positions, which results in diagnostic/sensor probes 3 and 4 each moving 90-degrees from its primary/original position (or zero position). When the probe arms 5 and 6 are in the fully opened position, the angled proximal surfaces of probe arms 5 and 6 become positioned against the angled upper surface 83 of the distal end of main tubular shaft 2, as shown in FIGS. 7 and 12 (although angled surface 83 is not marked by a number in these views). It is the angled upper surface 83 of the main tubular shaft 2 that stops the range of movement of probe arms 5 and 6 away from one another to the 180-degree angle shown in FIG. 7. However, during use of the present invention probe arms 5 and 6 may be moved into any partially opened position having an angle between 0-degrees and 180-degrees. A 90-degree angle is shown in FIG. 6. The pinion gear 34 that engages the rack 48 of two-rod control assembly 47 is shown in FIGS. 6 and 7 and is responsible for the transmitted movement that opens and closes probe arms 5 and 6. FIGS. 6 and 7 are sectional views where belts 36 and 37 are visible respectively within probe arms 5 and 6, with belt 36 extending between gears 31 and 30 for affecting the movement of diagnostic/sensor probe 3 and belt 37 extending between the same gear 30 and gear 32 for affecting the movement of diagnostic/sensor probe 4. The connection of belts 36 and 37 to gear 30 is more clearly shown in FIG. 4. While FIG. 6 shows probe arms 5 and 6 in a partially opened position, FIG. 7 shows probe arms 5 and 6 fully opened in a 180 degree range of movement from one another. In FIGS. 6 and 7 belt 36 is shown crossed over itself to form a figure-8 configuration and belt 37 is shown forming a simple loop. This structure assures movement of diagnostic/sensor probes 3 and 4 together in opposed directions. Since the critical aspect of belts 36 and 37 is that only one of them will have a figure-8 configuration, the reverse situation where belt 37 is crossed over itself in a figure-8 configuration and belt 36 is in the form of a simple loop can also be considered within the scope of the present invention. FIGS. 6 and 7 also both show the two-rod control assembly 47 and its rack 48, and the pinion gear 34 that engages rack 48 to open and close probe arms 5 and 6, the smaller gear 29 that engages belt 27, and the belt 38 that extends through the main tubular shaft 2 and its associated outer shell 23 into gearbox 21 for transmitting the movement needed to achieve convergence. The positioning of rack 48 shown in FIGS. 6 and 7 should not be considered as limiting. Thus, instead of a positioning where the distal end of rack 48 is adjacent to probe arm 5 and would provide the force to move probe arm 5 out of the zero position, it is considered to be within the scope of the present invention for the position of the rack 48 in two-rod control assembly 47 to be reversed and instead provide such movement for probe arm 6. Similarly, the positioning of probe arms 5 and 6 and the diagnostic probes 3 and 4 can be reversed. Rack 48 is shown adjacent to probe arm 6 and the diagnostic/sensor probe 4 in FIG. 5, but close to probe arm 5 and the diagnostic/sensor probe 3 in FIGS. 6 and 7.

Figure 8:
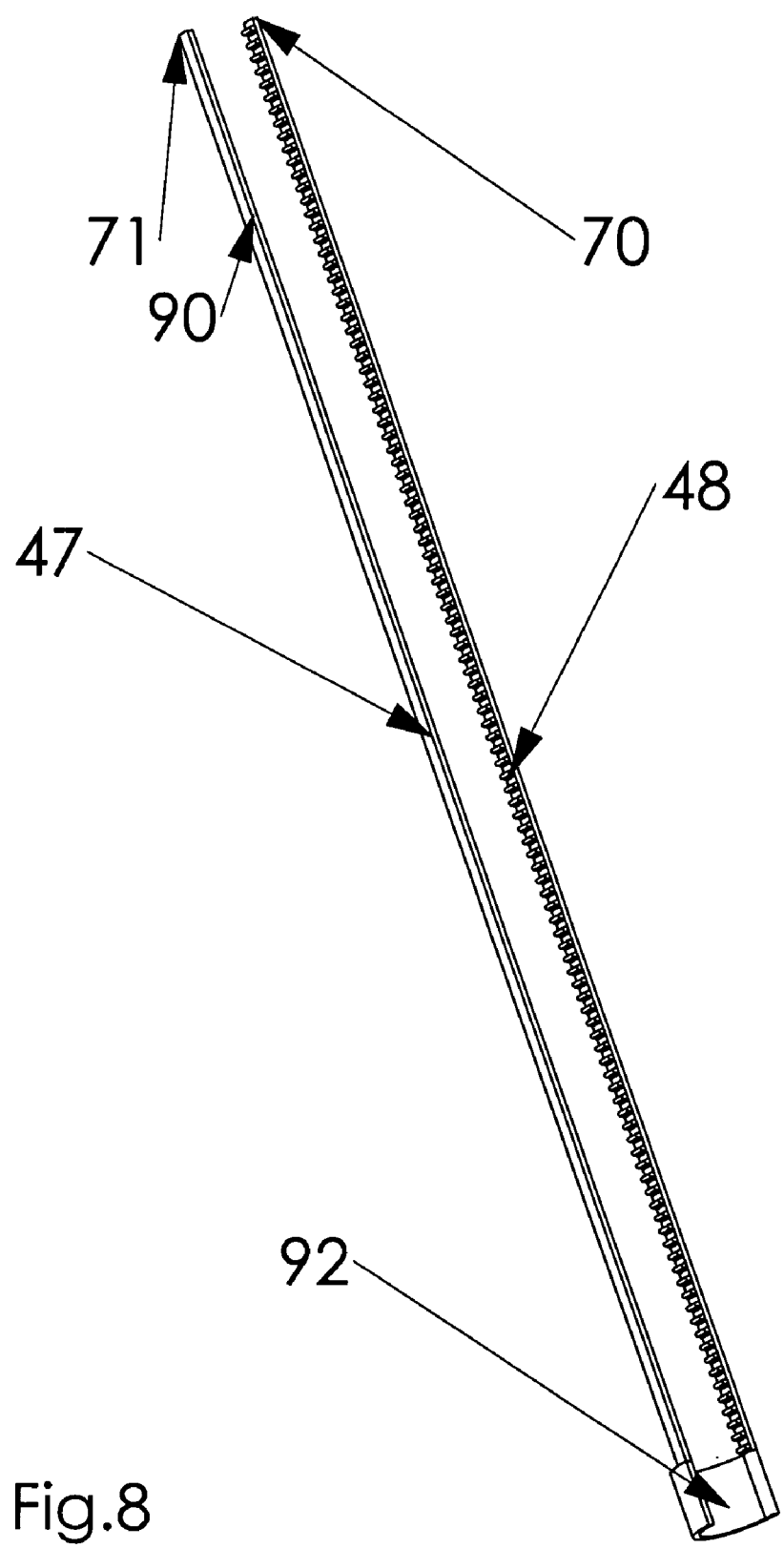
FIG. 8 is a side view of the two-rod control assembly and linear gear used in the most preferred embodiment of the present invention for opening and closing the probe arms.

FIG. 8 is an enlarged side view of the two-rod control assembly 47 and its rack 48 used in the most preferred embodiment of the present invention for opening and closing probe arms 5 and 6. As mentioned in the paragraph immediately above, rack 48 could be located in an opposed position from that shown, as long as the pinion gear 34 that engages it is repositioned as needed for proper engagement therewith and function. FIG. 8 also identifies the attachment 70 on the distal end of the rack 48 on two-rod control assembly 47 that contacts probe arm 6 to move it out of the zero position, the attachment 71 on the distal end of one of the rods on the two-rod control assembly 47 that contacts probe arm 5 to move it out of the zero position. In addition, FIG. 8 shows the groove guide 90 that receives one of the four guide rails 89 on main tubular shaft 2. As shown in FIG. 4 (although none of the four groove guides 90 is individually numbered for clarity of illustration), two opposing groove guides 90 are present on the top of rack 48 and two groove guides 90 are also present on the top of rod 47 that is located directly under the top part of belt 37. As visible in FIG. 8, it is contemplated for groove guides 90 to extend longitudinally along the full length of rack 48 and rod 47. Thus, two sets of two guide rails 89 (only one of which is shown in FIG. 4) are on each side of main tubular shaft 2, each one aligned with a different one of the four groove guides 90 on rack 48 and rod 47. Further, as shown in FIG. 8, rack 48 and rod 47 are joined together by an arcuate proximal end 92.

FIGS. 9-14 show more detail in the connection of diagnostic/sensor probes 3 and 4 to probe arms 5 and 6, and probe arms 5 and 6 to main tubular shaft 2. FIG. 9 is an enlarged view of diagnostic/sensor probe 3 in the most preferred embodiment of the present invention. One side of diagnostic/sensor probe 3 is marked by the number 41, which represents a light source that can include fiber-optic means, one or more LED lights, and/or other source of light that has a compact configuration and is also sufficiently bright without the generation of surplus heat beyond that tolerable in the intended application. The other side of diagnostic/sensor probe 3 is marked by the number 40, which represents one or more additional imaging or therapeutic features, such as but not limited to a camera, ultra-sound device, treatment laser, or therapeutic radiation, radio-frequency dispensing unit. In the alternative, to meet the needs of an application and as current technology permits, therapeutic features may be incorporated into the space occupied by diagnostic/sensor probe 3 and/or 4 in FIGS. 9 and 10, with the imaging sensors (camera, ultrasound, and the like) positioned in the space in FIGS. 9 and 10 marked by the number 40 or 41. The combined configuration of diagnostic/sensor probe 3, light source 41, and additional imaging or therapeutic feature or features 40 preferably is a half-cylinder with a smooth arcuate perimeter that facilitates use of the present invention device in medical applications through a endoscopic port. However, a circular cross-sectional configuration is not critical, particularly for non-medical applications, and it is also considered to be within the scope of the present invention for the combined configuration of diagnostic/sensor probe 3, light source 41, and additional imaging or therapeutic feature or features 40 to be that of an ellipse, half-hexagon, half-octagon, or other polygonal shape with angles of approximately 60-degrees or less, or any other shape that will fit the diagnostic/sensors probes and/or the therapeutic or any control features needed for the application and still fits the entry port for the space or cavity. FIG. 9 also shows diagnostic/sensor probe 3 supported by mounting assembly 43, the axle 68 of which supports the diagnostic/sensor probe gear 31 that engages belt 36 and is responsible for moving the combined diagnostic/sensor probe 3, light source 41, and additional imaging or therapeutic feature or features 40 during convergence. Axle 68 is identified by its assigned number in FIG. 12. Although not shown in an enlarged view similar to that provided by FIG. 9, from other illustrations provided herein one can see that diagnostic/sensor probe 4 in the most preferred embodiment of the present invention is also associated with a light source 41 and an additional imaging or therapeutic feature or features 40, and is similarly supported by a mounting assembly 44 that has an axle 68 which supports the diagnostic/sensor probe gear 32 engaging belt 37. FIG. 10 is a top view of the two diagnostic/sensor probes 3 and 4 in the most preferred embodiment of the present invention in their fully-closed zero position, prior to convergence on a target object 59. FIG. 10 also shows the preferred no-angled perimeter for the combined diagnostic/sensor probes 3 and 4, light sources 41, and additional imaging or therapeutic features 40 used in the most preferred embodiments of the present invention. FIGS. 11-14 also show diagnostic/sensor probes 3 and 4 each with an associated light source 41 and an additional imaging or therapeutic feature or features identified by the number 40, with diagnostic/sensor probes 3 and 4 respectively mounted for convergence movement upon the distal end of probe arms 5 and 6, and probe arms 5 and 6 joined together on the distal end of main tubular shaft 2 by hinge 42. In addition, FIGS. 11-14 also show main tubular shaft 2 extending beyond the distal end of adjustment ring 7, with the projections rods 69 and rack 73 of adjustment ring 7 extending in the opposite direction. The two of the four longitudinal channels 72 in the external face of main tubular shaft 2 are shown in FIGS. 12-14. Further, although spaced-apart unnumbered rectangular holes are shown in FIGS. 11-14 through adjustment ring 7, for are for design purposes only and their presence is not required. As a result, their shape, configuration, number, and location should not be considered critical. Also, while FIGS. 11-13 show the same mounting means for diagnostic/sensor probes 3 and 4, FIG. 14 reveals an alternative mounting means that includes alternative axle mounts 67 and springs 39. This configuration is used if belts 36 and 37 are made of non-stretchable materials, to compensate for the difference in the length of belts 36 and 37 required for different opening and closing positions of probes arms 5 and 6. It is also needed since probe arms 5 and 6 and the gear 30 engaging belts 36 and 37 do not have a common axis. The axis for each probe arm 5 and 6 passes through the center of the combined hinge structure of 24, 25 and 42, while the belts 36 and 37 turn on the axis of their associated gear 30.

FIGS. 11-13 are distinguished from one another in that FIG. 11 is a perspective view of diagnostic/sensor probes 3 and 4 in a partially opened position, FIG. 12 is a perspective view of diagnostic/sensor probes 3 and 4 in a fully opened position, and FIG. 13 is a perspective view of diagnostic/sensor probes 3 and 4 in a partially opened position that is rotated approximately 90-degrees from the view shown in FIG. 11 so that a comparison can be made to the similar orientation of probe arms 5 and 6 shown in FIG. 14. FIGS. 11-14 also show a portion of the inside distal surface of each probe arm 5 and 6 being removed to reveal the preferred internal positioning of the belts 36 and 37, with belt 36 being crossed over on itself into a figure-8 configuration and belt 37 forming a simple loop. FIGS. 11-13 show the top surfaces 83 of probe arms 5 and 6 removed wherein mainly in probe arm 5 one can see the axle 68 that supports gear 31 and the un-numbered upright portion of mounting assembly 43 (shown in greater detail in the enlarged view of FIG. 9). In contrast, FIG. 14 show a set of four alternative axle mounts 67 for each diagnostic/sensor probe 3 and 4 that are used in pairs, with each pair holding a longitudinally-extending compressed spring 39 configured to bias the axle 68 to which diagnostic/sensor probe gear 31 or 32 is secured toward the distal end of its associated probe arm 5 or 6.

Figure 22:
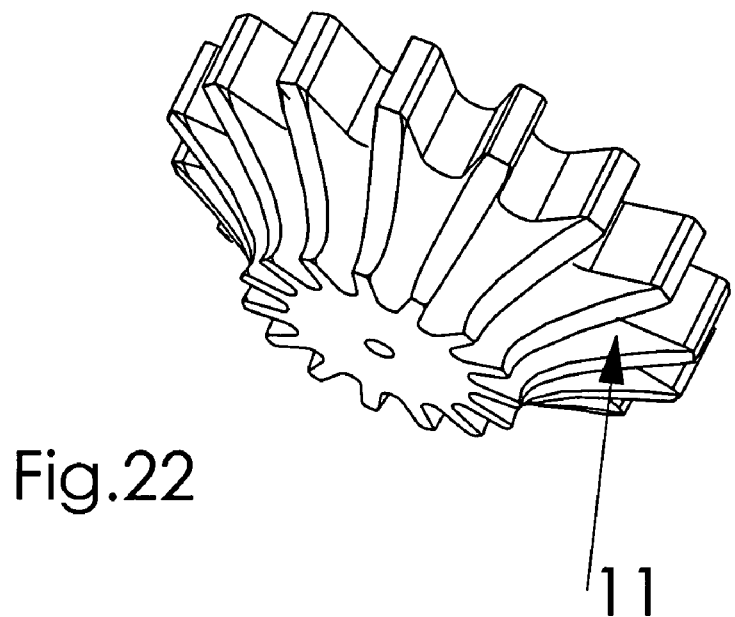
FIG. 22 is a perspective view of the cone-shaped gear in the most preferred embodiment of the present invention used between the rotatable manual control and the linear gear of the adjustment ring.

FIGS. 15-22 reveal more information about moving cylindrical sheath 1 and its association with adjustment ring 7 and the projection rods 69 and rack 73 connected between adjusting ring 7 and its proximal end 46, including the separated configuration of proximal end 46 that is shown in FIGS. 19a and 19b. FIG. 15 is a perspective view of the most preferred embodiment of the present invention with the distal end of the moving cylindrical sheath 1 in a position remote from the viewer, with FIG. 16 showing moving cylindrical sheath 1 and adjustment ring 7 rotated approximately 180-degrees so that the proximal end of moving cylindrical sheath 1 is in a remote position from the viewer. FIG. 17 shows a sectional view showing adjustment ring 7 positioned for sliding movement within moving cylindrical sheath 1, with FIG. 18 showing an enlarged sectional view of the rotatable manual control 8 and the electromagnet 9 (housed within the rotatable manual control 8) for releasing pinion gear 11 from the rack 73 of adjustment ring 7 to allow adjustment ring 7 to move freely relative to moving cylindrical sheath 1, wherein diagnostic/sensor probes 3 and 4 are permitted to return to their zero position with zero convergence. In addition, FIGS. 19a and 19b show adjustment ring 7 from each of its ends for more clarity of disclosure, FIG. 20 shows moving cylindrical sheath 1 without adjustment ring 7, FIG. 21 shows an end view of moving cylindrical sheath 1 to more clearly reveal the positioning of grooves 74 and 75 as well as the arcuate projections 51 that each secure a roller 50 into its position of use, and FIG. 22 shows an enlarged view of cone-shaped gear 11. Further, it must be recognized by a viewer that the illustrations of electrical wiring 13, on-off switch 55 (that is connected to gearbox 21), power source 76, and electromagnet 9 in FIGS. 15, 16, 20, and 21 are merely representative and not indicative of actual size or configuration. In the same manner, the illustrations of electrical wiring 13, on-off switch 55 (un-numbered), and power source 76 (also un-numbered), in FIG. 17 are also merely representative of that structure. FIGS. 15 and 16 show the projection rods 69 and rack 73 of adjustment ring 7 extending into moving cylindrical sheath 1, with FIG. 16 showing projection rods 69 and rack 73 respectively guided in its movement into moving cylindrical sheath 1 by the grooves marked by the numbers 74 and 75 in FIG. 21. FIGS. 15 and 16 also show one of the pair of opposing longitudinal slots 33 in moving cylindrical sheath 1 that guides the movement of moving cylindrical sheath 1 within the outer shell 23 associated with main tubular shaft 2 via the assistance of the radially-extending brace 85 securing outer shell 23 to the main tubular shaft 2 (as shown in FIG. 26) so that so they would not block the movement of the moving cylindrical sheath 1. In addition, FIGS. 15 and 16 show the rack 86 on moving cylindrical sheath 1 used with pinion gear 54, the rotatable manual control 8 used to control the cone-shaped gear 11 that engages rack 73 to allow the back and forth movement of adjustment ring 7 relative to moving cylindrical sheath 1, and the remote means of disengaging pinion gear 11 from rack 73 that involves the use of on-off switch 55, power source 76, and the electrical wiring connecting switch 55 and power source 76 to the electromagnet 9 housed within the rotatable manual control 8 (shown in FIGS. 18 and 19). FIG. 16 also shows the rollers 50 that allow smooth back and forth movement of adjustment ring 7 on main tubular shaft 2 and one un-numbered roller 50 (part of a set of four rollers 50) associated with moving cylindrical sheath 1 for its smooth back and forth movement on main tubular shaft 2. Although the number of rollers 50 used is not critical, it is preferred for four rollers 50 to be associated with the distal end of adjustment ring 7, as well as each end of the moving cylindrical sheath 1. Similar to the un-numbered rectangular holes in adjustment ring 7 that were previously mentioned in the discussion of FIGS. 11-14 for purposes of this disclosure the presence of the un-numbered rectangular holes in the ends of moving cylindrical sheath 1 are not needed and, as a result, their shape, configuration, number, and location should not be considered critical. FIGS. 17 and 18 show more detail about the connection of rotatable manual control 8 through moving cylindrical sheath 1 for engagement of pinion gear 11 to the rack 73 of adjustment ring 7. The three sets of four rollers 50 each are also shown in FIG. 17, which are used in association with the distal end of adjustment ring 7 and each end of moving cylindrical sheath 1. FIG. 17 also shows the rack 86 in moving cylindrical sheath 1 that engages pinion gear 54, the proximal end 46 of adjustment ring 7 within moving cylindrical sheath 1, and the spring 49 that extends between the proximal end of moving cylindrical sheath 1 and the radially-extending brace 85 on main tubular shaft 2. The connection of rotatable manual control 8 through moving cylindrical sheath 1, with its associated spring 12 and the electromagnet 9 (that via electrical wiring 13 is connected to remotely located on-off switch 55 and power source 76) is shown broadly in FIG. 17, but in more detail in the enlarged sectional view of FIG. 18. The rollers 50 associated with the distal ends of adjustment ring 7 and moving cylindrical sheath 1 are also illustrated in FIG. 18 (with FIG. 23 providing an enlarged view that shows the axles of two rollers 50 mounted on both structures. FIG. 18 further shows the rack 86 of the moving cylindrical sheath 1 (that engages the pinion gear 54 shown in FIGS. 2b and 17) and pinion gear 11 engaged with the rack 73 of the adjustment ring 7 that is needed for manual convergence movement of diagnostic/sensor probes 3 and 4 when needed. FIGS. 19a and 19b show the structure of adjustment ring 7, with FIG. 19a clearly showing four projection rods 69 extending in pairs each to a separate portion of proximal end 46. The proximal end 46 of adjustment ring 7 must be separated in this manner to provide clearance for the radially-extending brace 85 of main tubular shaft 2 as adjustment ring 7 moves back and forth on main tubular shaft 2. Although FIGS. 19a and 19b show the rack 73 of adjustment ring 7 as a separate structure from projection rods 69, it is considered within the scope of the present invention for rack 73 to be associated with at least one projection rod 69. FIG. 20 shows moving cylindrical sheath 1 without adjustment ring 7, to reveal the arcuate projections 51 that each secures a roller 50 into its desired position of use. FIG. 20 further shows opposing slots 33, with the upper slot 33 having an associated number and the opposed lower slot remaining un-numbered but visible though the distal end of moving cylindrical sheath 1 in a position immediately to the left of the continuation of rack 86. As also seen in FIG. 21, FIG. 20 shows the electromagnet 9 that is housed in rotatable manual control 8 (see FIG. 18) and its associated electrical wiring 13, on-off switch 55, and power source 76. FIGS. 20 and 21 also both show the distal end of moving cylindrical sheath 1 with the groove 75 for guiding the movement of the rack 73 of adjustment ring 7, the four grooves 74 that each guides one of the projection rods 69 of adjustment ring 7, and the arcuate projections 51 that each secures a roller 50 into its desired position of use. FIG. 22 simply shows the preferred generally cone-shaped configuration of the pinion gear 11 used with rack 73.

FIGS. 23-25 show the structure and use of rollers 50 in the most preferred embodiment of the present invention in greater detail. FIG. 23 is an enlarged sectional view of the distal end of adjustment ring 7 with two of the four preferred rollers 50 used therewith shown positioned between the interior surface of adjustment ring 7 and the exterior surface of main tubular shaft 2. Although rack 73 is shown attached to adjustment ring 7, the projection rods 69 have been omitted for clarity of illustration. One of the rollers 50 shown has an associated spring 60 that is used to bias roller 50 against the exterior surface of main tubular shaft 2, and although a spring 60 would also be used with the other roller 50, the second spring 60 has been removed to reveal the projection 51 that depends outwardly from the interior surface of adjustment ring 7 and is employed to mount spring 60 in its position of use. FIGS. 24 and 25 show an enlarged view of a roller 50 in the most preferred embodiment of the present invention, with FIG. 24 spring 60 associated centrally with roller 50 and FIG. 25 showing the centrally located opening 52 in roller 50 configured for receipt of the arcuate projection 51 upon which spring 60 is mounted. One of the four elongated channels 72 in main tubular shaft 2 is also shown in FIG. 23 that help to guide the movement of adjustment ring 7 and the moving cylindrical sheath 1 on main tubular shaft 2. It is contemplated in the most preferred embodiment of the present invention for the rollers 50 between both ends of moving cylindrical sheath 1 and the main tubular shaft 2 to be mounted in a similar configuration and by similar means to that shown in FIG. 23.

FIG. 26 is an enlarged sectional view of the distal part of outer shell 23 associated with the main tubular shaft 2, with main tubular shaft 2 positioned within the proximal end of the moving cylindrical sheath 1. This is the portion of the present invention where the back or forth movement of moving cylindrical sheath 1 on main tubular shaft 2 (that corresponds to the movement of the distal end of main tubular shaft 2 toward or away from the target visual object) is transmitted through its linear gear 86 to the pinion gear 54 engaging it. Since pinion gear 54 is mounted on an axle extending through the main tubular shaft 2 that provides a mount for gear 28 (but gear 28 is positioned inside main tubular shaft 2, while pinion gear 54 is mounted outside main tubular shaft 2), the movement of pinion gear 54 is then transmitted via the gear 28 to a belt 26 that sends the movement to gearbox 21. After the incoming movement is reduced an appropriate amount within gearbox 21 by a set of multiple gears 56, other mechanical structure of the present invention transmits the reduced movement from the moving cylindrical sheath to the diagnostic/sensor probe gears 31 and 32 to actuate the proper amount of convergence. FIG. 26 further shows the pinion gear 54 engaging rack 86 within moving cylindrical sheath 1. In addition, although its top and bottom connections are not shown, the belt 38 that is positioned within main tubular shaft 2 (for transmitting movement between gearbox 21 and gear 30) is also shown in FIG. 26 to the left of belt 27. The radially-extending brace 85 that connects outer shell 23 to the main tubular shaft 2 is shown engaging the opposed longitudinally-extending slots 33 in moving cylindrical sheath 1. FIG. 26 also shows one of the four elongated channels 72 in the exterior surface of main tubular shaft 2 that help to guide the movement of adjustment ring 7 and the moving cylindrical sheath 1 on main tubular shaft 2.

Figure 27:
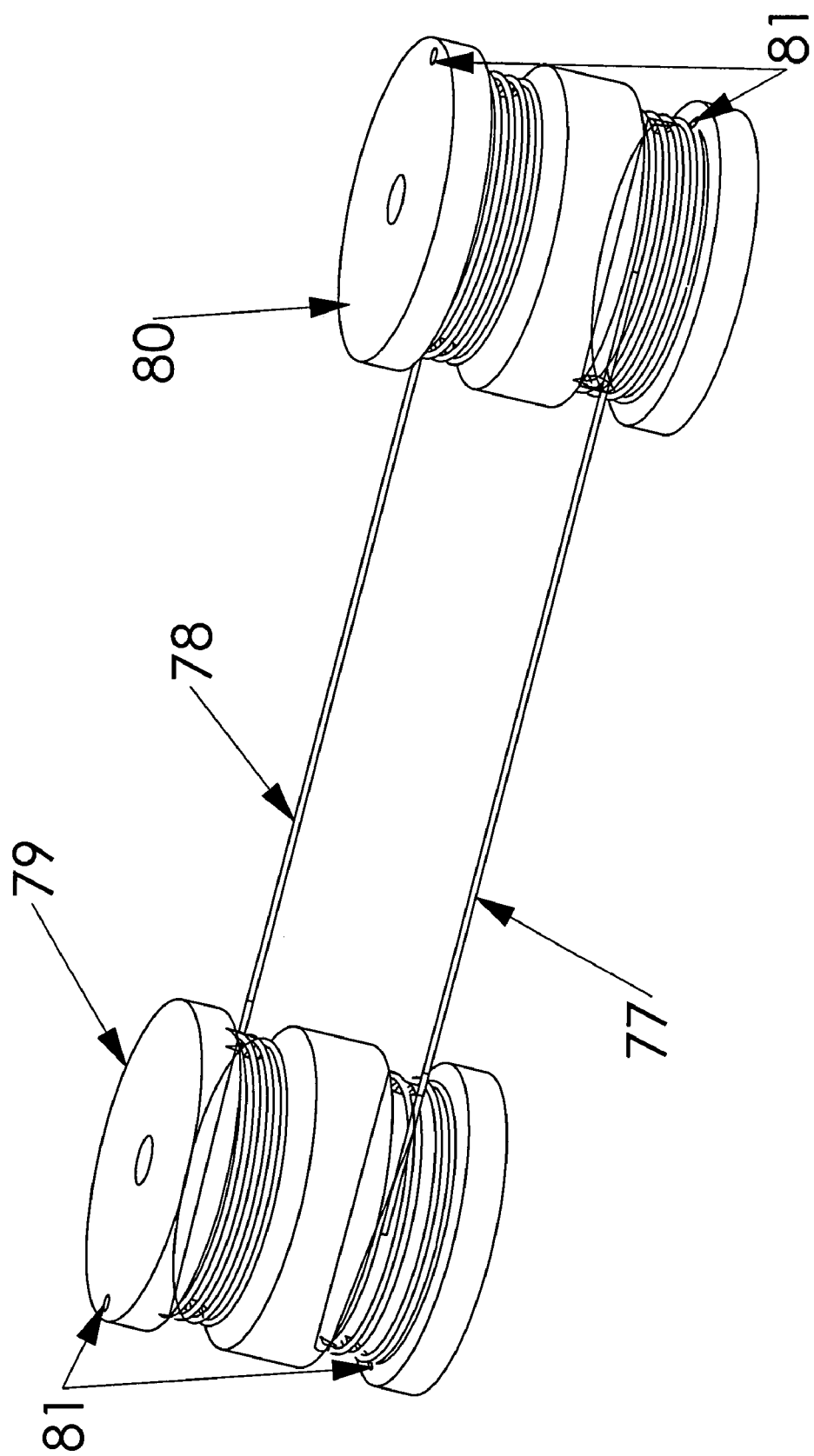
FIG. 27 is a perspective view of an alternative pulley system that can be used for movement of the probe arms, and which can be substituted for many of the gear-and-belt systems, as well as pinion-and-rack gear systems, of the present invention.

FIG. 27 is a perspective view of an alternative pulley system in the most preferred embodiment of the present invention for use in place of any belt and gear combination that provides outward and return movement to one location. One example of its use is to the replace belt 36 and gear 31, or belt 37 and gear 32, to prevent slippage, provide more precision and accuracy, and/or provide a stronger system for high stress applications. However, this alternative pulley system can be substituted for the majority of the gears and belts systems of this invention, with or without teeth (not shown) implemented on the pulley system to allow the pulley to engage other gears whether linear or circular. This particular pulley system configuration is used when high level of accuracy in transmission of movement is required because it is configured to minimize chances of slipping between the pulleys (79 and 80) and the cables (77 and 78) connected to them also when an exact limited numbers of revolutions and turns of the gear system are required for the application (which is controlled by the number of loops that the cable is looped on each pulley 79 and 80 at the time the pulley system was made before its initial usage). This alternative pulley system comprises a first double pulley 79 with a pair of independent winding grooves and a second double pulley 80 with identical configuration. To prepare first double pulley 79 and second double pulley 80 for use, one end of a first flexible but non-stretchable cable 77 is anchored to first double pulley 79 adjacent to one of its winding grooves and then looped around the adjacent winding groove a pre-determined number of times. First double pulley 79 is then aligned with second pulley 80 and placed at the needed spaced-apart distance from second pulley 80 dictated by the application. After first flexible but non-stretchable cable 77 is extended across the spaced-apart distance to second pulley 80, it is looped the same pre-determined number of times around the opposed winding groove in second pulley 80, after which it is anchored to second double pulley 80. A second flexible but non-stretchable cable 78 is similarly anchored and looped around the unused set of opposed winding grooves in double pulleys 79 and 80. Since cables 77 and 78 do not stretch, springs would provide and needed bias in the connection, such as the use of springs 39 (see FIG. 14) should the alternative pulley system shown in FIG. 27 be used to replace belt 36 and gear 31, or belt 37 and gear 32. FIG. 27 also shows first double pulley 79 and second double pulley 80 each having a cable attachment end point 81, one for each cable 77 and 78. It is contemplated for attachment points 81 to be merely representative. As a result, the size and relative position shown in FIG. 27 on first double pulley 79 and second double pulley 80 should not be considered limiting.

FIGS. 28*a*, 28*b*, and 28*c* show main tubular shaft independent from moving cylindrical sheath 1 and adjustment ring 7. FIGS. 28*a*-28*c* show the radially-extending brace 85 that connects main tubular shaft 2 to its associated outer shell 23, although in FIGS. 28*a* and 28*b* radially-extending brace 85 does not have a numerical designation. In each illustration, outer shell is shown to have a diameter dimension approximately three times that of the main tubular shaft 2, and extend over more than one third, but less than one-half of the length dimension of main tubular shaft 2. Although such dimensions are preferred, they should not be considered limiting. FIG. 28*b* shows the main tubular shaft 2 in the most preferred embodiment of the present invention in its most basic form connected to outer shell 23 via radially-extending brace 85. In contrast, FIG. 28*a* shows a handle 20 depending from outer shell 23 close to brace 85 that in combination with outer shell 23 is used for enhanced convenience in operator manipulation of the present invention device. However, handle 20 is not critical, and in the alternative an operator can maneuver the present invention using gearbox 21 and outer shell 23. FIG. 28*c* is a sectional view showing the radially-extending brace 85 at both ends of the outer shell 23 to provide a stable connection between it and main tubular shaft 2. The positioning of both braces 85 are also shown in FIGS. 1, 2*b*, and 2*c*, but the braces 85 connecting the proximal ends of main tubular shaft 2 and outer shell 23 are not shown in FIG. 28*a* or 28*b*. The radially-extending brace 85 that is shown closer to gearbox 21 could be used in the attachment of gearbox 21 to outer shell 23, although the use of such a connection should not be considered limiting since other common ways of connecting outer shell 23 to gearbox 21 are also considered to be within the scope of the present invention. FIG. 28*b* is a side view of the main tubular shaft in the most preferred embodiment of the present invention without a handle where an operator holds the device mainly using outer shell 23. Although a channel 72 is shown on the exterior of each illustration 28*a*, 28*b*, and 28*c*, it is not given a numerical designation in any of them. The main tubular shaft 2, and any other needed parts of the invention, can be adapted and/or otherwise configured from materials and may have joints that allow flexibility for navigation inside the cavity or space intended for its use, with the further incorporation of control means that allow an operator to control the direction the device will ultimately travel, for example up or down, to the left or right. This adaptation is particularly useful in spaces or cavities that are too irregular for straight or rigid endoscopes (or the like) to easily travel through.

FIG. 29 is a schematic view of the fully automated configuration of real convergence achievable in the most preferred embodiment of the present invention when a very high level of convergence accuracy is continuously needed in diagnostic/sensor probes 3 and 4 for certain applications. FIG. 29 shows a target distance sensor 66 connected to the distal tip of a main tubular shaft 2 (shortened for illustrative purposes only). The two diagnostic/sensor probes 3 and 4 for which convergence changes are required, and the target distance sensor 66, all provide positioning information input to a computer 15, which then recognizes when a change is needed by causing a motor 14 to open or close the size-adjustable gear 18+88, which in combination with the multiple set of gears 56 in the gear box 21 changes the ratio of convergence applied to the linear movement transmitted from the moving cylindrical sheath 1 to the gear box 21, and then after reduction is transmitted via gear 58 from gear box 21 to the diagnostic/sensor probe gears 31 and 32 to achieve the needed amount of convergence. In contrast, in the alternative semi-automated configuration of the present invention (which is used in the majority of the applications), the size-adjustable gear 18+88 is not provided and the ratio of convergence is calculated and predetermined before the manufacture of the device, so that the gear sizes and shapes can be selected according to the transformation ratio calculations. As shown in FIG. 29, information for the fully automated configuration of real convergence must be provided to computer 15, including the identification of the current position (amount of convergence) of at least one of the two diagnostic/sensor probes 3 and 4 on its axis, as well as the distance the target distance sensor 66 is from a target object 59. Information feedback from the size-adjustable gear 18+88 relating to its current size is also sent to a computer 15. To meet precision convergence needs, using the information it receives, computer 15 frequently calculates the amount of movement still needed in size-adjustable gear 18+88 to achieve proper convergence and then activates an electromagnet 16 to produce resistance in the turning movement of the size-adjustable gear (18+88) to allow the uniformly increasing diameter threading 17 of rod 19 to move within the size-adjustable gear (18+88) to turn and change its diameter dimension a calculated amount. Another sensor (not shown) in the size-adjustable gear (18+88) will send feedback information to computer 15 when the required change in the size-adjustable gear (18+88) is obtained so that computer 15 knows when to turn off electromagnet 16 and electric motor 14. Thus, the incoming linear movement from the moving cylindrical sheath 1 is transmitted to the set of multiple gears 56, and from the set of multiple gears 56 to the adjustable diameter gear portion 53 of the size-adjustable gear 18+88 (which now has the appropriate adjusted diameter for convergence). From gear portion 53, the movement is transmitted to the fixed diameter gear portion 45 of the size-adjustable gear 18+88, and then to the multiple set of gears 57, after which it is transmitted mechanically to diagnostic/sensor probed gears 31 and 32. As better seen in FIGS. 31-34, the size-adjustable gear (18+88) has an upper part 88 and a lower part 18 that are secured together by a hinge 61. Size-adjustable gear (18+88) also has a conical-shaped threaded core 62 and an adjoining threaded core of uniform diameter (not separately numbered). Hinge 61 allows the halves of the size-adjustable gear (18+88) to open and close relative to one another, and thereby change its size and power so that the rod 19 with its uniformly increasing diameter threading 17 can be moved through the conical-shaped threaded core 62 of the size-adjustable gear (18+88) for an increase or decrease in convergence of diagnostic/sensor probes 3 and 4. The transmission of the mechanical movement through the pre-determined set of gears into the size-adjustable gear, then 45 to gears 31+32 to cause convergence.

FIG. 30 is an enlarged view of the probe arms 5 and 6 of the most preferred embodiment of the present invention in a partially opened position and a target distance sensor or laser pointer 66 mounted centrally on the same hinge 42 (unmarked in FIG. 30, but shown with numerical designation in FIGS. 11-13) from which the probe arms 5 and 6 pivot. A laser pointer can be used to assist in the alignment of the longitudinal axis of the main tubular shaft 2 with the target visual object (such as 59) to help accomplish the initial manual convergence of diagnostic/sensor probes 3 and 4 in an efficient and rapid manner using the rotatable control 8 to adjust the position of the adjustment ring 7. In contrast, a target distance sensor is used in the fully automated configuration to give computer 15 the information needed for calculation of the appropriate ratio of convergence. When mounted on the same axis as hinge components 42, 24 and 25 and although not shown, it is preferred for the proximal end of target distance sensor or laser pointer 66 to have a complementary configuration to the other three hinge components so that all four complement one another. It is important for convergence calculations that target distance sensor 66 be mounted centrally on the distal end of the main tubular shaft 2. FIG. 30 also shows one of the four channels 72 on main tubular shaft 2, the rack 73 of adjustment ring 7, and the proximal end of main tubular shaft 2 extending into adjustment ring 7. The relative size and configuration of target distance sensor or laser pointer 66, as compared to that of diagnostic/sensor probes 3 and 4 and probe arms 5 and 6, is merely representative in FIG. 30 and configurations and sizes other than that shown are also contemplated.

FIGS. 31-34 show the structure and operation of the size-adjustable gear 18+88 located in gearbox 21 (see FIGS. 2c and 3) in preferred embodiments of the present invention having fully automated convergence. Although only one size-adjustable gear 18+88 is shown, more than one can be used. Further, it is not contemplated for the present invention endoscopic device having fully automated convergence to be limited to the use of the size-adjustable gear 18+88 shown and described herein. Thus, any mechanical unit that can perform the same function of controlling or adjusting the amount of movement that can be transmitted through it, can also be used. FIG. 31 is an enlarged view of the size-adjustable gear 18+88 in a fully closed position, with its upper part 88 connected to its bottom part 18 via hinge 61. FIG. 31 also shows the conical-shaped threaded core 62 provided jointly on the interior surfaces of upper part 88 and bottom part 18. The end of core 62 remote from the viewer opens into an adjoining threaded core of uniform diameter which is formed only by the bottom part 18 of the size-adjustable gear 18+88 (as shown more clearly in FIG. 32b) and which also forms the core of the fixed diameter gear portion 45 into which the uniform threading 65 on rod 19 (shown in FIG. 33) is inserted. In addition, FIG. 31 shows two openings 64 through upper part 88 and two arcuate projections 63 each connected to lower part 18 and extending through a different one of the openings 64. Arcuate projections 63 guide the movement of upper part 88 as it opens and closes. FIG. 31 also shows each arcuate projection 63 having a spring 60 thereon that biases upper part 88 back into its original closed position against lower part 18. FIGS. 32a and 32b, as well as FIG. 34, show size-adjustable gear 18+88 with each arcuate projection 63 extending through a different one of the openings 64 in upper part 88, but without springs 60 on arcuate projections 63 for enhanced clarity of illustration. In FIG. 32a size-adjustable gear 18+88 is in its fully closed position and in FIG. 32b size-adjustable gear 18+88 is in a partially opened position. FIG. 32a is a side view of the size-adjustable gear 18+88 in the most preferred embodiment of the present invention showing the exterior surface of the adjustable portion 53 of size-adjustable gear 18+88 situated between the two arcuate projections 63. Further, positioned adjacent to the left arcuate projection 63 of size-adjustable gear 18+88, FIG. 32a also shows the fixed diameter gear portion 45 of size-adjustable gear 18+88 that is only connected its lower part 18. In automated convergence adjustments, as electromagnet 16 is activated by computer 15, the movement of fixed diameter portion 45 will be impeded, wherein the truncated-cone-shaped portion of rod 19 with its uniformly increasing diameter threading 17 (as well as the adjoining uniform threading 65 on rod 19) are turned and threaded into the conical-shaped threaded core 62 (as well as into the adjoining threaded core of uniform diameter which forms the interior of fixed diameter portion 45) of size-adjustable gear 18+88 using the electric motor 14 to lift upper part 88 into an opened position relative to lower part 18. When electromagnet 16 is deactivated by computer 15, the size-adjustable gear 18+88 is allowed to turn freely and accomplish its function with its newly adjusted diameter. Then, when a smaller diameter or power of size-adjustable gear 18+88 is required for a different convergence ratio, the electromagnet 16 is activated again by computer 15 and the uniformly increasing diameter threading 17 (as well as the adjoining uniform threading 65) of rod 19 are turned and unthreaded from core 62 (as well as from the adjoining threaded core of uniform diameter which forms the interior of fixed diameter portion 45) using the electric motor 14 in opposite direction, which allows the springs 60 to bias upper part 88 of the size-adjustable gear 18+88 into a closed position. FIG. 33 is a side view of the truncated-cone-shaped portion of rod 19 in the most preferred embodiment of the present invention, with its uniformly increasing diameter threading 17 and the uniform threading 65 remote from the wide end of the uniformly increasing diameter threading 17. In contrast, FIG. 34 is a perspective view of the uniformly increasing diameter threading 17 on rod 19 in the most preferred embodiment of the present invention shown in a position adjacent to the size-adjustable gear 18+88, which remains in a closed position. Uniformly increasing diameter threading 17 faces the conical-shaped threaded core 62 shown in FIG. 31. The fixed diameter portion 45 of size-adjustable gear 18+88 is hidden from view in FIG. 34.

FIGS. 35 and 36 provide examples of convergence calculations for the most preferred embodiment of the present invention, with FIG. 35 illustrating the convergence needed for a nearby target object 59 and FIG. 36 illustrating the convergence typical for a far away target object 59. FIG. 35 shows two different camera positions usable with a closer target object 59, one resulting in a 100:4 ratio of convergence and the other resulting a 100:2 ratio of convergence. In contrast, FIG. 36 two different camera positions usable with a target object 59 more distant than that shown in FIG. 35, both resulting in a 100:1 ratio of convergence where 1 mm of turning movement in the diagnostic/sensor probe gear convergence arc corresponds to 100 mm of linear movement in the moving cylinder sheath 1. By way of contrast, a 3:100 ratio of convergence is where 3 mm of turning movement in the diagnostic/sensor probe gear convergence arc corresponds to 100 mm of linear movement in the moving cylinder sheath 1. Thus, the maximum measurement of the arc of convergence on the diagnostic/sensor probe gears can be calculated after the maximum distance that the device can move to the visual target 59 is measured, which can be done using a target-to-device distance sensor 66 placed at the distal tip of the main tubular shaft 2, between the probe arms 5 and 6. The target-to-device distance sensor 66 is preferably secured in place by the same hinge 42 used for attachment of the probe arms 5 and 6, and can be activated automatically when the probe arms 5 and 6 are opened. If the target-to-device distance sensor 66 uses laser light as a part of its function, this can also aid in the alignment of the longitudinal axis of main tubular shaft 2 with the visual target 59 (as shown in FIG. 29), and in doing so aid in the adjustment of convergence of diagnostic/sensor probes 3 and 4 on target 59. (In semi-automated configurations where the target-to-device distance sensing capability is not required, a laser pointer is sufficient). This is applicable only to fully automated convergence configurations, and not to semi-automated configurations where a laser pointer is sufficient. In many routine applications that fit the examples provided, the ratio of transformation in convergence can be set to 100:1.5 to provide semi-automated convergence of diagnostic/sensor probed 3 and 4. This is adequate where the differences in convergence ratios at different probe arm 5 and 6 positions and diagnostic/sensor probe 3 and 4 positions are minimal. As needed, the operator can adjust convergence on the visual target 59 manually by using the rotatable manual control 8 that controls adjustment ring 7 movement. Where a very high level of accuracy in convergence is required in an application, fully automated convergence is available via a computer 15 programmed to calculate updated transformation ratios as application needs change. Position sensors (not identified by number as it would be an integral part of diagnostic/sensor probes 3 and 4), an electric motor 14, an electromagnet 16, and a size-adjustable gear (18+88) are also used for implementing the fully automated convergence changes. The transformation ratio ranges are calculated by dividing the maximum distance the device can move to the visual target 59 into the maximum angle of convergence on the diagnostic/sensor probe gears 31 and 32. By knowing this information, the computer can then calculate the needed change in the dimension of the size-adjustable gear (18+88) and automatically turn the electromagnet 16 on to produce resistance in the turning movement of the size-adjustable gear (18+88) to allow the threaded rod 19 inside the size-adjustable gear (18+88) to turn and change its diameter dimension. Another sensor (not shown) in the size-adjustable gear (18+88) will send feedback to computer 15 when the required change in the size-adjustable gear (18+88) is obtained to turn off electromagnet 16 and electric motor 14.

FIG. 35 relates to diagnostic/sensor probe 3 and 4 convergence in two different camera positions where the target object is very close. One resulting calculation shows a 4:100 ratio of convergence is needed, and the other shows a 2:100 ratio of convergence being required. These calculations are for simplification only and needed ratios can change completely depending on the sizes, diameters, lengths and shapes of the main tubular shaft 2, moving cylindrical sheath 1, adjustment ring 7, gears (whether linear or circular), and belts that used are selected prior to manufacture according to application requirements. Thus, in camera position 1 in FIG. 35, one can observe the calculation of an updated ratio of convergence to require the measurement of the following. First, the distance between the mid point of the horizontal line extending between the center points (axes) of both diagnostic/sensor (shown as 31 and 32 in other Figs.) and the visual target object must be determined. This distance is the maximum distance that the device can move toward the visual target (such forward movement creates simultaneous backward movement of the combined adjustment ring 7 and the moving cylindrical sheath 1 on the main tubular shaft 2). In the first example in FIG. 35 this distance is 24.07 mm. Second, measurement is needed of the maximum convergence arc (arc 1) that diagnostic/sensor probe gears 31 and 32 should turn toward the visual target to achieve maximum convergence. In the first example in FIG. 35 this measurement is 1.01 mm, which is calculated by measuring the angle of convergence (the angle between a first line extending from center (axis) of either diagnostic/sensor probe gears 31 and 32 and the visual target and a second line extending between center points (axes) of both diagnostic/sensor probe gears 31 and 32). In the first example in FIG. 35, this is determined to be 48.61 degree. The circumference of probes gear 31 and 32 is then calculated and the resulting ratio of convergence is 4/100, as follows: The maximum arc of convergence=the angle of convergence (48.61 degree in this example)×Circumference of diagnostic/sensor probe gears (either 31 or 32)/360=1.01 mm in the first example in FIG. 35. After these calculations are made, the maximum convergence arc (arc 1) is divided by the maximum distance to target to obtain the ratio of convergence (1.01/24.07=0.04=4/100, which means that every 4 mm turning movement of the diagnostic/sensor probe gears 31 or 32 to converge on the visual target requires 100 mm linear movement of the adjustment ring 7 and the moving cylindrical sheath 1 backward on the main tubular shaft 2). which occurs simultaneously with the movement of the device toward the visual target (it also means that every 100 mm movement of the device toward the visual target cause 100 mm backward movement of the adjustment ring 7 and the moving cylindrical sheath 1 backward on the main tubular shaft 2 which causes 4 mm turning movement of the diagnostic gear 31 and 32 to converge on the visual target). In camera position 2 in FIG. 35, the ratio of convergence=the maximum convergence arc (arc 2=1.18 mm)/the maximum distance to target (45.29 mm)=1.18 mm/45.29 mm=0.02=2/100 which means that every 100 mm movement of the device toward the visual target cause 100 mm backward movement of the adjustment ring 7 and the moving cylindrical sheath 1 backward on the main tubular shaft 2, which causes 2 mm turning movement of the diagnostic/sensor probe gears 31 and 32 to converge diagnostic/sensor probes 3 and 4 an appropriate amount on the visual target.

In contrast, FIG. 36 is a schematic view of the most preferred embodiment of the present invention identifying imaging probe convergence information for two different camera positions usable with a target object that is more distant than that shown in FIG. 35, both revealing a 1/100 ratio of convergence. These calculations are for simplification only and these ratios can change completely depending on the sizes, diameters, lengths & shapes of main tubular shaft, moving cylindrical sheath, adjustment ring, gears whether linear or circular & belts used that in turn depend on the application the device is meant to be used in. In camera position 1 in FIG. 36, the ratio of convergence=the maximum convergence arc (arc 1=1.74 mm)/the maximum distance to target (178.79 mm)=1.74 mm/178.79 mm=0.009=1/100 which means that every 100 mm movement of the device toward the visual target cause 100 mm backward movement of the adjustment ring 7 and the moving cylindrical sheath 1 backward on the main tubular shaft 2 which causes 1 mm turning movement of the diagnostic gear 31 and 32 to converge on the visual target. In camera position 2 in FIG. 36, the ratio of convergence=the maximum convergence arc (arc 2=1.70 mm)/the maximum distance to target (200 mm)=1.70 mm/200 mm=0.008=1/100 which means that every 100 mm movement of the device toward the visual target cause 100 mm backward movement of the adjustment ring 7 and the moving cylindrical sheath 1 backward on the main tubular shaft 2 which causes 1 mm turning movement of the diagnostic gear 31 and 32 to converge on the visual target.

Now, using the calculations from FIGS. 35 and 36, roughly an average ratio of convergence of 1.5/100 seems appropriate to be used as a predetermined ratio of convergence for a device with these measurements in an application that will fit these device measurements. These measurements will be implemented in the selection of the sizes and shapes of the gears and belts that will transmit the movement of the moving cylindrical sheath 1 and reduce its movement in a ratio of 1.5/100 (mainly done in the gearbox 21), and then mechanically transmit the reduced movement to the diagnostic/sensor probe gears 31 and 32 to actuate the appropriate convergence.

The typical steps used in the most preferred embodiment of the present invention for opening and closing probe arms 5 and 6 include use of manual control 22 located on gearbox 21. Operator movement of control 22 causes gear 58 to rotate, which moves the belt 27 associated with it. The movement of belt 27 is then transmitted to gear 29. As gear 29 moves, the pinion gear 34 mounted on the same axle (see FIGS. 6 and 7) starts to move and as a result of pinion gear 34 and rack engagement 48, the moving rack 48 causes the two-rod control assembly 47 to move up or down, as needed. The attachments 70 and 71 respectively on the distal ends of rack 48 and the opposed rod (no individual numerical designation) of the two-rod control assembly 47, which are respectively in contact with the proximal ends of the probe arms 5 and 6, then provide pushing and pulling forces against probe arms 5 and 6 to respectively close or open them.

Resetting diagnostic/sensor probes 3 and 4 to the neutral or zero position with no convergence (also referred to herein as zero convergence where the longitudinal axes are substantially parallel to one another) can also be rapidly accomplished through the use of on-off switch 55, wherein electromagnet 9 is provided power via electrical wiring 13 and power source 76. The activation of electromagnet 9 immediately releases pinion gear 11 from the rack 73 on adjustment ring 7 and results in free movement of adjustment ring 7 back and forth in relation to moving cylindrical sheath 1 on main tubular shaft 2 without causing convergence (since probe arms 5 and 6 have been brought back to their zero positions). This quick reset of diagnostic/sensor probes 3 and 4 to the zero position via on-off switch 55 on gearbox 21 would typically occur prior to entry of the present invention into a endoscopic port, prior to its withdrawal from a endoscopic port, when redirecting diagnostic/sensor probes 3 and 4 to a new target object 59, or otherwise as needed. If the reset sequence is not accomplished prior to entry of the present invention into a endoscopic port, diagnostic/sensor probes 3 and 4 may not be optimally positioned for successful entry into the endoscopic port. In addition, without the free movement of adjustment ring 7, the main tubular shaft 2, the adjustment ring 7, or any of the components of this invention could be placed at risk of breaking when laparoscopic entry is attempted. The reset sequence is also used when diagnostic/sensor probes 3 and 4 come together to prevent computer 15 from taking additional convergence action. An alternative, is the use of rotatable manual control 8 to decrease convergence.

When cameras first enter a endoscopic port or other cavity, diagnostic/sensor probes 3 and 4 are most commonly oriented parallel to and touching one another, a position where convergence on a target object 59 usually cannot take place and for which the on-off switch 55 on gearbox 21 is turned on to activate electromagnet 9 to disengage pinion gear 11 from rack 73 so as to allow the adjustment ring 7 to move freely in relation to the moving cylindrical sheath 1 without causing convergence. After the device reaches its primary (zero) position with the probe arms 5 and 6 clearing the internal wall of the cavity, and after choosing a visual target and opening the probe arms 5 and 6, the electromagnet 9 is deactivated to allow reengagement of pinion gear 11 to rack 73 and allow convergence to take place. Automated or manual convergence can take place, with automated convergence preferred when increased precision in delivery site location is needed for therapeutic treatment. To achieve manual convergence of diagnostic/sensor probes 3 and 4 prior to present invention use for sensing operations and/or therapeutic treatment, the following sequence of steps typically takes place. A target object 59 is first identified by the operator and laser pointer 66 is turned on. The laser pointer 66 mounted on the distal end of the main tubular shaft 2 is then used by the operator to align main tubular shaft 2 with target object 59. Rotatable manual control 8 is first manipulated by the operator to manually move adjustment ring 7 forward or backward an arbitrary amount in an attempt to achieve or improve convergence. If the operator moves adjustment ring 7 forward, moving cylindrical sheath 1 moves back from the distal end of main tubular shaft 2 (secondary to that forward movement of the adjustment ring 7 is obstructed by the external structure of the endoscopic port). The moving cylindrical sheath 1 moves, its integral rack 86 (see FIG. 26) moves pinion gear 54, then causes the gear 28 mounted on the same axle to move and via belt 26 the movement of gear 28 is transmitted to the set of multiple gears in gearbox 21 that are identified numerically in combination by the number 56. Movement of the set of multiple gears 56 then causes the set of multiple gears in gearbox 21 identified numerically in combination by the number 57 to move belt 38, which causes the gear 30 also associated with it to move. The gear 30 to which belt 38 is connected is one of a pair of gears marked with the numerical designation of 30 in FIG. 4. The turning of the first gear 30 by belt 38 causes the second gear 30 mounted on the same axle to move. The belts 36 and 37 connected to the second gear 30 then move the diagnostic/sensor probe gears 31 and 32 associated with the opposing ends of belts 36 and 37, which cause diagnostic/sensor probes 3 and 4 to converge. In contrast, a backward (pulling) movement of the main tubular shaft 2 away from the visual target being viewed allows the adjustment ring 7 (and the moving cylindrical sheath 1 connected to it) to spring and slide forward on the main tubular shaft 2 until it contacts the external structure of the endoscopic port. This spring/slide forward movement is actuated by the spring 49 positioned between the moving cylindrical sheath 1 and a radially-extending brace 85 secured to the distal end of outer shell 23. The spring/slide forward movement of moving cylindrical sheath 1 affects gear 54 on the main tubular shaft 2 and repeats the same steps of mechanical movement transmission mentioned above, but in the opposed direction (the movement of all gears 54, 28, 56, 57, 30 (pair), 31, and 32 in the reverse direction causes less convergence). The manual steps outlined immediately above for manual convergence via rotatable manual control 8 can be used at any time to provide a needed correction resulting from drift and other causes. In contrast, fully automated convergence can also be used and requires that shaft-to-target distance information from the shaft-to-target distance sensor 66 be given to computer 15 and sensors (not given independent numerical designation but considered an integral part of diagnostic/sensor probes 3 and 4) provide information to computer 15 as to the current distance diagnostic/sensor probes 3 and 4 are separated from one another and pertinent information about their position and/or orientation. Once computer 15 has this information, computer 15 activates electromagnet 16 and motor 14, and then instructs electromagnet 16 provide resistance to motor 14 to slow the movement of size-adjustable gear 18+88 so that the cone-shaped uniformly increasing diameter threading 17 on rod 19 can move toward the cones-shaped threaded core of size-adjustable gear 18+88 and engage it to lift upper part 88 away from lower part 18, thereby opening size-adjustable gear 18+88 sufficiently to achieve the needed convergence effect. Sensors on the size-adjustable gear 18+88, not given independent numerical designation in the illustrations herein but considered an integral part of size-adjustable gear 18+88, provide information to computer 15 as to the amount of separation currently existing between upper part 18 and lower part 88. Sensor feedback to computer 15 allows it to continuously monitor and update convergence to specifications predetermined by the operator, until the operator no longer needs automated convergence.

What is claimed is:

1. A device for therapeutic and other applications, medical and non-medical, and obtaining 3-dimensional human vision simulated imaging with real dynamic convergence in areas inaccessible directly by the human eye and where a high level of convergence accuracy is continuously needed for optimal surveillance and scrutiny of a target object in a cavity, said device comprising:

a main tubular shaft having a distal end, a proximal end, a proximal portion adjacent to said proximal end, an external surface, and at least one longitudinally-extending channel in said external surface;

an outer shell larger in diameter than said main tubular shaft, with said outer shell having opposed ends and both of said opposed ends connected to said main tubular shaft so as to cover said proximal portion and provide fixed connection of said outer shell to said main tubular shaft, at least two imaging probes each having a longitudinal axis, and at least two of said imaging probes being the same kind;

two probe arms each movably mounted on said distal end of said main tubular shaft for a combined 180-degree range movement from a fully closed position where said probe arms are adjacent to one another, said probe arms each having a distal end and a proximal end, each of said probe arms further having one of said same kind imaging probes movably secured thereto in a manner allowing convergence of said same kind imaging probes and the providing of 3-dimensional human vision simulated imaging, said same kind imaging probes also secured to said probe arms so that when said probe arms are in said fully closed position said same kind probes are adjacent to one another;

at least one light source associated with at least one of said imaging probes;

an adjustment ring having a substantially tubular distal end, a proximal end with a separated configuration, and projection means adapted for connection of said distal end to said proximal end to said distal end, said adjustment ring also having a first movement conveying means adapted for relaying movement of said main tubular shaft toward and away from a target object so as to ultimately affect convergence of said same kind imaging probes when needed, said first movement conveying means positioned between said distal end of said adjustment ring and said proximal end of said adjustment ring;

a moving cylindrical sheath having a distal end and a proximal end, with said proximal end of said moving cylindrical sheath positioned between said main tubular shaft and said outer shell for longitudinal movement back and forth along said main tubular shaft, said moving cylindrical sheath also positioned so that said adjustment ring becomes positioned between said main tubular shaft and said distal end of said moving cylindrical sheath, said moving cylindrical sheath also having a second movement conveying means adapted for engagement with said first movement conveying means associated with said adjustment ring so as to allow for movement of said adjustment ring relative to said moving cylindrical sheath, said moving cylindrical sheath, further comprising a third movement conveying means adapted for ultimately moving said imaging probes so as to cause a change in their convergence in response to movement of said main tubular shaft toward and away from the target object, said moving cylindrical sheath further having means adapted for engagement of said moving cylindrical sheath with said adjustment ring and subsequent disengagement therefrom;

a gearbox depending from said proximal end of said outer shell, said gearbox housing mechanical means adapted for reducing movement;

first movement transmitting means adapted for transmitting movement of said moving cylindrical sheath and said adjustment ring on said main tubular shaft to said mechanical means in said gearbox;

second movement transmitting means adapted for transmitting reduced movement from said mechanical means in said gearbox to said imaging probes to achieve convergence;

third movement transmitting means adapted for providing reset of said imaging probes so that said longitudinal axes are substantially parallel to one another;

fourth movement transmitting means adapted for opening and closing said probe arms; and control means adapted for activation of at least one of movement transmitting means so that when said at least two imaging probes and said distal end of said main tubular shaft are inserted into a cavity, and said moving cylindrical sheath and said adjustment ring are joined together for movement as one unit, said main tubular shaft and said at least two imaging probes slide easily into the cavity but said adjustment ring is stopped from entering the cavity, and continued forward movement of said main tubular shaft into the cavity toward a target object causes movement of said adjustment ring in a backward direction and causes backward movement of said of said moving cylindrical sheath, wherein said backward movement of said of said moving cylindrical sheath is mechanically transmitted via said first and second movement transmitting means to said gearbox for reduction and then causing each of said imaging probes to turn on its axis and increase their convergence the amount needed to accommodate the increased target object distance, whereby 3-dimensional human vision simulated imaging with real dynamic convergence can be achieved with said at least two imaging probes of the same kind.

2. The device of claim 1 further comprising at least one computer, a motor, at least one electromagnet and at least one size-adjustable gear within said gearbox, and a target-to-device distance sensor secured to said distal end of said main tubular shaft, with said at least one computer activating said motor and said at least one electromagnet to cause said size-adjustable gear to changes its diameter dimension according to the amount of desired convergence needed for said at least two imaging probes of the same kind.

3. The device of claim 1 further comprising pulleys selected from a group consisting of at least two movement transmitting double pulleys working in concert, and at least two movement transmitting double pulleys working in concert with at least one of them having gear teeth configured for engaging other gears.

4. The device of claim 1 wherein said second movement transmitting means comprises a first belt formed into a simple loop and a second belt crossed over itself to form a figure-8 configuration.

5. The device of claim 1 wherein said adjustment ring has a linear gear, and further comprising a pinion gear configured for engaging said linear gear and preventing movement of said adjustment ring relative to said moving cylindrical sheath and said main tubular shaft when in an engaged position with said linear gear, and further comprising a manual control means for said pinion gear that extends through said moving cylindrical sheath and is configured to control the movement of said adjustment ring back and forth on said moving cylindrical sheath.

6. The device of claim 1 wherein said first movement transmitting means adapted for providing movement of said adjustment ring and said moving cylindrical sheath relative to said main tubular shaft comprises three sets of rollers, with each of said sets having four of rollers, and a first one of said sets of rollers associated with said distal end of said adjustment ring, a second one of said sets of rollers associated with said distal end of said moving cylindrical sheath, and a third one of said sets of rollers associated with said proximal end of said moving cylindrical sheath, said first set of four rollers being positioned and adapted for facilitating smooth movement back and forth of said adjustment ring on said main tubular shaft, and said second and third sets of four rollers each being adapted for facilitating smooth movement back and forth of said moving cylindrical sheath on said main tubular shaft, all of said rollers having one end engaging one of said longitudinally-extending channels of said main tubular shaft.

7. The device of claim 1 further comprising at least one channel configured and positioned to allow the concurrent introduction and use of at least one independent instrument inside the cavity where said device is inserted, and wherein said at least one independent instrument is selected from a group consisting of medical instruments, mechanical instruments, instruments using electrical power to function, endoscopic scissors, graspers, and biopsy forceps.

8. The device of claim 1 further comprising at least one spring selected from a group consisting of springs connected between said moving cylindrical sheath and said main tubular shaft, springs connected between said adjustment ring and said moving cylindrical sheath, and springs mounted in said probe arms for assisting movement of said imaging probes.

9. A device for obtaining 3-dimensional human vision simulated imaging of a target object with real dynamic convergence in therapeutic and other applications, medical and non-medical, where the target object is located behind a limited-access opening with associated external structure, said device comprising:

a main tubular shaft having a distal end with an angled distal tip, a proximal end, a proximal portion adjacent to said proximal end, an exterior surface, and a set of four longitudinally-extending channels in said external surface that are spaced apart from one another;

an outer shell larger in diameter than said main tubular shaft, said outer shell positioned to cover said proximal portion of said main tubular shaft, said outer shell having a distal end and a proximal end;

four radially-extending braces, two of said braces connecting said distal end of said outer shell to said main tubular shaft and two of said braces connecting said proximal end of said outer shell to said proximal end of said main tubular shaft, said braces providing fixed connection of said outer shell to said main tubular shaft;

a moving cylindrical sheath having a distal end and a proximal end, and positioned for longitudinal movement back and forth along said main tubular shaft, with said proximal end of said moving cylindrical sheath further positioned between said main tubular shaft and said outer shell, said moving cylindrical sheath also having two pairs of longitudinally-extending opposing slots extending substantially its full length, said moving cylindrical sheath also having a linear gear and five interior longitudinally-extending groove, with said moving cylindrical sheath further comprising a movement conveying means adapted for ultimately moving imaging probes so as to cause a change in their convergence in response to movement of said main tubular shaft toward and away from a target object;

a first spring means adapted for connection between said moving cylindrical sheath and one of said radially-extending braces secured to said distal end of said outer shell;

an adjustment ring positioned between said main tubular shaft and said distal end of said moving cylindrical sheath, said adjustment ring having four longitudinally-extending projection rods depending from a closed circular distal end, a longitudinally-extending linear gear, and two-part arcuate proximal end;

a second spring means adapted for connection between said two-part proximal end of said adjustment ring and said distal end of said moving cylindrical sheath;

three sets of four rollers each, with said first set of four rollers associated with said distal end of said adjustment ring, said second set of four rollers associated with said distal end of said moving cylindrical sheath, and said third set of four rollers associated with said proximal end of said moving cylindrical sheath, said first set of four rollers being positioned and adapted for facilitating movement of said adjustment, ring on said main tubular shaft, and said second and third sets of four rollers each being adapted for facilitating movement of said moving cylindrical sheath on said main tubular shaft, all of said rollers having one end engaging one of said longitudinally-extending channels of said main tubular shaft;

two probe arms each movably mounted on said distal end of said main tubular shaft for a combined 180-degree range movement from a fully closed position where said probe arms are adjacent to one another, said probe arms each having a distal end, a proximal end, an angled configuration complementary to that of said distal tip so that said angled configurations define said 180-degree maximum angle range of movement of said probe arms;

hinging means adapted for pivotal connection of said proximal ends of said probe arms;

at least two imaging probes associated with said probe arms and at least two of said imaging probes being the same kind, with each of said probe arms having one of said same kind movably secured thereto in a manner allowing convergence of said same kind imaging probes and the providing of 3-dimensional human vision simulated imaging, said same kind imaging probes also secured to said probe arms so that when said probe arms are in said fully closed position said same kind probes are adjacent to one another;

at least two imaging probe gears, with at least one of said imaging probe gears on each of said probe arms, each of said imaging probe gears also associated with one of said imaging probes;

a gearbox depending from said proximal end of said outer shell, said gearbox housing mechanical means adapted for reducing movement comprising at least one set of multiple gears pre-configured for creating convergence according to a pre-determined transformation ratio;

first movement transmitting means adapted for transmitting movement of said moving cylindrical sheath and said adjustment ring on said main tubular shaft to said mechanical means in said gearbox, said first movement transmitting means also comprising an axle mounted on said moving cylindrical sheath and a first pinion gear having a cone-shaped configuration, said axle having a proximal end and a distal end, with said distal end of said axle connected to said rotatable manual control and said proximal end of said axle connected to said first pinion gear that is positioned in moving engagement with said linear gear of said adjustment ring, said first movement transmitting means further comprising a second pinion gear in moving engagement with said linear gear of said moving cylindrical sheath, a first movement transmitting gear journaled for rotation with said second pinion gear; a first movement transmitting belt having two opposed ends, with one of said opposed ends positioned for moving engagement with said first movement transmitting gear and the other of said opposed ends positioned for moving engagement with said movement reducing mechanical means in said gearbox;

second movement transmitting means adapted for transmitting reduced movement from said mechanical means in said gearbox to said imaging probes to achieve convergence, said second movement transmitting means also comprising a set of two gears journaled for rotation between said imaging probes, a second movement transmitting belt having two opposed ends, with one of said opposed ends positioned for moving engagement with said set of two gears and the other of said opposed ends positioned for moving engagement with said movement reducing mechanical means in said gearbox, two probe belts each connected between said set of two gears and one of said imaging probe gears;

third movement transmitting means adapted for providing reset of said imaging probes so that said longitudinal axes are substantially parallel to one another, said third movement transmitting means also comprising an on-off switch, at least one electromagnet, electrical wiring, at least one power source, said cone-shaped pinion gear, said longitudinally-extending linear gear of said adjustment ring, said set of two gears, said second movement transmitting belt, and said probe belts;

a probe arm control associated with said gearbox;

fourth movement transmitting means adapted for opening and closing said probe arms, said fourth movement transmitting means also comprising a two-rod control assembly having two rods and a linear gear associated with one of said rods, said rod with a linear gear and the other one of said rods each having a distal end attachment to a different one of said probe arms, a third pinion gear in moving engagement with said linear gear of said two-rod control assembly; a third movement transmitting belt having two opposed ends, with one of said opposed ends positioned for moving engagement with said third pinion gear and the other of said opposed ends positioned for moving engagement a gear journaled for rotation on the same axis used for rotation of said probe arm control;

a rotatable manual control journaled for rotation with said first cone-shaped pinion gear and adapted for providing movement of said adjustment ring and said moving cylindrical sheath relative to one another, and an on-off switch configured and positioned for reset of said imaging probes so that said longitudinal axes of said imaging probes are placed into a position substantially parallel to one another;

whereby said on-off switch is used to reset the orientation of said imaging probes relative to one another prior to entry into a cavity having a limited-access opening with associated external structure, when said angled distal tip on said distal end of said main tubular shaft is moved beyond the external structure of a limited-access opening and through it into a cavity, and after initial entry into the cavity before any convergence takes place, and thereafter when said probe arms are moved apart from one another using said probe arm control, and said imaging probes are moved closer to and away from a target object so as to require convergence adjustment, movement of said adjustment ring and said moving cylindrical sheath back and forth . along said main tubular shaft as customized by said longitudinally-extending channels, said rollers, and said springs, is transmitted via said first movement transmitting means to said mechanical means in said gearbox which creates a reduced movement that is then transmitted via said second movement transmitting means to said imaging probes to achieve 3-dimensional human vision simulated imaging with real dynamic convergence, wherein forward movement of said main tubular shaft toward a target object and the resulting backward movement of said adjustment ring and said moving cylindrical sheath that is caused by the external structure associated with the limited access opening blocking their forward movement, then causes each of said imaging probe gears to turn on its axis and thus increase the amount of convergence for said imaging probes on the target object, and conversely wherein a backward movement of said main tubular shaft away from the visual target being viewed results in said first spring means causing said adjustment ring and said moving cylindrical sheath to spring and slide forward on said main tubular shaft, thereby causing each of said imaging probe gears to turn on its axis in the opposed direction and thus decrease the amount of convergence for said imaging probes on the target object.

10. The device of claim 9 further comprising features selected from a group consisting of lights, therapeutic devices, therapeutic radiation devices, radio-frequency devices, laser devices, non-medical radiation devices, and a size-adjustable gear having a cone-shaped threaded core.

11. A method for using a device producing 3-dimensional human vision simulated imaging of a target object with real dynamic convergence in therapeutic and other applications, medical and non-medical, where the target object is located behind a limited-access opening, said method comprising the steps of:

providing a target object behind a limited access opening and a device configured to produce 3-dimensional human vision simulated imaging of a target object with real dynamic convergence and having an elongated main tubular shaft with a proximal end and an opposed distal end with a distal tip, a gearbox associated with said proximal end and a hinge associated with said distal tip, two probe arms each having a proximal end and an opposed distal end with each said proximal end pivotally connected to said hinge so that said probe arms can be opened and closed in concert from side-to-side freely within a 180-degree angle range of movement from a fully closed position where said probe arms are adjacent to one another to a fully opened position where each said probe is approximately 90-degrees away in an opposite direction from its fully closed position, said imaging probes each having a longitudinal axis and at least two imaging probes connected to said distal ends of said probe arms with two of said imaging probes being the same kind and each of said same kind of imaging probes being on a different one of said probe arms, said imaging probes also being adapted to move in opposed directions, a moving cylindrical sheath engaged with said main tubular shaft for back and forth linear movement along said main tubular shaft and having movement conveying means adapted for ultimately moving said imaging probes so as to cause a change in their convergence in response to movement of said main tubular shaft toward and away from the target object, a spring connected between said moving cylindrical sheath and said main tubular shaft, first mechanical movement transmitting means adapted for transmitting said linear movement of said moving cylindrical sheath to said gearbox, a set of multiple gears in said gearbox that are configured to reduce said transmitted linear movement of said moving cylindrical sheath by a pre-determined amount, and a second mechanical movement transmitting means adapted for transmitting said reduced movement to said imaging probes;

inserting said distal end of said main tubular shaft through said limited access opening with said probe arms in a zero position where said probe arms are adjacent to one another;

moving said probe arms out of said zero position away from one another into an opened position;

advancing said distal end toward said target object into a shortened distance from said target object wherein said moving cylindrical sheath experiences linear movement away from said target object relative to said main tubular shaft, said first mechanical movement transmitting means transmits said backward linear movement to said gearbox, said set of multiple gears in said gearbox reducing said backward linear movement by a pre-determined amount to create a quantity of reduced movement, and said second mechanical movement transmitting means transmitting said quantity of reduced movement to said imaging probes appropriate to cause them to move toward one another for convergence on said target object while said probe arms remain in said opened position and said distal tip remains at said shortened distance from said target object; and moving said distal end away from said target object into a lengthened distance from said target object wherein said moving cylindrical sheath experiences linear movement toward said target object via action of said spring connected between said moving cylindrical sheath and said main tubular shaft, said first mechanical movement transmitting means transmits said forward linear movement to said gearbox, said set of multiple gears in said gearbox reducing said forward linear movement by a pre-determined amount to create a quantity of reduced movement, and said second mechanical movement transmitting means transmitting said quantity of reduced movement to said imaging probes appropriate to cause them to move away from one another for convergence on said target object while said probe arms remain in said opened position and said distal tip remains at said lengthened distance from said target object.

12. The method of claim 11 further comprising the steps of providing an adjustment ring, associating said adjustment ring with said moving cylindrical sheath so that both are able to move together relative to said main tubular shaft to actuate convergence movement in said imaging probes in response to movement of said distal end of said main tubular shaft toward and away from said target object.

13. The method of claim 12 further comprising the steps of providing rotatable manual control, associating said rotatable manual control with said adjustment ring for movement of said adjustment ring relative to said moving cylindrical sheath to manually control convergence movement in said imaging probes.

14. The method of claim 13 further comprising a pinion gear being used in said step of associating said rotatable manual control with said adjustment ring for its movement to manually control convergence and wherein a primary position with zero convergence is defined as a position where said longitudinal axes of said imaging probes are parallel to one another, and said method further comprises the step of providing an on-off switch, an electromagnet associated with said rotatable manual control, a remote power supply, and electrical wiring, and a spring located between electromagnet and said pinion gear associated with said manual control means, the step of associating said electrical wiring with said on-off switch, said electromagnet, and said power supply to provide power between said on-off switch and said electromagnet, and the step of associating said electromagnet with said adjustment ring in a manner to cause said pinion gear to be released from said adjustment ring linear gear and during said release said pinion gear causing said spring to become compressed thus allowing separation of said adjustment ring from said moving cylindrical sheath when said on-off switch is activated thereby providing power to said electromagnet wherein after said adjustment ring can move independently from said moving cylindrical sheath which can be used to rapidly reset said imaging probes to said primary position with zero convergence until said on-off switch is again activated to turn off power to said electromagnet wherein said spring will cause said pinion gear to again move into engagement with said linear gear.

15. The method of claim 11 further comprising the step of providing a two-rod control assembly with two longitudinally-extending rods, a rack on a first one of said rods, and the second one of said rods and said rack each having a distal end attachment, the step of associating said two-rod control assembly with said main tubular shaft for movement in and out of said distal end of said main tubular shaft, the step of associating each of said distal end attachment of said two-rod control assembly with a different one of said probe arms so as to provide the pushing and pulling forces needed to respectively close and open said probe arms according to need, the step of providing a rotatable control on gearbox and a third mechanical movement transmitting means adapted for transmitting movement of said rotatable control into linear movement of said two-rod control assembly in and out of said distal end of said main tubular shaft, and the step of using said rotatable control for opening and closing said probe arms so that convergence of said imaging probes can occur at most probe arm positions between said fully opened probe arm position and said fully closed probe arm position.

16. The method of claim 11 wherein said main tubular shaft has a proximal portion, and further comprising a step of providing a feature selected from a group consisting of at least one handle and at least one outer shell larger in diameter than said main tubular shaft with said outer shell having opposed ends both connected to said main tubular shaft so as to cover said proximal portion, and further comprising the step of using said feature for enhanced operator manipulation of said device.

17. The method of claim 11 wherein said imaging probes are selected from a group consisting of ultra-sound imaging probes, diagnostic probes, therapeutic probes, sensing probes, and cameras.

18. The method of claim 11 wherein when adapted for semi-automated use said first mechanical movement transmitting means, said second mechanical movement transmitting means and said third mechanical movement transmitting means are selected from a group consisting of gears, paired gears, cone-shaped gears, at least one electromagnet, an electromagnet associated with at least one cone-shaped gear so as to cause movement of said least one cone-shaped gear when said electromagnet is activated, belts, pulleys, pulleys with teeth, cables, a set of multiple gears selected to reduce linear movement by a pre-determined amount, at least one computer, at least one motor, at least one electromagnet, at least one linear solenoid, and at least one size-adjustable gear.

19. The method of claim 11 wherein fully automated use further comprises the step of providing at least one computer, at least one motor, at least one electromagnet, at least one size-adjustable gear, at least one positioning sensor associated with said imaging probes, at least on positioning sensor associated with said size-adjustable gear, and at least one positioning sensor associated with said distal tip and positioned to determine tip-to-target distance, the step of connecting said at least one computer to said positioning sensors, said motor, and said electromagnet, the step of said computer periodically receiving information from said positioning sensors and determining whether a convergence correction is needed, and the step of said computer activating said electromagnet and said motor when a convergence correction is needed to adjust said size-adjustable gear so that it creates the proper ratio of convergence needed for movement reduction that is then mechanically transmitted to said imaging probes to move them and provide fully automated imaging probe convergence.

20. The method of claim 11 further comprising the step of providing mounting means for movably securing said imaging probes on said probe arms that are selected from a group consisting of mounting means having a different probe gear associated with each said imaging probe, a first flexible probe belt connected to one of said imaging probe gears that forms a simple loop, and a second flexible probe belt connected to one of said imaging probe gears that forms a figure eight; mounting means comprising a different imaging probe gear associated with each said imaging probe, at least one gear axle associated with each said probe arm, a separate support post in fixed and substantially perpendicular association with each said gear axle, a first flexible probe belt connected to one of said imaging probe gears that forms a simple loop, and a second flexible probe belt connected to one of said imaging probe gears that forms a figure eight; and mounting means having a different probe gear associated with each said imaging probe, at least one gear axle associated with each said probe arm, at least four mounting blocks and two springs associated with said axle, a first probe belt connected to one of said imaging probe gears that forms a simple loop, and a second probe belt connected to one of said imaging probe gears that forms a figure eight.

* * * * *